US007455990B2

(12) United States Patent
Johansen et al.

(10) Patent No.: US 7,455,990 B2
(45) Date of Patent: Nov. 25, 2008

(54) METHOD OF EXTRACTING RECOMBINANT HEXOSE OXIDASE

(75) Inventors: Claus Lindvald Johansen, Højbjerg (DK); Søren Kjaerulff, Hillerød (DK); Susan Mampusta Madrid, Vedbaek (DK); Henrik Pedersen, Østbirk (DK); Charlotte Horsmans Poulsen, Braband (DK); Masoud Rajabi Zargahi, Åbyhøj (DK)

(73) Assignee: Danisco A/S, Copenhagen (DK)

( * ) Notice: Subject to any disclaimer, the term of this patent is extended or adjusted under 35 U.S.C. 154(b) by 244 days.

(21) Appl. No.: 10/693,234

(22) Filed: Oct. 24, 2003

(65) Prior Publication Data

US 2004/0253671 A1 Dec. 16, 2004

Related U.S. Application Data

(63) Continuation-in-part of application No. 09/722,938, filed on Nov. 27, 2000, now abandoned, which is a continuation of application No. PCT/IB00/01886, filed on Nov. 24, 2000.

(30) Foreign Application Priority Data

Nov. 24, 1999 (GB) .................................. 9927801.2

(51) Int. Cl.
*C12P 21/06* (2006.01)
*C12N 9/04* (2006.01)
*C12N 1/21* (2006.01)
*C12N 1/15* (2006.01)
*C12N 1/19* (2006.01)
*C07H 21/04* (2006.01)

(52) U.S. Cl. .................... 435/69.1; 435/190; 435/252.3; 435/254.11; 536/23.2

(58) Field of Classification Search .................. 530/422; 435/189; 536/23.2
See application file for complete search history.

(56) References Cited

U.S. PATENT DOCUMENTS

| | | | |
|---|---|---|---|
| 3,801,461 A | 4/1974 | Miyake et al. | 435/193 |
| 4,346,018 A | 8/1982 | Carter et al. | 436/17 |
| 4,372,888 A | 2/1983 | Hjelmeland | 552/550 |
| 4,683,293 A | 7/1987 | Craig | 530/359 |
| 4,968,629 A | 11/1990 | Lapicola | 436/18 |
| 5,124,256 A | 6/1992 | Crahay et al. | 435/71.1 |
| 5,132,205 A | 7/1992 | Pronovost et al. | 435/5 |
| 5,240,834 A | 8/1993 | Frankel et al. | 435/71.2 |
| 5,922,573 A | 7/1999 | Boraschi et al. | 435/69.52 |
| 5,977,306 A | 11/1999 | Grieve et al. | 530/350 |
| 6,251,626 B1 | 6/2001 | Stougaard et al. | 435/69.1 |

FOREIGN PATENT DOCUMENTS

| EP | 0 363 110 A | 9/1989 |
|---|---|---|
| EP | 0 488 269 | 6/1992 |
| EP | 0 833 563 B1 | 9/1999 |
| WO | WO 96/26280 | 8/1996 |
| WO | WO 96/39851 | 12/1996 |
| WO | WO 96/40935 | 12/1996 |
| WO | WO 96 40935 A | 12/1996 |
| WO | WO 98 02559 | 1/1998 |
| WO | WO 98/13478 | 4/1998 |

OTHER PUBLICATIONS

Sundhey et al. (May 1995) Small Ruminant Research, vol. 16, No. 3, pp. 251-261.*
Puri et al (Aug. 1, 1992) The Biochem. Journal, vol. 285, pp. 871-879.*
Ahlstrom and Edebo 1994 FEMS Microbiology Letters 119 7-12.
Altschul et al. 1990 J. Mol. Biol., 403-410.
Bhat et al., "Detergent Permeabilized Yeast Cells as the Source of Intracellular Enzymes for Estimation of Biomolecules," Enzyme Microb. Technol., 15: 796-800, 1993.
Devereux et al. University of Wisconsin, USA; Devereux et al. 1984, Nucleic Acids Research 12:387.
Gowda, L.R., Bachhawat, N. and Bhat, S.G. (1991) Permeabilization of baker's yeast by cetyltrimethylammonium bromide for intracellular enzyme catlysis. Enzyme Microb. Technol. 13, 154-157.
Hagan, I.M. and Hyams, J.S. (1988) J. Cell Sci. 89, 343-357.
Hansen, O.C., and Stougaard, P. (1997) Hexose oxidase from the red alga *Chondrus crispus*: purification, molecular cloning, and expression in *Pichia pastoris*. J. Biol. Chem. 272, 11581-11587.
Hunkapiller, M.W., Lujan, U., Ostrander, F., and Hood, L.E. (1983) Isolation of proteins from polyacrylamide gels for amino acid sequence analysis. Methods in Enzymology, 91:227-236.
Ishaq et al 1990 Biotechniques 9(1), 19-20, 22,24.
Joshi, M.S., Gowda, L. R., Katwa, L.C. and Bhat, S.G. (1989) Permeabilization of yeast cells (*Kluyveromyces fragilis*) to lactose by digitonin. Enzyme Microb. Technol. 11, 439-443.
Joshi, M.S., Gowda, L.R. and Bhat, S.G. (1987) Permeabilization of yeast cells (*Kluyveromyces fragilis*) to lactose by cetyltrimethylammonium bromide. Biotechnol. Lett. 9, 549-554.

(Continued)

*Primary Examiner*—Elizabeth Slobodyansky
(74) *Attorney, Agent, or Firm*—Frommer Lawrence & Haug LLP; Thomas J. Kowalski; Angela M. Collison

(57) ABSTRACT

A method is described for releasing a soluble or membrane associated intracellular protein of interest (POI) comprising the steps of: providing a cell comprising a soluble or membrane associated intracellular POI; contacting the cell with a membrane extracting composition; and causing the POI to be released from the cell under conditions sufficient for the specific release of the POI and in a soluble form.

13 Claims, 24 Drawing Sheets

OTHER PUBLICATIONS

Kambouris et al. 1999 FEMS Immunol Med Microbiol. 25(3) 255-64.

King, A.T., Davey, M.R., Mellor, I.R., Mulligan, B.J. and Lowe, K.C. (1991) Surfactant effects on yeast cells. Enzyme Microb. Technol. 13, 148-153.

Kuipers et al 1999 Ann Rheum Dis 58(2) 103-8.

Mietzner et al. (1987) Journal of Experimental Medicine, vol. 165, No. 4, p. 1041-1057.

Milto and Detschart 1998 1998 Parasitol Res 84(7) 596-7.

Murray E et al 1989, Nuc Acids Res 17:477-508.

Neglak, T.J. Hettwer, D.J. and Wang, H.Y. (1990) Chemical permeabilization of cells for intracellular product release. In Separation process in biotechnology (Asenjo, J.A. ed) vol. 9, chapter 7. M. Dekker, New York.

Poulsen, C.H. and Hostrup, P.B. (1998) Purification and characterization of a hexose oxidase with excellent strengthening effects in bread. Cereal Chem. 75, 51-57.

Reineke et al. 1998 Insect Mol Biol 7(1) 95-9.

Sekhar, S., Bhat, N. and Bhat, S.G. (1999) Preparation of detergent permeabilized Bakers' yeast whole cell catalase. Process Biochem 34, 349-354.

Sullivan, J.D. and Ikawa, M. (1973) Purification and characterization of hexose oxidasefrom the red alga chondrus crispus. Biochem. Biophys. Acta 309,11-12.

Velegraki et al. 1999 Med Mycol 37(1) 69-73.

White et al. 1998 Med Mycol 36(5) 299-303.

Woodhead et al. 1998 Mol Biotechnol 9(3) 243-6.

Zhang et al 1998 J. Virol Methods 71(1) 45-50.

Merck Index, 12th edition (1996), pp. 87-95.

Andrew C. Lennard, "Interleukin-1 Receptor Antagonist", Critical Reviews in Immunology, vol. 15, No. 1, pp. 77-105, (1995).

William P. Arend, "Interleukin-1 Receptor Antagonist", Advances in Immunology, vol. 54, pp. 167-227, (1993).

William P. Arend, "Interleukin-1 Receptor Antagonist: Role in Biology", Annu. Rev. Immunol., vol. 16, pp. 27-55, (1998).

Angus W. Thomson, "The Cytokine Handbook", 3$^{rd}$ Edition, Academic Press, (1998).

Kirsten Bojsen et al., "A group of α-1, 4-glucan lyases and their genes from the red alga *Gracilariopsis lemaneiformis*: purification, cloning, and heterologous expression" Biochimica et Biophysica Acta, vol. 1430, pp. 396-402, (1999).

Tiina Alamae et al., "Permeabilization of the methylotrophic yeast *Pichia pinus* for intracellular enzyme analysis: a quantitative study", Journal of Microbiology Methods, vol. 22, 193-205, (1995).

* cited by examiner

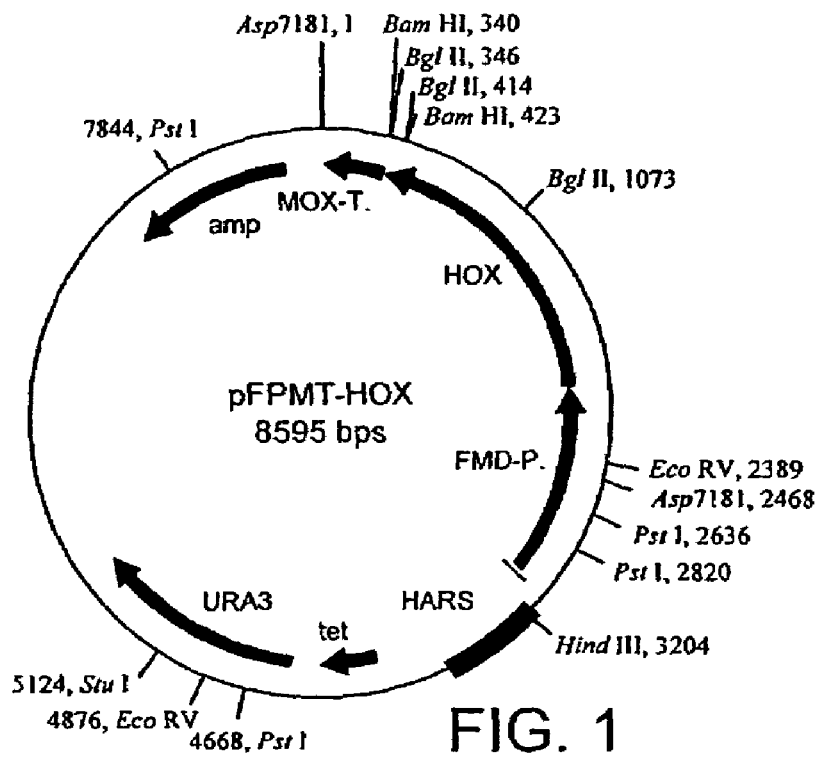
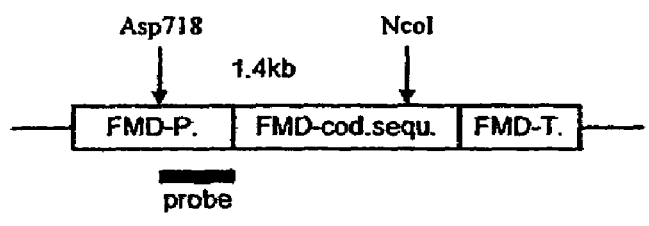
1 copy of the 1.4kb band
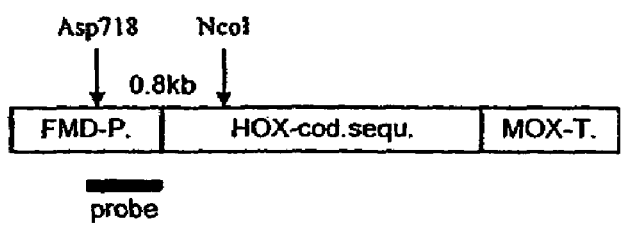
multiple copies of the 0.8kb band
FIG. 2A

FIG. 3A

Supernatants from glycerol-fermentation of strain DK8-27 KanII3-mut25

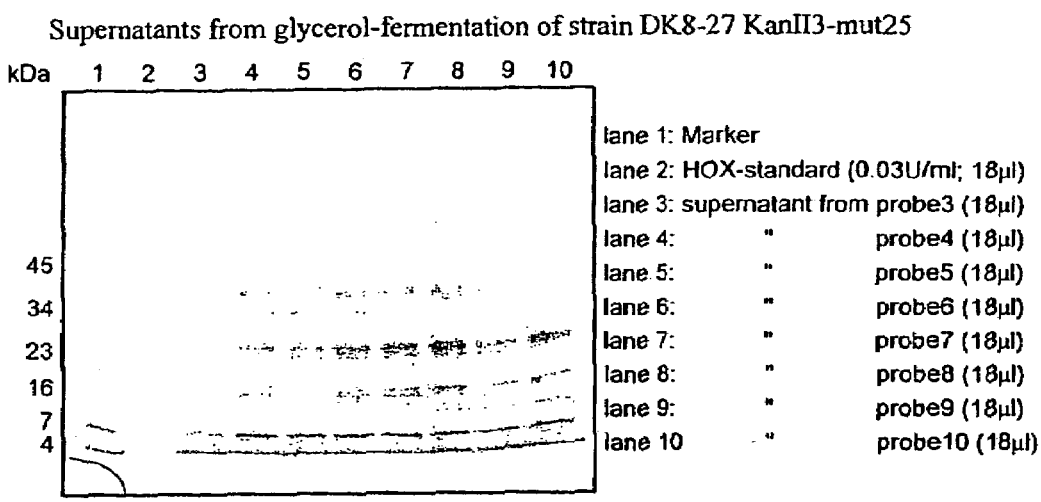

lane 1: Marker
lane 2: HOX-standard (0.03U/ml; 18μl)
lane 3: supernatant from probe3 (18μl)
lane 4:  "          probe4 (18μl)
lane 5:  "          probe5 (18μl)
lane 6:  "          probe6 (18μl)
lane 7:  "          probe7 (18μl)
lane 8:  "          probe8 (18μl)
lane 9:  "          probe9 (18μl)
lane 10: "          probe10 (18μl)

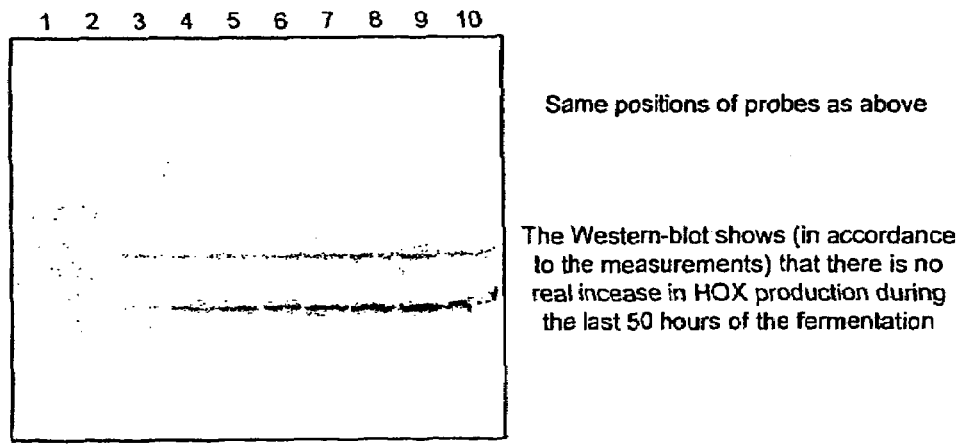

Same positions of probes as above

The Western-blot shows (in accordance to the measurements) that there is no real incease in HOX production during the last 50 hours of the fermentation

FIG. 3B

FIG. 5A hox1A
ACTCCATGGCTACTTTGCCACAAAAGGACCCAGGTTACATTGTTATTGACG
TCAACGCTGG(SEQ ID No 2)

hox2B
CGAAATCGATGTTGGTACCAATCCATCTTCTGTTGAAACCTTGCTTCATGG
ATGGCAATCTTGGGTCAGGCTTGTCTGGAGTACCAGCGTTGACGTCAATAA
CAATG(SEQ ID No 3)

hox3a
GATTGGTACCAACATCGATTTCGTTTACGTCGTTTACACTCCACAAGGTGC
TTGTACTGCTTTGGACAGAGCTATGGAAAAGTGTTCTCCAGGTACCGTCAG
AATC(SEQ ID No 4)

hox4b
TTCAACCAAACCAGTAACGTTGATAATAGCCTTGACACATTCGTCGAAAAC
GAAGTCTTCGTAACAGTGACCACCAGAAACGATTCTGACGGTACCTGGAGA
ACAC(SEQ ID No5)

hox5a
ATCAACGTTACTGGTTTGGTTGAATCTGGTTACGACGACGATAGAGGTTAC
TTCGTCTCTTCCGGTGACACCAACTGGGGTTCCTTCAAGACCTTGTTCAGA
GACCACGGTAGAGTTTTG(SEQ ID No6)

hox6b
CAAACCGTGCAATCTGGCCAAAATACCGTCACCTCCACCGACAATGTGACC
ACCCAAACCGACGGAGTAACAGGAACCACCTGGCAAAACTCTACCGTGGTC
TCTGAAC(SEQ ID No 7)

hox7a
TTTGGCCAGATTGCACGGTTTGCCAGTCGATTGGTTATCCGGTGTTGAAGT
TGTCGTTAAGCCAGTCTTGACCGAAGACTCTGTTCTTAAGTACGTTCACAA
GGATTCC(SEQ ID No 8)

hox8b
GGCAAATCCTTGAAGTAGTATTTGGTGATAATACCGAAGTTACCTCCACCT
CCACCAGTGTGAGCCCAAAACAACTCACCGTCGTTACCTTCGGAATCCTTG
TGAACGTACTTAAG(SEQ ID No 9)

hox9a
CAAATACTACTTCAAGGATTTGCCAATGTCTCCAAGAGGTGTCATCGCTTC
TAACTTACACTTCTCTTGGGACGGTTTCACTAGAGATGCCTTGCAAGATTT
GTTGACTAAGTACTTC(SEQ ID No 10)

hox10b
GGAGGTATACAAGTACATAACAAACTCTTCAGCTGCTTGGTGGAAGATTTG
GAACTTACCAACAGTATTCTTCCAATCACATCTAGCCAACTTGAAGTACTT
AGTCAACAAATCTTGC(SEQ ID No 11)

FIG. 5B primer 1
ATCTTCCATCAGGCAGCTGAAGAGTTTGTTATGTACTTGTATACATCCTAC
TCTAACGACGCCGAGAGAGAAGTTGCCCAAGACAGACACTATCAT
(SEQ ID No 12)

primer 2
GAAAGGAGCCCAACCAGCATGACCACCAAGAGCTTTGGTAGGCTC(    GT
TTTGTAGATCTGTTCAATGTCAGCCTCCAAATGATAGTGTCTGTCTTGGGC
(SEQ ID No 13)

primer 3
GCTGGTTGGGCTCCTTTCCCTGTTAGACCTAGACCTAGACACACATCCAAG
ACTTCTTATATGCATGACGAGACTATGGACTACCCTTTC
(SEQ ID No 14)

primer 4
AATCTGGAAGTCTGGAAAGTCCTTGATCATGTAAGCAGACTTGTACTTACC
TCTCTGATTAGGACCGGAACCGTTGATAGTCTCAGTCAAAGCGTAGAAAGG
GTAGTCCATAGTCTCGTC(SEQ ID No 15)

primer 5
GACTTTCCAGACTTCCAGATTGATGTTATCTGGAAATACCTTACTGAGGTT
CCTGACGGTTTGACTAGTGCCGAAATGAAGGATGCTCTTCTTCAGGTTGAT
ATGTTC(SEQ ID No 16)

primer 6
CTTGTCTTCTTCCTGCCAGTATGTCTGGTACTGCAGTTTGATGATGTACTC
TCTCTGAGCAACTGCAGTAGCATCCCAAACAACCTTGTGAATCTCACCACC
GAACATATCAACCTGAAGAAGAGC(SEQ ID No 17)

primer 7
ACATACTGGCAGGAAGAAGACAAGGATGCAGTTAACTTGAAGTGGATTAGA
GACTTTTACGAGGAGATGTATGAGCCTTATGGTGGTGTTCCAGACCCTAAC
ACTCAG(SEQ ID No 18)

primer 8
GGCACCATACTTACCGTTCTTCCAGTTGTTCAAGTCAACATCAGGGTAGTT
GAAGTAGCATCCCTCAAAAACACCTTTACCACTCTCAACCTGAGTGTTAGG
GTCTGGAAC(SEQ ID No 19)

primer 9
AAGAACGGTAAGTATGGTGCCTTGGAACTTTACTTTTTGGGTAACCTGAAC
AGATTGATCAAGGCCAAATGGTTGTGGGATCCTAACGAGATCTTCACAAAC
AAACAGTCTATCCCT(SEQ ID No 20)

primer 10
GAATTCCGCGGCCGCCTACTATTTAGTCTGCTTAGGCTCCTTAAGAGGTTT
AGTAGGGATAGACTGTTTGTTTGTGAA(SEQ ID No 21)

FIG. 6A
(SEQ ID No 22)

Molecule Name: hoxpic  
Sequence Printed: 1-1644 (Full)  
Description:

1644 bps DNA Linear  
Date Printed 04 Jun 1999

```
  1  ATG GCT ACT TTG CCA CAA AAG GAC CCA GGT TAC ATT GTT ATT
      M   A   T   L   P   Q   K   D   P   G   Y   I   V   I

43  GAC GTC AAC GCT GGT ACT CCA GAC AAG CCT GAC CCA AGA TTG
      D   V   N   A   G   T   P   D   K   P   D   P   R   L

85  CCA TCC ATG AAG CAA GGT TTC AAC AGA AGA TGG ATT GGT ACC
      P   S   M   K   Q   G   F   N   R   R   W   I   G   T

127  AAC ATC GAT TTC GTT TAC GTC GTT TAC ACT CCA CAA GGT GCT
      N   I   D   F   V   Y   V   V   Y   T   P   Q   G   A

169  TGT ACT GCT TTG GAC AGA GCT ATG GAA AAG TGT TCT CCA GGT
      C   T   A   L   D   R   A   M   E   K   C   S   P   G

211  ACC GTC AGA ATC GTT TCT GGT GGT CAC TGT TAC GAA GAC TTC
      T   V   R   I   V   S   G   G   H   C   Y   E   D   F

253  GTT TTC GAC GAA TGT GTC AAG GCT ATT ATC AAC GTT ACT GGT
      V   F   D   E   C   V   K   A   I   I   N   V   T   G

295  TTG GTT GAA TCT GGT TAC GAC GAC GAT AGA GGT TAC TTC GTC
      L   V   E   S   G   Y   D   D   D   R   G   Y   F   V

337  TCT TCC GGT GAC ACC AAC TGG GGT TCC TTC AAG ACC TTG TTC
      S   S   G   D   T   N   W   G   S   F   K   T   L   F

379  AGA GAC CAC GGT AGA GTT TTG CCA GGT GGT TCC TGT TAC TCC
      R   D   H   G   R   V   L   P   G   G   S   C   Y   S

421  GTC GGT TTG GGT GGT CAC ATT GTC GGT GGA GGT GAC GGT ATT
      V   G   L   G   G   H   I   V   G   G   G   D   G   I

463  TTG GCC AGA TTG CAC GGT TTG CCA GTC GAT TGG TTA TCC GGT
      L   A   R   L   H   G   L   P   V   D   W   L   S   G

505  GTT GAA GTT GTC GTT AAG CCA GTC TTG ACC GAA GAC TCT GTT
      V   E   V   V   V   K   P   V   L   T   E   D   S   V

547  CTT AAG TAC GTT CAC AAG GAT TCC GAA GGT AAC GAC GGT GAG
      L   K   Y   V   H   K   D   S   E   G   N   D   G   E

589  TTG TTT TGG GCT CAC ACT GGT GGA GGT GGA GGT AAC TTC GGT
      L   F   W   A   H   T   G   G   G   G   G   N   F   G

631  ATT ATC ACC AAA TAC TAC TTC AAG GAT TTG CCA ATG TCT CCA
      I   I   T   K   Y   Y   F   K   D   L   P   M   S   P

673  AGA GGT GTC ATC GCT TCT AAC TTA CAC TTC TCT TGG GAC GGT
      R   G   V   I   A   S   N   L   H   F   S   W   D   G

715  TTC ACT AGA GAT GCC TTG CAA GAT TTG TTG ACT AAG TAC TTC
      F   T   R   D   A   L   Q   D   L   L   T   K   Y   F

757  AAG TTG GCT AGA TGT GAT TGG AAG AAT ACT GTT GGT AAG TTC
      K   L   A   R   C   D   W   K   N   T   V   G   K   F
```

```
 799 CAA ATC TTC CAC CAA GCA GCT GAA GAG TTT GTT ATG TAC TTG
      Q   I   F   H   Q   A   A   E   E   F   V   M   Y   L

841 TAT ACA TCC TAC TCT AAC GAC GCC GAG AGA GAA GTT GCC CAA
      Y   T   S   Y   S   N   D   A   E   R   E   V   A   Q

883 GAC AGA CAC TAT CAT TTG GAG GCT GAC ATT GAA CAG ATC TAC
      D   R   H   Y   H   L   E   A   D   I   E   Q   I   Y

925 AAA ACA TGC GAG CCT ACC AAA GCT CTT GGT GGT CAT GCT GGT
      K   T   C   E   P   T   K   A   L   G   G   H   A   G

967 TGG GCT CCT TTC CCT GTT AGA CCT AGA AAG AGA CAC ACA TCC
      W   A   P   F   P   V   R   P   R   K   R   H   T   S

1009 AAG ACT TCT TAT ATG CAT GAC GAG ACT ATG GAC TAC CCT TTC
      K   T   S   Y   M   H   D   E   T   M   D   Y   P   F

1051 TAC GCT TTG ACT GAG ACT ATC AAC GGT TCC GGT CCT AAT CAG
      Y   A   L   T   E   T   I   N   G   S   G   P   N   Q

1093 AGA GGT AAG TAC AAG TCT GCT TAC ATG ATC AAG GAC TTT CCA
      R   G   K   Y   K   S   A   Y   M   I   K   D   F   P

1135 GAC TTC CAG ATT GAT GTT ATC TGG AAA TAC CTT ACT GAG GTT
      D   F   Q   I   D   V   I   W   K   Y   L   T   E   V

1177 CCT GAC GGT TTG ACT AGT GCC GAA ATG AAG GAT GCT CTT CTT
      P   D   G   L   T   S   A   E   M   K   D   A   L   L

1219 CAG GTT GAT ATG TTC GGT GGT GAG ATT CAC AAG GTT GTT TGG
      Q   V   D   M   F   G   G   E   I   H   K   V   V   W

1261 GAT GCT ACT GCA GTT GCT CAG AGA GAG TAC ATC ATC AAA CTG
      D   A   T   A   V   A   Q   R   E   Y   I   I   K   L

1303 CAG TAC CAG ACA TAC TGG CAG GAA GAA GAC AAG GAT GCA GTT
      Q   Y   Q   T   Y   W   Q   E   E   D   K   D   A   V

1345 AAC TTG AAG TGG ATT AGA GAC TTT TAC GAG GAG ATG TAT GAG
      N   L   K   W   I   R   D   F   Y   E   E   M   Y   E

1387 CCT TAT GGT GGT GTT CCA GAC CCT AAC ACT CAG GTT GAG AGT
      P   Y   G   G   V   P   D   P   N   T   Q   V   E   S

1429 GGT AAA GGT GTT TTT GAG GGA TGC TAC TTC AAC TAC CCT GAT
      G   K   G   V   F   E   G   C   Y   F   N   Y   P   D

1471 GTT GAC TTG AAC AAC TGG AAG AAC GGT AAG TAT GGT GCC TTG
      V   D   L   N   N   W   K   N   G   K   Y   G   A   L

1513 GAA CTT TAC TTT TTG GGT AAC CTG AAC AGA TTG ATC AAG GCC
      E   L   Y   F   L   G   N   L   N   R   L   I   K   A

1555 AAA TGG TTG TGG GAT CCT AAC GAG ATC TTC ACA AAC AAA CAG
      K   W   L   W   D   P   N   E   I   F   T   N   K   Q

1597 TCT ATC CCT ACT AAA CCT CTT AAG GAG CCT AAG CAG ACT AAA
      S   I   P   T   K   P   L   K   E   P   K   Q   T   K

1639 TAG TAG
```

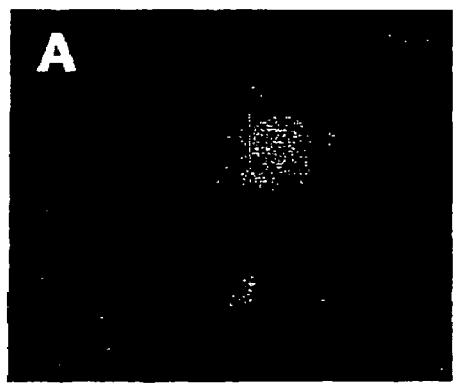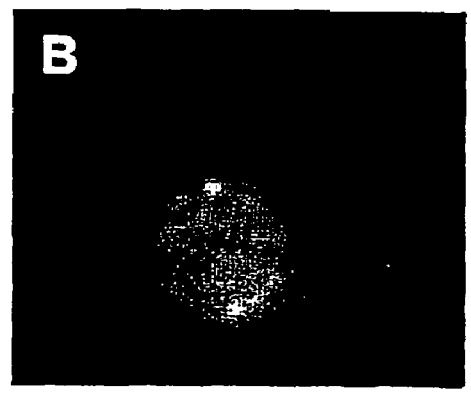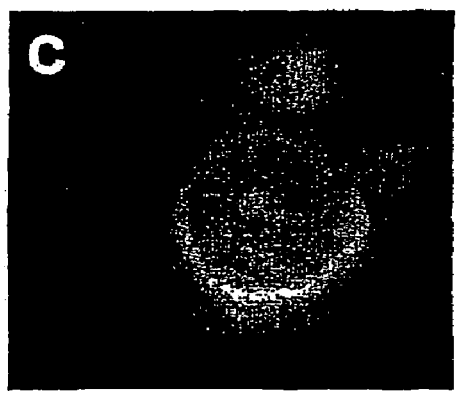
FIG. 7 western blot (WB 33)

colloidal coomassie (Coo 2)

western blot (WB 34)

collidal coomassie (Coo 3)

western blot (WB 35)

collidal coomassie (Coo 4)

α-1,4-Glucans in starch and glycogen    1,5-anhydro-D-fructose

FIGURE 17C

| Blot C | |
|---|---|
| M 1 2 3 4 5 6 7 8 9 10 11 12 13 14 15 16 17 | 220K<br>97.4K<br>66K<br>46K<br>30K<br>21.5K<br>14.3K |

FIGURE 20
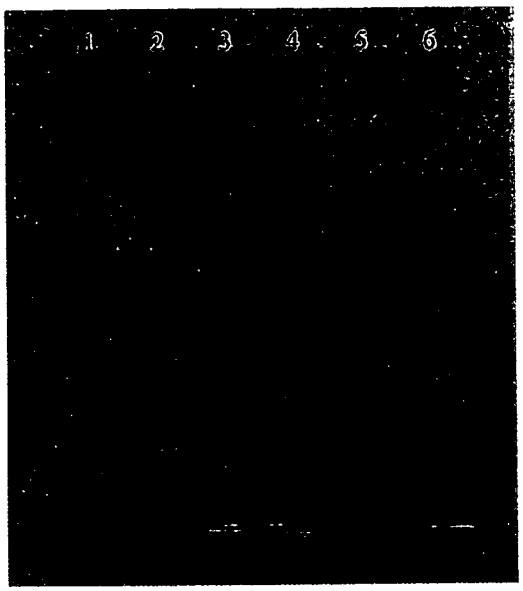
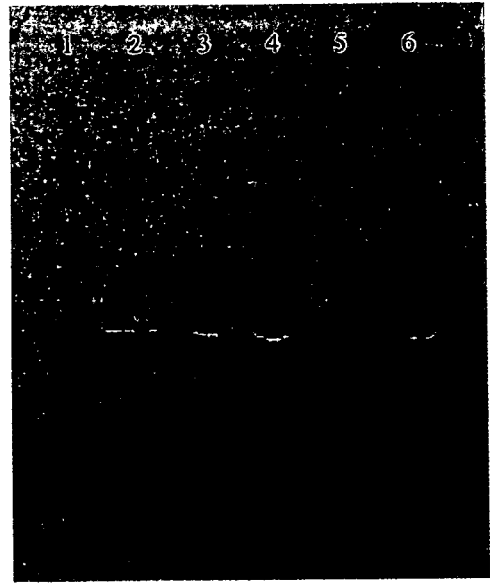

METHOD OF EXTRACTING RECOMBINANT HEXOSE OXIDASE

This application is a continuation-in-part of U.S. application Ser. No. 09/722,938 filed Nov. 27, 2000, which is a continuation of International Application No. PCT/IB00/01886, filed Nov. 24, 2000, designating the US, and published as WO 01/38544 on May 31, 2001 (inventors: JOHANSEN, KJAERULFF, MADRID, PEDERSEN, POULSEN, ZARGAHI); which claims priority from Great Britain Application no. 9927801.2, filed Nov. 24, 1999. Each of the foregoing applications, patents and publications and all documents cited or referenced therein ("application cited documents") and all documents cited or referenced in this specification ("herein cited documents") and all documents referenced or cited in herein cited documents and in application cited documents, including during the prosecution of any of the application cited documents, are hereby incorporated by reference.

FIELD OF THE INVENTION

The present invention relates to a method for releasing an intracellular protein of interest (POI).

In particular, the present invention relates to a method for releasing a soluble or membrane associated intracellular protein of interest (POI) using a membrane extracting composition which assists in the release of the POI.

BACKGROUND OF THE INVENTION

The traditional way for recovering an intracellular POI, such as an enzyme, has been to use a mechanical disruption method (Naglak et al 1990) such as a bead mill or a cell homogenizer operating with a french press principle. However, these mechanical disruption methods suffer from the disadvantage that they are energy consuming methods with a low capacity and the cell homogenizers or similar equipment required for mechanical disruption are expensive to purchase. In addition, mechanical methods expose the cells, and hence the extracted POI to very harsh conditions, especially as most proteins will be denatured by the heat generated unless the mechanical device and/or homogenate is efficiently cooled.

Furthermore, some cells, such as yeast cells (such as those from *Hansenula*) are difficult to disrupt mechanically and more than one passage through a cell homogenizer is needed. The cell homogenate may also contain cell wall fragments and DNA, which results in a high viscosity. This means that the separation of cell debris from the POI can prove to be a difficult operation. In addition, the resulting cell free homogenate may contain not only the intracellular POI but also a large number (sometimes several thousand) of different intracellular proteins and enzymes associated with the general cell metabolism. This means that the resultant cell free homogenate may be not only difficult to concentrate by ultrafiltration but may also provide problems with respect to obtaining the right commercial concentration of a given POI.

In order to minimise the potential detrimental effect of some mechanical disruption methods, chemical methods using, for example, detergents have been developed to permeabilize yeast cells. By way of example, the non-ionic detergent, polyethoxylated octylphenols, commercially available as Triton X-100, has been used either alone or in combination with freeze thaw cycles (referenced in Naglak et al 1990). In addition, U.S. Pat. No. 5,124,256 (Crahay et al 1992) discloses a method whereby proteins were extracted from *Saccharomyces* yeast by means of treating the yeasts in an aqueous medium with a neutral water-soluble mineral salt and a non-ionic water-soluble polyethoxylated alkylphenol surfactant having a Hydrophilic Lipophilic Balance (HLB) of between 8 and 15.

However, these non-ionic water-soluble polyethoxylated alkylphenol surfactants which include polyethoxylated octylphenols, nonylphenols and tributylphenols, (particularly those commercially available under the trade marks TritonX-100, Nonidet P-40 and Sapogenat T-080) suffer from the drawbacks that (i) they may not have a significant extracting effect when used alone and (ii) these surfactants can interfere with subsequent measurements of the enzymatic activity of the POI.

Several organic solvents have also been used to both permeabilize yeast cells in in situ enzymatic assays and for removing proteins from yeast cells. Examples of such solvents include but are not limited to toluene, ethyl acetate, dimethyl sulfoxide, and benzene combined with glycerol (Naglak et al 1990). However, these solvents are unattractive to use in industrial scale production when fermentor volumes of up to 200 $m^3$ are required.

Digitonin and other naturally occuring saponins have also been shown to permeabilize a number of eukaryotic cells (see Joshi et al 1989). Although the exact mechanism of digitonin permeabilization is not known, it is believed that digitonin forms a complex with the cholesterol present in the cell membrane and renders the membrane leaky. Digitonin permeabilization of yeast cells may also be due to the complexing of ergosterols of the yeast membrane. Joshi et al (1989) used digitonin (0.1%) to permeabilize the yeast *Kluyveromyces* which facilitated the intracellular catalysis of lactose to glucose and galactose. The non-ionic detergent saponin, from Quillaja Bark, is another cholesterol complexing agent, which is known to permeabilise at least mammalian cells (Naglak et al 1990). Again, like the non-ionic detergents as outlined above, the use of digitonin and other naturally occuring saponins may suffer from the drawback that when used alone, they may not have a significant extracting effect.

U.S. Pat. No. 5,240,834 (Frankel et al) describes a protein extraction using the detergent Sarkosyl (N-lauryl sarcosine), see Example 1 (paragraphs 3 to 4) as well as lines 67 of column 3 to line 2 of column 4. U.S. Pat. No. 6,251,626 (Stougaard et al) describes extraction of HOX from yeast or bacterial cells, but the protein is released by mechanical disruption in a French press. The yeast cells are exposed to enormous pressure (to 20,000 p.s.i.) in order to disrupt them and to release the recombinant HOX enzyme (lines 25 to 31 of column 40).

Chaotropic agents have also been used to faciliate the extraction of intracellular enzymes. By way of example, U.S. Pat. No. 3,801,461 (Miyake and Shiosaka 1974) discloses a process for extracting intracellular enzymes produced in the mycelia or cells of fungi or bacteria using a chaotrophic solution such as a urea solution. U.S. Pat. No. 4,683,293 (Craig 1987) also discloses a method for selective extraction of lipophilic proteins from transformed cells of the genus *Pichia* by cell lysis in the presence of chaotrophic salts such as sodium thiocyanate, sodium iodide, sodium hypochlorite, lithium bromide, guanidium hydrochloride and urea. However, chaotrophic agents suffer from the disadvantage that exposure of the POI to a chaotrophic agent, such as urea can result in an actual loss of enzyme activity through denaturation of the POI.

In addition to the drawbacks cited above, the above cited prior art only relates to the permeabilisation of host cells to low molecular weight molecules while the POI remains unchanged within the cell. In particular, none of the above cited prior art relates to the extraction of a membrane associated intracellular POI under conditions which do not affect the nature and/or activity of the POI. More in particular, none of the above cited prior art relates to a method for assisting in the release of a membrane associated intracellular POI which is trapped and is incapable of being secreted from a host cell.

The present invention thus seeks to overcome the problems associated with the extraction methods of the prior art.

The present invention thus provides a method for releasing a soluble or membrane associated intracellular protein of interest (POI) from a host organism.

SUMMARY OF THE INVENTION

The present invention relates to a method for assisting in the release of a soluble or membrane associated intracellular POI which is trapped and/or is incapable of being secreted from a host cell. The extraction of an intracellular POI using the method of the present invention was compared with a traditional cell disruption method and with extraction procedures using other ionic/non ionic detergents and emulsifiers. Combinations of detergents with protease and salts were also investigated. The results of the present invention indicate that the extraction of a soluble or membrane associated intracellular POI using the method of the present invention is advantageous because:

(i) traditional cell disruption techniques can be avoided;

(ii) the intracellular POI may be recovered free from contaminating DNA and cell wall fragments;

(iii) the intracellular POI may be recovered from a eukaryotic host organism, such as yeast, before glycosylation takes place. Overglycosylation of secreted proteins is a well known problem especially in eukaryotic host organisms such as yeast. This drawback associated with yeast expression systems has led to a reluctance to use yeast as a production system even though yeast expression vectors are capable of producing proteins at high levels of expression with a large amounts of biomass, and additionally, yeast has approved use in food. By expressing the POI intracellularly and then extracting the POI with the method of the present invention, the POI will be non-glycosylated, because the POI has not passed through the secretion pathway where glycosylation takes place;

(iv) the fermentation procedure that precedes the method of the present invention can be carried out at any pH that is suitable for the host cell. It is well known in the art that a secreted POI may be affected by the pH of its extracellular growth medium. Up until now, it was often necessary to maintain the pH of a host organism growth medium at an approximately neutral pH because fermentations at such a pH were deemed necessary to maintain the stability of a secreted POI even though they usually increased the risk of bacterial contamination. With the method of the present invention, the POI is not secreted. Thus, the pH of the host organism growth medium is irrelevant as the intracellular pH remains constant irrespective of the media pH. Accordingly, the present invention permits the growth of a host organism (such as yeast) at a lower pH (such as pH 4.0) which reduces the risk of bacterial contamination without affecting either biomass or POI production; and (v) the method of the present invention can be used to prevent contact of the intracellular POI with the extracellular growth medium. This is advantageous if the POI is unstable in the extracellular media, because of, for example, protease sensitivity. By expressing the protein intracellularly and then extracting with the method of the present invention contact with the extracellular media is avoided.

Summary Aspects of the Invention

In one broad aspect, the present invention relates to a method for releasing a protein of interest (POI) from a cell. The method comprises the steps of: providing a cell comprising a soluble or membrane associated intracellular POI; contacting the cell with a membrane extracting composition, preferably comprising a quaternary ammonium compound; and causing the POI to be released from the cell under conditions sufficient for the release of the POI and in a soluble form.

We show that the method described here is of general utility, and may be used to release a number of proteins. In particular, the POI may be an hexose oxidase (D-hexose: $O_2$-oxidoreductase, EC 1.1.3.5). The POI may be an IL1-ra protein. The POI may comprise a glucan lyase protein. Accordingly, the POI may be an intracellular protein of interest.

Detailed Aspects of the Invention

According to a first aspect of the present invention, we provide a method for releasing a soluble or membrane associated intracellular protein of interest (POI) from a cell comprising the steps of: (a) providing a cell comprising a soluble or membrane associated intracellular POI; (b) contacting the cell with a membrane extracting composition comprising a quaternary ammonium compound; and (c) causing the POI to be released from the cell under conditions sufficient for the specific release of the POI and in a soluble form.

The quaternary ammonium compound is preferably selected from the group consisting of Lauroyl Trimethyl Ammonium Bromide (LTAB), Myristyl Trimethyl Ammonium Chloride (MTAC), Cetyl Trimethyl Ammonium Chloride (CTAC), Cetrimide, Cetyl Trimethyl Ammonium Bromide (CTAB), Stearoyl Trimethyl Ammonium Chloride (STAC), Stearoyl Trimethyl Ammonium Bromide (STAB), Benzalkonium Chloride (alkyldimethylbenzylammonium chloride), N-Cetylpyridinium Bromide (N-Hexadecylpyridinium bromide), N-Cetylpyridinium Chloride (N-Hexadecylpyridinium chloride), Benzyl Dimethyl Tetradecyl Ammonium Chloride, Benzyl Dimethyl Hexadecyl Ammonium Chloride and a combination of any two or more thereof.

The membrane extracting composition may in particular comprise from about 0.05% to about 0.6% by weight of the quaternary ammonium compound, preferably from about 0.1% to about 0.5% by weight of the quaternary ammonium compound, preferably from about 0.2% to about 0.45% by weight of the quaternary ammonium compound, more preferably about 0.4% by weight of the quaternary ammonium compound.

Preferably, the cell is contacted with the membrane extracting composition at temperatures from about 4° C. to 40° C., preferably from about 20° C. to about 30° C., more preferably about 25° C.

The cell may be contacted with the membrane extracting composition at a pH optima of from about 2.0 to about 11.0 (more especially from about to 5.0 to about 7.0, more especially about 6.3).

Preferably, the cell is selected from the group consisting of yeast cells, fungal cells and bacterial cells, preferably from yeast and fungal cells.

In preferred embodiments, the cell is a transformed cell. Furthermore, the cell may be transformed with a nucleic acid encoding the POI. Preferably, the intracellular POI is produced by recombinant DNA techniques.

In one embodiment, the POI is an IL-1ra enzyme.

In another embodiment, the POI is a glucan lyase enayme. In preferred embodiments, the yield of glucan lyase is 1 g/liter or more. In highly preferred embodiments, the yield of glucan lyase is 3.5g/liter or more.

In a further embodiment, the POI is a HOX enzyme. The HOX enzyme may comprise the amino acid sequence set out in SEQ ID No 22 or a variant, homologue, derivative or fragment thereof. Preferably, the HOX enzyme is encoded by a nucleotide sequence set out in SEQ ID No 22 or a variant, homologue, derivative or fragment thereof.

Preferably, the HOX enzyme is encoded by a nucleotide sequence capable of hybridising to the nucleotide sequence set out in SEQ ID No 22 or a variant, homologue, derivative or fragment thereof or a sequence complementary to the hybridisable sequence.

There is provided, according to a second aspect of the present invention, method for screening for mutated cells or transformed cells producing elevated levels of a soluble or membrane associated intracellular POI comprising the steps of: (a) growing the mutated cells at 30° C.; (b) incubating the mutated cells or transformed cells with the membrane extracting composition comprising a quarternary ammonium compound; (c) recovering the cell free medium; (d) screening the cell free medium for elevated levels of the intracellular POI; such that the presence of the intracellular POI in the cell free medium is indicative that the intracellular POI has been released.

We provide, according to a third aspect of the present invention, a membrane extracting composition suitable for specifically releasing a soluble or membrane associated intracellular POI, in which the composition is contacted with the cell under the following conditions: (a) a percentage by weight of quarternary ammonium compound from about 0.05% to about 0.6% (more especially from about 0.1% to about 0.5%, more especially from about 0.2% to about 0.45%, more especially about 0.4%); (b) a pH optima of from about 2.0 to about 11.0 (more especially from about to 5.0 to about 7.0, more especially about 6.3); (c) a temperature optima of from about 4° C. to about 40° C., (more especially from about 20° C. to about 30° C., more especially about 25° C.); such that the intracellular POI substantially free of contaminating proteins is obtained.

As a fourth aspect of the present invention, there is provided use of a membrane extracting composition comprising a quarternary ammonium compound to selectively release a soluble or membrane associated intracellular POI.

We provide, according to a fifth aspect of the present invention, a HOX enzyme producible by a method as specified, in which the HOX enzyme is encoded by a nucleotide sequence as defined above, in which the nucleotide sequence is synthesised by the oligonucleotides as set out in SEQ ID Nos 2-22.

Preferably, the POI is released in a substantially non-glycoslyated form from a eukaryotic host organism The present invention, in a sixth aspect, provides a substantially non-glycosylated POI released from a eukaryotic host organism. Preferably, the POI is released by a method according to a first aspect of the invention.

We further describe a method for releasing a soluble or membrane associated intracellular protein of interest (POI) from a transformed cell comprising the steps of: providing a transformed cell comprising an soluble or membrane associated intracellular POI; contacting the transformed cell with a membrane extracting composition; and causing the POI to be released from the transformed cell under conditions sufficient for the specific release of the POI and in a soluble form.

We also describe a method for releasing a HOX enzyme from a transformed cell comprising the steps of: providing a transformed cell comprising a HOX enzyme; contacting the transformed cell with a membrane extracting composition; and causing the HOX enzyme to be released from the transformed cell under conditions sufficient for the specific release of the a HOX enzyme and in a soluble form.

We also describe a method for releasing an interleukin 1 receptor antagonist (IL-1ra) from a transformed cell comprising the steps of: providing a transformed cell comprising a IL-1ra; contacting the transformed cell with a membrane extracting composition; and causing the IL-1ra to be released from the transformed cell under conditions sufficient for the specific release of the IL-1ra and in a soluble form.

We also describe a method for screening for mutants producing elevated levels of a soluble or membrane associated intracellular POI comprising the steps of: growing the mutated cells at 30° C.; incubating the mutated cells with the membrane extracting composition; recovering the cell free medium; screening the cell free medium for elevated levels of the intracellular POI; such that the presence of the intracellular POI cell free medium is indicative that the intracellular POI has been released.

We also describe a membrane extracting composition suitable for releasing a soluble or membrane associated intracellular POI wherein the composition is contacted with the cell under the following conditions of: a percentage by weight of quarternary ammonium compound from about 0.05% to about 0.6% (more especially from about 0.1% to about 0.5%, more especially from about 0.2% to about 0.45%, more especially about 0.4%); and a pH optima of from about 2.0 to about 11.0 (more especially from about 5.0 to about 7.0, more especially about 6.3); a temperature optima of from about 4° C. to about 40° C., (more especially from about 20° C. to about 30° C., more especially about 25° C.).

We also describe a membrane extracting composition comprising a quarternary ammonium compound suitable for releasing a soluble or membrane associated intracellular POI.

Other aspects and advantages of the present invention are presented in the accompanying claims and in the following description and discussion. These aspects are presented under separate section headings. However, it is to be understood that the teachings under each section heading are not necessarily limited to that particular section heading.

DETAILED DESCRIPTION OF THE INVENTION

The present invention demonstrates the highly surprising finding that a membrane extraction composition comprising quaternary ammonium compounds may be used to obtain a fast, specific and economically efficient extraction of a soluble or membrane associated intracellular POI, without resorting to the use of traditional cell disruption techniques. Advantageously and unexpectedly, the resulting cell extract contains very little contaminating intracellular DNA and is relatively free of cell wall fragments thereby simplifying any further purification steps to which the POI may be subjected. This is in contradistinction to the prior art mechanical extraction methods.

Intracellular Protein

As used herein, the term "intracellular" POI means a POI which is found within or inside a cell or cells. The intracellular POI may be localised within a cell (such as in the cytoplasm of the cell) even though it has a signal secretory mechanism. In this regard, the intracellular POI may be a POI which is not actively secreted from a cell or is incapable of being secreted by the cell even though it has a signal sequence secretory mechanism. In the alternative, the intracellular POI may be a naturally secreted POI which has been engineered to prevent its secretion from a cell. Alternatively, the POI may be a chimeric protein comprising a membrane binding domain.

The method of the present invention is in contrast to the method described in Ahlstrom and Edebo ((1994) FEMS Microbiology Letters 1197-12) who report on the release of the periplasmic β-lactamase from *E. coli* with tetradecyl betainate. The periplasm is the region in a bacterial cell between the cell membrane and the cell wall. Thus, the periplasmic β-lactamase from *E. Coli* is localised outside the cell membrane and is not a cytoplasmic enzyme. In contradistinction, the POI of the present invention is an intracellular POI which is found within or inside a cell or cells.

Membrane Associated POI

As used herein, the term "membrane associated POI" means a POI which may be localised in the proximity of, but may not be substantially associated with a cell or plasma membrane. Thus, the membrane associated enzyme is not a substantially membrane bound protein or the membrane associated enzyme is not substantially bound to a cell membrane. The membrane associated POI may be solubilised by a mechanical treatment with a cell homogeniser.

Membrane Bound POI

As used herein, the term "membrane bound POI" means a protein which is not rendered soluble by mechanical treatment with a cell homogeniser.

Specific Release

The term "specific release" means that the specific activity of the POI is higher than when it has been extracted by mechanical means—such as by use of a bead mill or a cell homogenizer operating with a french press principle.

Transformed Cell

The term "transformed cell" includes cells that have been transformed by use of recombinant DNA techniques. The transformation typically occurs by insertion of one or more nucleotide sequences into a cell that is to be transformed. The inserted nucleotide sequence may be a heterologous nucleotide sequence (i.e. is a sequence that is not natural to the cell that is to be transformed. In addition, or in the alternative, the inserted nucleotide sequence may be an homologous nucleotide sequence (i.e. is a sequence that is natural to the cell that is to be transformed)—so that the cell receives one or more extra copies of a nucleotide sequence already present in it.

Membrane Extracting Composition

As used herein, the term "membrane extracting composition" means a composition capable of affecting components in a cellular membrane such that a membrane bound and/or membrane associated intracellular POI is sufficiently dissociated and/or released from the membrane component and the POI is easily recovered and/or harvested from the membrane extracting composition. The POI may also be a soluble POI. In a highly preferred embodiment, the membrane extracting composition of the present invention comprises one or more quaternary ammonium compounds or combinations thereof.

Quarternary Ammonium Compounds

As used herein, the term "quarternary ammonium compound" means a compound derivable from ammonium hydroxide or an ammonium salt by replacement of all four hydrogen atoms of the $NH_4^+$ ion by organic groups which may be the same or different. Typically one of the organic groups is a long chain ($C_8$-$C_{18}$)alkyl group and the other three are shorter chain alkyl or other groups.

In a preferred embodiment, these compounds have the structure:

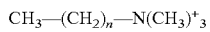

where n is the number of methylene groups in the chain and where the counter ion may be a halogen such as a chloride or bromide ion. These compounds have the properties of cationic detergents and are powerful antimicrobial agents.

Examples of these quarternary ammonium compound include but is not limited to Lauroyl Trimethyl Ammonium Bromide (LTAB), Myristyl Trimethyl Ammonium Chloride (MTAC), Cetyl Trimethyl Ammonium Chloride (CTAC), Cetyl Trimethyl Ammonium Bromide (CTAB), Cetrimide (or Cetrimidum which comprises a mixture of alkylammonium bromides, principally CTAB), Stearoyl Trimethyl Ammonium Chloride (STAC), Stearoyl Trimethyl Ammonium Bromide (STAB), Benzalkonium Chloride (alkyldimethylbenzylammonium chloride), N-Cetylpyridinium Bromide (N-Hexadecylpyridinium bromide), N-Cetylpyridinium Chloride (N-Hexadecylpyridinium chloride), Benzyl Dimethyl Tetradecyl Ammonium Chloride, and Benzyl Dimethyl Hexadecyl Ammonium Chloride.

By way of example, the structure of some of these compounds is illustrated as follows.

The compounds are listed in the order of increasing methylene groups:

Preferably the quaternary ammonium compound is cetylpyridinium chloride (CPC, $C_{21}H_{38}NCl$). The structure of CPC is illustrated as follows:

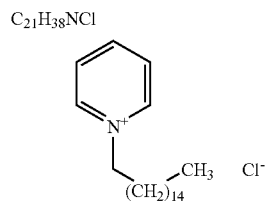

Preferably the quaternary ammonium compound is cetylpyridinium bromide (CPB, $C_{21}H_{38}NBr$). The structure of CPB is illustrated as follows:

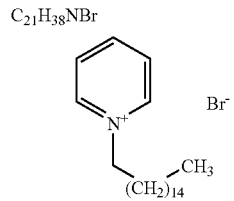

Preferably the quaternary ammonium compound is Benzyl Dimethyl Tetradecyl Ammonium Chloride (BDTAC: $C_{23}H_{42}NCl$). The structure of BDTAC is illustrated as follows:

$C_{23}H_{42}NCl$

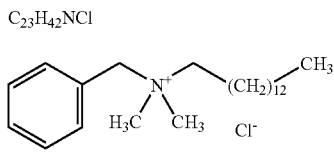

Preferably the quaternary ammonium compound is Benzyl Dimethyl Hexadecyl Ammonium Chloride (BDHAC: $C_{25}H_{46}NCl$). The structure of BDHAC is illustrated as follows:

$C_{25}H_{46}NCl$ $C_{23}H_{42}NCl$

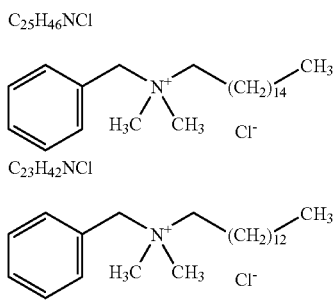

Preferably the quaternary ammonium compound is benzalkonium chloride (alkyldimethylbenzylammonium chloride).

The structure of benzalkonium chloride is illustrated as follows:

$C_{12}H_{25}N(CH_3)_2C_7H_7Cl$

A comparison of the structure of CTAB and benzalkonium chloride (also known as Alkyldimethylbenzylammonium chloride—hereinafter referred to under the proprietary name of Rodalon) is illustrated as follows:

Rodalon:

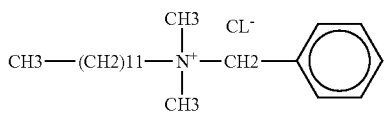

CTAB:

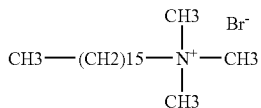

Preferably the quaternary ammonium compound is Lauroyl Trimethyl Ammonium Bromide (LTAB).

Preferably the quaternary ammonium compound is Cetyl Trimethyl Ammonium Chloride (CTAC).

Preferably the quaternary ammonium compound is Cetyl Trimethyl Ammonium Bromide (CTAB).

The cationic detergent CTAB has been shown to be capable of altering yeast permeability, probably by causing the formation of transmembrane pores, similar to the suggested mechanism for two other non-ionic detergents such as Pluronic F-68 and Triton X-100 (King et al 1991). The alteration of cellular permeability using detergents such as CTAB has facilitated the measurement of intracellular enzyme activities in whole cells (Sekhar et al 1999). Moreover, the development of CTAB permeabilised cells has proved useful for intracellular enzyme catalysis in, for example, cells from yeast strains such as *Saccharomyces cerevisiae* (Gowda et al 1991) and *Kluyveromyces fragilis* (Joshi et al 1987). In these studies, it is important to note that the detergent CTAB made yeast cells permeable to low molecular weight molecules (such as substrates, products, cofactors), while intracellular enzymes and other POIs remained unchanged within the cell. In contradistinction to the present invention, none of the above mentioned studies has disclosed or suggested that the detergent CTAB (or related quarternary ammonium compounds such as LTAB or CTAC) may be used to assist in the release of a soluble or membrane associated intracellular POI from a host cell.

The cationic detergent CTAB has also been commonly used in methods for isolating DNA/RNA molecules. By way of example, DNA molecules may be isolated by treating cells with CTAB at high temperatures (about 65° C.) and a low salt concentrations (less than 0.6M NaCl) such that a DNA-CTAB precipitate is formed and easily recovered. The CTAB detergent is also frequently used to extract nucleic acids from plants where coprecipitation of neutral polysaccharides, by either ethanol or isopropanol, may pose a major problem. CTAB has also been used in the direct lysis and precipitation of the DNA from the supernatant of *E. coli* cultures infected with filamentous phage (see Ishaq et al 1990 Biotechniques 9(1): 19-20, 22, 24; Kambouris et al 1999: FEMS Iumunol Med Microbiol 25(3): 255-64; Kuipers et al 1999 Ann Rheum Dis 58(2): 103-8; Velegraki et al 1999 Med Mycol 37(1) 69-73; White et al 1998 Med Mycol 36(5): 299-303; Woodhead et al 1998 Mol Biotechnol 9(3): 243-6; Mito and Detschart 1998 Parasitol Res 84(7) 596-7; Zhang et al 191998) J Virol Methods 71(1) 45-50; Reineke et al (1998) Insect Mol Biol 7(1) 95-9). All of these CTAB based methods for the isolation of DNA molecules rely on the exploitation of the properties of CTAB to precipitate nucleic acids and acid polysaccharides while maintaining the remaining proteins and neutral polysaccharides in solution. Surprisingly and unexpectedly, the method of the present invention facilitates not only the precipitation but also the retention of intracellular DNA. Consequently, the method of the present invention facilitates the selective release of an intracellular POI.

Releasing

According to the method of the present invention, the soluble or membrane associated intracellular POI is released from a host cell or cells by contacting the cells with a membrane extracting composition under conditions sufficient for the release of the intracellular POI.

Preferable Conditions for Releasing the POI (I) % Quaternary Ammonium Compound

Preferably the membrane extracting composition comprises from about 0.05% to about 0.6% by weight of a quaternary ammonium compound, preferably from about 0.1% to about 0.5% by weight of a quaternary ammonium compound, preferably from about 0.2% to about 0.45% by weight of a quaternary ammonium compound, more preferably about 0.4% by weight of a quaternary ammonium compound.

Preferably the quaternary ammonium compound is LTAB.

Preferably the quaternary ammonium compound is CTAC.

Preferably the quaternary ammonium compound is CTAB.

Preferably the quaternary ammonium compound is Benzalkonium Chloride ($C_{12}H_{25}N(CH_3)_2C_7H_7Cl$).

Preferably the quaternary ammonium compound is Cetylpyridinium Chloride (CPC, $C_{21}H_{38}NCl$).

Preferably the quaternary ammonium compound is Cetylpyridinium Bromide (CPB, $C_{21}H_{38}NBr$).

Preferably the quaternary ammonium compound is Benzyl Dimethyl Tetradecyl Ammonium Chloride (BDTAC: $C_{23}H_{42}NCl$).

Preferably the quaternary ammonium compound is Benzyl Dimethyl Hexadecyl Ammonium Chloride (BDTAC: $C_{25}H_{46}NCl$).

(II) Temperature

Preferably the host cell is contacted with the membrane extracting composition at temperatures from about 4° C. to about 40° C.

Preferably the host cell is contacted with the membrane extracting composition at temperatures from about 20° C. to about 30° C.

Preferably the host cell is contacted with the membrane extracting composition at temperatures of about 25° C.

Preferably the above temperature ranges are higher if the POI is a thermostable POI.

(III) pH

Preferably the host cell is contacted with the membrane extracting composition at a pH of from about 2.0 to about 11.0.

Preferably the host cell is contacted with the membrane extracting composition at a pH of from about 5.0 to about 7.0.

Preferably the host cell is contacted with the membrane extracting composition at a pH of about 6.3.

It is highly advantageous that the fermentation procedure that precedes the method of the present invention can be carried out at any pH that is suitable for the host cell. It is well known in the art that a secreted POI may be affected by the pH of its extracellular growth medium. Up until now, it was often necessary to maintain the pH of a host organism growth medium at an approximately neutral pH because fermentations at such a pH were deemed necessary to maintain the stability of a secreted POI even though they usually increased the risk of bacterial contamination. With the method of the present invention, the POI is not secreted. Thus, the pH of the host organism growth medium is irrelevant as the intracellular pH remains constant irrespective of the media pH. Accordingly, the present invention permits the growth of a host organism (such as yeast) at a lower pH (such as pH 4.0) which reduces the risk of bacterial contamination without affecting either biomass or POI production.

A further advantage of the method of the present invention is that it can be used to prevent contact of the intracellular POI with the extracellular growth medium. This is advantageous if the POI is unstable in the extracellular media, because of, for example, protease sensitivity. By expressing the protein intracellularly and then extracting with the method of the present invention contact with the extracellular media is avoided.

POI Recovery

The intracellular POI which has been extracted in accordance with the method of the present invention may be further treated by employing techniques known by those of skill in the art to further concentrate and purify the POI. Thus, the extracted intracellular POI may be concentrated by for example, ultrafiltration, passage through a reverse phase resin followed by elution with a minimum volume of solvent, precipitation, ultrafiltration and lyophilization. Techniques available for further purification of the POI include but are not limited to size fractionation employing size exclusion resins, high performance liquid chromatography, ion exchange and hydrophobic chromatography.

POI

As used herein, the term "POI" includes but is not limited to, a protein, polypeptide or peptide including, but not limited to, a structural protein, an enzyme, a cytokine (such as an interferon and/or an interleukin), an interleukin receptor antagonist (such as IL-1ra), an antibiotic, a polyclonal or monoclonal antibody, or an effective part thereof, such as an Fv fragment, which antibody or part thereof may be natural, synthetic or humanized, a peptide hormone, an antigen (such as a bacterial/viral/protozoal/parasitic antigen), a tumour antigen, a receptor, a ligand, a regulatory factor, a signalling molecule, a neurotransmitter, a clotting factor, or any other protein including but not limited to a membrane bound protein and/or a membrane associated protein.

In the method of the present invention, the POI is expressed intracellularly, that is, it is an intracellular POI.

The POI may be produced by recombinant DNA techniques using a nucleotide sequence of interest (NOI).

NOI

As used herein, the term "NOI" is defined to encompass DNA and RNA of both synthetic and natural origin which DNA or RNA may contain modified or unmodified deoxy- or dideoxy-nucleotides or ribonucleotides or analogs thereof. The nucleic acid may exist as single- or double-stranded DNA or RNA, an RNA/DNA heteroduplex or an RNA/DNA copolymer, wherein the term "copolymer" refers to a single nucleic acid strand that comprises both ribonucleotides and deoxyribonucleotides. The NOI may even be codon optimised to further increase expression.

Synthetic

The term "synthetic", as used herein, is defined as that which is produced by in vitro chemical or enzymatic synthesis. It includes but is not limited to NOIs made with optimal codon usage for host organisms such as the the methylotrophic yeasts *Pichia* and *Hansenula*.

Constructs

The NOI may be operatively linked to transcriptional and translational regulatory elements active in a host cell of interest. The NOI may also encode a fusion protein comprising signal sequences such as, for example, those derived from the glucoamylase gene from *Schwanniomyces occidentalis*, α-factor mating type gene from *Saccharomyces cerevisiae* and the TAKA-amylase from *Aspergillus oryzae*. Alternatively, the NOI may encode a fusion protein comprising a membrane binding domain.

Expression Vector

The NOI may be expressed at the desired levels in a host organism using an expression vector.

An expression vector comprising the NOI according to the present invention can be any vector which is capable of expressing the gene encoding the NOI in the selected host organism, and the choice of vector will depend on the host cell into which it is to be introduced. Thus, the vector can be an autonomously replicating vector, i.e. a vector that exists as an episomal entity, the replication of which is independent of chromosomal replication, such as, for example, a plasmid, a bacteriophage or an episomal element, a minichromosome or an artificial chromosome. Alternatively, the vector according to the invention is one which, when introduced into a host cell, is integrated into the host cell genome and replicated together with the chromosome.

Components of the Expression Vector

The expression vector typically includes the components of a cloning vector, such as, for example, an element that permits autonomous replication of the vector in the selected host organism and one or more phenotypically detectable markers for selection purposes. The expression vector normally comprises control nucleotide sequences encoding a promoter, operator, ribosome binding site, translation initiation signal and optionally, a repressor gene or one or more activator genes. Additionally, the expression vector may comprise a sequence coding for an amino acid sequence capable of targeting the POI to a host cell organelle such as a peroxisome or to a particular host cell compartment. Such a targeting sequence includes but is not limited to the sequence SKL. In the present context, the term "expression signal" includes any of the above control sequences, repressor or activator sequences. For expression under the direction of control sequences, the NOI encoding the POI is operably linked to the control sequences in proper manner with respect to expression.

Promoter

In the vector, the NOI encoding for the POI is operably combined with a suitable promoter sequence. The promoter can be any DNA sequence having transcription activity in the host organism of choice and can be derived from genes that are homologous or heterologous to the host organism.

Bacterial Promoters

Examples of suitable promoters for directing the transcription of the modified nucleotide sequence of the invention in a bacterial host include the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase gene (amyQ), the promoters of the *Bacillus subtilis* xylA and xylB genes and a promoter derived from a *Lactococcus* sp.-derived promoter including the P170 promoter. When the gene encoding the POI of the present invention is expressed in a bacterial species such as *E. coli*, a suitable promoter can be selected, for example, from a bacteriophage promoter including a T7 promoter and a phage lambda promoter.

Fungal Promoters

For transcription in a fungal species, examples of useful promoters are those derived from the genes encoding the, *Aspergillus oryzae* TAKA amylase, *Rhizomucor miehei* aspartic proteinase, *Aspergillus niger* neutral α-amylase, *A. niger* acid stable α-amylase, *A. niger* glucoamylase, *Rhizomucor miehei* lipase, *Aspergillus oryzae* alkaline protease, *Aspergillus oryzae* triose phosphate isomerase or *Aspergillus nidulans* acetamidase.

Yeast Promoters

Examples of suitable promoters for the expression in a yeast species include but are not limited to the Gal 1 and Gal 10 promoters of *Saccharomyces cerevisiae* and the *Pichia pastoris* AOX1 or AOX2 promoters.

Host Organisms (I) Bacterial Host Organisms

Examples of suitable bacterial host organisms are gram positive bacterial species such as Bacillaceae including *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus lautus, Bacillus megaterium* and *Bacillus thuringiensis*, *Streptomyces* species such as *Streptomyces murinus*, lactic acid bacterial species including *Lactococcus* spp. such as *Lactococcus lactis, Lactobacillus* spp. including *Lactobacillus reuteri, Leuconostoc* spp., *Pediococcus* spp. and *Streptococcus* spp. Alternatively, strains of a gram-negative bacterial species belonging to Enterobacteriaceae including *E. coli*, or to Pseudomonadaceae can be selected as the host organism.

(II) Yeast Host Organisms

A suitable yeast host organism can be selected from the biotechnologically relevant yeasts species such as but not limited to yeast species such as *Pichia* sp., *Hansenula* sp or *Kluyveromyces, Yarrowinia* species or a species of *Saccharomyces* including *Saccharomyces cerevisiae* or a species belonging to *Schizosaccharomyce* such as, for example, *S. Pombe* species.

Preferably a strain of the methylotrophic yeast species *Pichia pastoris* is used as the host organism.

Preferably the host organism is a *Hansenula* species.

It is highly advantageous to use the method of the present invention to recover an intracellular POI from a eukaryotic host organism, such as yeast, before glycosylation takes place. Overglycosylation of secreted proteins is a well known problem especially in eukaryotic host organisms such as yeast. This drawback associated with yeast expression systems has led to a reluctance to use yeast as a production system even though yeast expression vectors are capable of producing proteins at high levels of expression with a large amounts of biomass, and additionally, yeast has approved use in food. By expressing the POI intracellularly and then extracting the POI with the method of the present invention, the POI will be non-glycosylated, because the POI has not passed through the secretion pathway where glycosylation takes place.

(III) Fungal Host Organisms

Suitable host organisms among filamentous fungi include species of *Aspergillus*, e.g. *Aspergillus niger, Aspergillus oryzae, Aspergillus tubigensis, Aspergillus awamori* or *Aspergillus nidulans*. Alternatively, strains of a *Fusarium* species, e.g. *Fusarium oxysporum* or of a *Rhizomucor* species such as *Rhizomucor miehei* can be used as the host organism. Other suitable strains include *Thermomyces* and *Mucor* species.

Large Scale Application

In one preferred embodiment of the present invention, the POI is used for large scale applications.

Preferably the POI is produced in a quantity of from 1 g per liter to about 2 g per liter of the total cell culture volume after cultivation of the host organism.

Preferably the POI is produced in a quantity of from 100 mg per liter to about 900 mg per liter of the total cell culture volume after cultivation of the host organism.

Preferably the POI is produced in a quantity of from 250 mg per liter to about 500 mg per liter of the total cell culture volume after cultivation of the host organism.

Food Applications

In one preferred embodiment, the method of the present invention is used to release a POI for use in the manufacture of food products, such as beverages.

In another preferred embodiment, the method of the present invention is used to release a POI for use in the preparation of detergents.

In another preferred embodiment, the method of the present invention is used to release a POI suitable for use in baking.

In another preferred embodiment, the method of the present invention is used to release a POI suitable for use as a dough improving agent.

In another preferred embodiment, the method of the present invention is used to release a POI suitable for improving the properties of a flour dough, a flour dough improving composition and improved food products (see WO 96/39851 and EP-B-0 833 563).

In a preferred embodiment, the released POI is a hexose oxidase (D-hexose: $O_2$-oxidoreductase, EC 1.1.3.5).

HOX Enzyme

Hexose oxidase (D-hexose: $O_2$-oxidoreductase, EC 1.1.3.5) (also referred to as HOX) is an enzyme that in the presence of oxygen is capable of oxidising D-glucose and several other reducing sugars including maltose, lactose and cellobiose to their corresponding lactones with subsequent hydrolysis to the respective aldobionic acids. Accordingly, HOX differs from another oxidoreductase, glucose oxidase, which can only convert D-glucose, in that the enzyme can utilise a broader range of sugar substrates. The oxidation catalysed by HOX can be illustrated as follows:

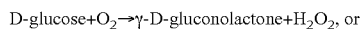

D-glucose+$O_2$→γ-D-gluconolactone+$H_2O_2$, or

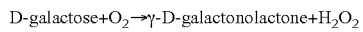

D-galactose+$O_2$→γ-D-galactonolactone+$H_2O_2$

HOX is produced naturally by several marine algal species. Such species are found inter alia in the family Gigartinaceae. As used herein, the term "HOX" denotes an enzyme which is capable of oxidising the substrates selected from the group consisting of D-glucose, D-galactose, D-mannose, maltose, lactose and cellobiose.

HOX Production

The gene encoding the HOX enzyme has been cloned from the seaweed *Chondrus crispus* (Stougaard and Hansen 1996, Hansen and Stougaard, 1997). The methylotrophic yeast *Hansenula polymorpha* (developed at Rhein Biotech, Dusseldorf/Germany as an expression system for heterologous proteins) has also been used to produce the HOX enzyme (the native protein was purified from seaweed (Poulsen and Høstrup, 1998)). WO 96/40935 and WO 98/13478 also disclose the cloning and expression in recombinant host organisms of a gene encoding a protein with HOX activity.

In one preferred embodiment the HOX enzyme comprises the sequence set out in SEQ ID No 22.

In one preferred embodiment the HOX enzyme comprises the sequence set out in SEQ ID No 22 or variants, homologues, derivatives or fragments thereof.

Glucan Lyase

Glucan lyase is an enzyme (EC 4.2.2.13) which catalyses the degradation of α-1,4-glucans in starch and glycogen to 1,5-anhydro-D-fructose (see FIG. 15).

In one embodiment, therefore, the POI comprises a glucan lyase enzyme. As shown in the Examples, glucan lyase is released at high specific activity and yield when expressed from a host, for example, *Hansenula polymorpha*. Extraction of expressed glucan lyase by a membrane extracting composition comprising a quaternary ammonium compound such as LTAB provides a high yield. The yield is much higher than previous methods using secretion from *Pichia pistoris* or *Aspergillus niger*.

In one embodiment, the yield of glucan lyase protein, measured in mass/volume of culture, is more than 1 g/l, preferably more than 2 g/l, most preferably more than 3 g/l or 3.5 g/l or more. In another embodiment, the yield of glucan lyase protein, may be measured as measured as a specific activity, for example, by the DNS method described in Yu et al (1998), *Carbohydrate Research* 305 p.73-82. In such an assay, the absorbance measured at 550 nanometers is a measurement of the amount of 1,5-anhydrofructose produced and can be used to determine the specific activity of glucan lyase. The DNS assay measures specific activity in units of μmol 1,5-anhydrofrucose/min·mg.

In highly preferred embodiments, the specific activity measured using such a DNS assay, of glucan lyase produced as described, is 5 μmol 1,5-anhydrofrucose/min·mg or more, preferably 6 μmol 1,5-anhydrofrucose/min-mg or more, more preferably 7 μmol 1,5-anhydrofrucose/min·mg or more, more preferably 9 μmol 1,5-anhydrofrucose/min·mg or more, more preferably 9 μmol 1,5-anhydrofrucose/min·mg or more, most preferably 10 μmol 1,5-anhydrofrucose/min-mg or more.

In contrast, previous methods employing transformation of the algal α-1,4-glucan lyase gene in the methylotrophic yeast *Pichia pastoris* has previously resulted in a specific activity of 0.7 μmol 1,5-anhydrofrucose/min·mg protein (Bojsen K, et al, 1999). Accordingly, expression and extraction using a membrane extracting composition comprising a quaternary ammonium compound results in an improved yield over the prior art.

Glucan lyase is described in detail in U.S. Pat. No. 6,541,237. Glucan lyase has also been described in Yu,S., et al 1999. The enzyme consists of 1038 amino acids and has a molecular weight of 117 kDa. The optimal pH range is between pH 4-7 and the temperature optimum for the glucan lyase is in the range 37-50° C. The enzyme is very stable showing no loss of activity when kept for several months at 22° C. at pH 5.5-5.8 (Yu, 2003, personal communication).

Glucan lyase is also known as Exo-(1,4)-alpha-D-glucan lyase, Exo-alpha-1,4-glucan lyase, Alpha-1,4-glucan lyase, Alpha-1,4-glucan exo-lyase and Alpha-1,4-glucan 1,5-anhydro-D-fructose eliminase.

The reaction catalysed by glucan lyase can be illustrated as follows:

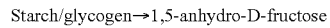

Starch/glycogen→1,5-anhydro-D-fructose

Biochemically, the glucan lyase enzyme catalyzes the sequential degradation of (1->4)-alpha-D-glucans from the non-reducing end with the release of 1,5-anhydro-D-fructose. Thus, for an alpha-glucan containing n(1→4)-linked glucose units, the final products are 1 glucose plus (n−1) 1,5-anhydro-D-fructose. Maltose, maltosaccharides and amylose are all completely degraded. Glucan lyase does not degrade (1→6)-alpha-gucosidic bonds and thus the degradation of a branched glucan, such as amylopectin or glycogen, will result in the formation of 1,5-anhydro-D-fructose plus a limit dextrin.

Methods for the isolation of glucan lyase from fungus, for example, *Morchella costata* or *Morchella vulgaris* (and sequences of the genes) are disclosed in detail in U.S. Pat. No. 5,908,760, herein incorporated by reference. Corresponding database entries include accession numbers AAE24524, AAE24523 and AAE24522. Isozymes of gulcan lyase have also been identified, such as alpha-1,4-glucan lyase, isozyme 5 (accession CAB51913), alpha-1,4-glucan lyase, isozyme 4 (accession CAB51909), alpha-1,4-glucan lyase, isozyme 3 (accession CAB51912), alpha-1,4-glucan lyase, isozyme 2 (accession CAB51911), and alpha-1,4-glucan lyase isozyme 1 (accession CAB51910), all from *Gracilariopsis lemaneiformis*

Other alpha-1,4-glucan lyases include those from Peziza ostracoderma (accession CAB52202), *Morchella vulgaris* (accession CAB52201), *Morchella costata* (accession CAB52260).

Algal glucan lyases are the subject of U.S. Pat. No. 5,695,970, particularly those from order Gigartinales, for example *Gracilariopsis lemaneiformis, Gracilaria verrucosa* and *Phyllophora truncata*. This document discloses several sequences of glucan lyases, each of which may be employed in the methods and compositions described here. For example, accession numbers AAC12432, AAC12431, AAC12430, AAC12429 and AAB27587. Such glucan lyases are particularly preferred.

In highly preferred embodiments, the term "glucan lyase", as it is used in this document, should preferably be taken to mean an enzyme comprising (a) the amino acid sequence of SEQ ID NO: 3 or SEQ ID NO:4, (b) an amino acid sequence which is at least 85% homologous to the amino acid sequence of SEQ ID NO:3 or SEQ ID NO:4 as shown in U.S. Pat. No. 6,541,237, in which the enzyme has .alpha.-1,4 glucan lyase activity. The entirety of U.S. Pat. No. 6,541,237 is incorporated herein by reference.

Glucan lyase may be produced by any of the methods described in U.S. Pat. No. 6,541,237, herein incorporated by reference.

In one preferred embodiment the glucan lyase enzyme comprises the sequence set out in SEQ ID No 3 in U.S. Pat. No. 6,541,237, or variants, homologues, derivatives or fragments thereof.

In one preferred embodiment the glucan lyase enzyme comprises the sequence set out in SEQ ID No 4 in U.S. Pat. No. 6,541,237, or variants, homologues, derivatives or fragments thereof.

Variants/Homologues/Derivatives (Amino Acid Sequence)

Preferred amino acid sequences of the present invention are set out in SEQ ID No 22 or are sequences obtainable from the HOX enzyme of the present invention but also include homologous sequences obtained from any source, for example related viral/bacterial proteins, cellular homologues and synthetic peptides, as well as variants or derivatives thereof.

Thus, the present invention covers variants, homologues or derivatives of the amino acid sequences presented herein, as well as variants, homologues or derivatives of the nucleotide sequence coding for those amino acid sequences.

In the context of the present invention, a homologous sequence is taken to include an amino acid sequence which is at least 75, 85 or 90% identical, preferably at least 95 or 98% identical at the amino acid level over at least, for example, the amino acid sequence as set out in SEQ ID No 22 of the sequence listing herein. In particular, homology should typically be considered with respect to those regions of the sequence known to be essential for enzyme activity rather than non-essential neighbouring sequences. These regions include but are not limited to the putative FAD binding domains in HOX such as SGGH$_{79}$C (residues 76-80 of SEQ ID NO: 23), LGGH$_{146}$I (residues 143-147 of SEQ ID NO: 23) and LGGH$_{320}$A (residues 317-321 of SEQ ID NO: 23). Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Although the final % homology can be measured in terms of identity, the alignment process itself is typically not based on an all-or nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The terms "variant" or "derivative" in relation to the amino acid sequences of the present invention includes any substitution of, variation of, modification of, replacement of, deletion of or addition of one (or more) amino acids from or to the sequence providing the resultant amino acid sequence has an enzyme activity, preferably having at least the same enzyme activity as the amino acid sequence set out in SEQ ID No 22.

SEQ ID No 22 may be modified for use in the present invention. Typically, modifications are made that maintain the enzyme activity of the sequence. Amino acid substitutions may be made, for example from 1, 2 or 3 to 10 or 20 substitutions provided that the modified sequence retains the required enzyme activity. Amino acid substitutions may include the use of non-naturally occurring analogues.

SEQ ID No 22 of the present invention may also have deletions, insertions or substitutions of amino acid residues which produce a silent change and result in a functionally equivalent enzyme. Deliberate amino acid substitutions may be made on the basis of similarity in polarity, charge, solubility, hydrophobicity, hydrophilicity, and/or the amphipathic nature of the residues as long as the enzyme activity of the HOX enzyme is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Variants/Homologues/Derivatives (Nucleotide Sequence)

It will be understood by a skilled person that numerous different nucleotide sequences can encode the same HOX enzyme as a result of the degeneracy of the genetic code. In addition, it is to be understood that skilled persons may, using routine techniques, make nucleotide substitutions that do not affect the HOX enzyme encoded by the nucleotide sequence of the invention to reflect the codon usage of any particular host organism in which the HOX enzyme of the present invention is to be expressed.

The terms "variant", "homologue" or "derivative" in relation to the nucleotide sequence set out in SEQ ID No 22 of the present invention includes any substitution of, variation of, modification of, replacement of, deletion of or addition of one (or more) nucleic acid from or to the sequence providing the resultant nucleotide sequence codes for a HOX enzyme having an enzyme activity, preferably having at least the same activity as the nucleotide sequence set out in SEQ ID No 22 of the sequence listings.

As indicated above, with respect to sequence homology, preferably there is at least 75%, more preferably at least 85%, more preferably at least 90% homology to the sequences shown in the sequence listing herein. More preferably there is at least 95%, more preferably at least 98%, homology. Nucleotide homology comparisons may be conducted as described above. A preferred sequence comparison program is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

The present invention also encompasses nucleotide sequences that are capable of hybridising selectively to the sequences presented herein, or any variant, fragment or derivative thereof, or to the complement of any of the above. Nucleotide sequences are preferably at least 15 nucleotides in length, more preferably at least 20, 30, 40 or 50 nucleotides in length.

Hybrisation

The term "hybridization" as used herein shall include "the process by which a strand of nucleic acid joins with a complementary strand through base pairing" as well as the process of amplification as carried out in polymerase chain reaction (PCR) technologies.

Nucleotide sequences of the invention capable of selectively hybridising to the nucleotide sequences presented herein, or to their complement, will be generally at least 75%, preferably at least 85 or 90% and more preferably at least 95% or 98% homologous to the corresponding nucleotide sequences presented herein over a region of at least 20, preferably at least 25 or 30, for instance at least 40, 60 or 100 or more contiguous nucleotides. Preferred nucleotide sequences of the invention will comprise regions homologous to the nucleotide sequence set out in SEQ ID No 22 preferably at least 80 or 90% and more preferably at least 95% homologous to the nucleotide sequence set out in SEQ ID No 22.

The term "selectively hybridizable" means that the nucleotide sequence used as a probe is used under conditions where a target nucleotide sequence of the invention is found to hybridize to the probe at a level significantly above background. The background hybridization may occur because of other nucleotide sequences present, for example, in the cDNA or genomic DNA library being screened. In this event, background implies a level of signal generated by interaction between the probe and a non-specific DNA member of the library which is less than 10 fold, preferably less than 100 fold as intense as the specific interaction observed with the target DNA. The intensity of interaction may be measured, for example, by radiolabelling the probe, e.g. with $^{32}P$.

Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm−5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridization can be used to identify or detect identical nucleotide sequences while an intermediate (or low) stringency hybridization can be used to identify or detect similar or related polynucleotide sequences.

In a preferred aspect, the present invention covers nucleotide sequences that can hybridise to the nucleotide sequence of the present invention under stringent conditions (e.g. 65° C. and 0.1×SSC {1×SSC=0.15 M NaCl, 0.015 M $Na_3$ Citrate pH 7.0). Where the nucleotide sequence of the invention is double-stranded, both strands of the duplex, either individually or in combination, are encompassed by the present invention. Where the nucleotide sequence is single-stranded, it is to be understood that the complementary sequence of that nucleotide sequence is also included within the scope of the present invention.

Nucleotide sequences which are not 100% homologous to the sequences of the present invention but fall within the scope of the invention can be obtained in a number of ways. Other variants of the sequences described herein may be obtained for example by probing DNA libraries made from a range of sources. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of the nucleotide sequence set out in SEQ I.D. No 22 under conditions of medium to high stringency. Similar considerations apply to obtaining species homologues and allelic variants of the amino acid and/or nucleotide sequences of the present invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used. The primers used in degenerate PCR will contain one or more degenerate positions and will be used at stringency conditions lower than those used for cloning sequences with single sequence primers against known sequences.

Alternatively, such nucleotide sequences may be obtained by site directed mutagenesis of characterised sequences, such as the nucleotide sequence set out in SEQ ID. No 22. This may be useful where for example silent codon changes are required to sequences to optimise codon preferences for a particular host cell in which the nucleotide sequences are being expressed. Other sequence changes may be desired in order to introduce restriction enzyme recognition sites, or to alter the enzyme activity of the HOX enzyme encoded by the nucleotide sequences.

The nucleotide sequences of the present invention may be used to produce a primer, e.g. a PCR primer, a primer for an alternative amplification reaction, a probe e.g. labelled with a revealing label by conventional means using radioactive or non-radioactive labels, or the nucleotide sequences may be cloned into vectors. Such primers, probes and other fragments will be at least 15, preferably at least 20, for example at least 25, 30 or 40 nucleotides in length, and are also encompassed by the term nucleotide sequence of the invention as used herein.

The nucleotide sequences such as a DNA polynucleotides and probes according to the invention may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer nucleotide sequences will generally be produced using recombinant means, for example using a PCR (polymerase chain reaction) cloning techniques. This will involve making a pair of primers (e.g. of about 15 to 30 nucleotides) flanking a region of the targeting sequence which it is desired to clone, bringing the primers into contact with mRNA or cDNA, performing a polymerase chain reaction (PCR) under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Due to the inherent degeneracy of the genetic code, other DNA sequences which encode substantially the same or a functionally equivalent amino acid sequence, may be used to clone and express the HOX enzyme. As will be understood by those of skill in the art, it may be advantageous to produce the HOX enzyme—encoding nucleotide sequences possessing non-naturally occurring codons. Codons preferred by a particular prokaryotic or eukaryotic host (Murray E et al (1989) Nuc Acids Res 17:477-508) can be selected, for example, to increase the rate of the HOX enzyme expression or to produce recombinant RNA transcripts having desirable properties, such as a longer half-life, than transcripts produced from naturally occurring sequence.

Screens

The method of the present invention may be used for screening for elevated levels of the intracellular POI in mutated host cell organisms. The cells employed in such a screen may be affixed to a solid support or on a solid substrate, such as plastic pins or some other surface. The cells may be contacted with the membrane extracting composition of the present invention and the level of the released POI may be measured using methods known in the art.

High Through Put Screens (HTS)

The method of the present invention may be used in high through-put screening (HTS) systems, where target cells are grown and screened in microtiter plates (10000 mutants per day) by robot systems. By way of example, when making new recombinant production strains, it is usually necessary to carry out one or several rounds of traditional mutagenesis in order to increase productivity. This is most efficiently done using HTS of the mutated cells.

The method of the present invention is highly advantageous because it allows for high through put screening (HTS) for increased levels of intracellular POIs. Up until now, these systems were only able to screen for higher levels of secreted POIs.

BRIEF DESCRIPTION OF THE FIGURES

The present invention will now be described only by way of example in which reference is made to the following Figures.

FIG. 1 provides a genetic construct;
FIG. 2A provides genetic constructs;
FIGS. 3A and 3B provide photographic representations;
FIG. 5 provides a sequence listing;
FIG. 6 provides a sequence listing;
FIGS. 7A-7D provide a photographic representation;
FIGS. 17A to 17C show a photographic representation.

FIG. 20 shows a photographic representation; and

In slightly more detail:

FIG. 1 provides a physical map of the expression vector for HOX production in *Hansenula polymorpha*. EcoRI/NotI blunt fragments harbouring the coding region of the synthetic HOX gene fused to optional signal sequences were cloned into the multiple cloning site of a standard *Hansenula* expression vector. The expression vectors contain the promoter of formate dehydrogenase (FMD) gene and the terminator (MOX-T) of the methanol oxidase gene separated by the multiple cloning site for fragment insertion, ori and bla (ampR) for propagation and selection in *E. coli*, the ARS (HARS) sequence for replication in *H. polymorpha*, the URA3 gene for selection.

FIG. 2A shows a diagram of the 1.4 kb genuine FMD gene (upper scheme) and the FMD promoter with the cloned heterologous DNA (lower scheme). The restriction sites are Asp718, NcoI.

Figure 2B:
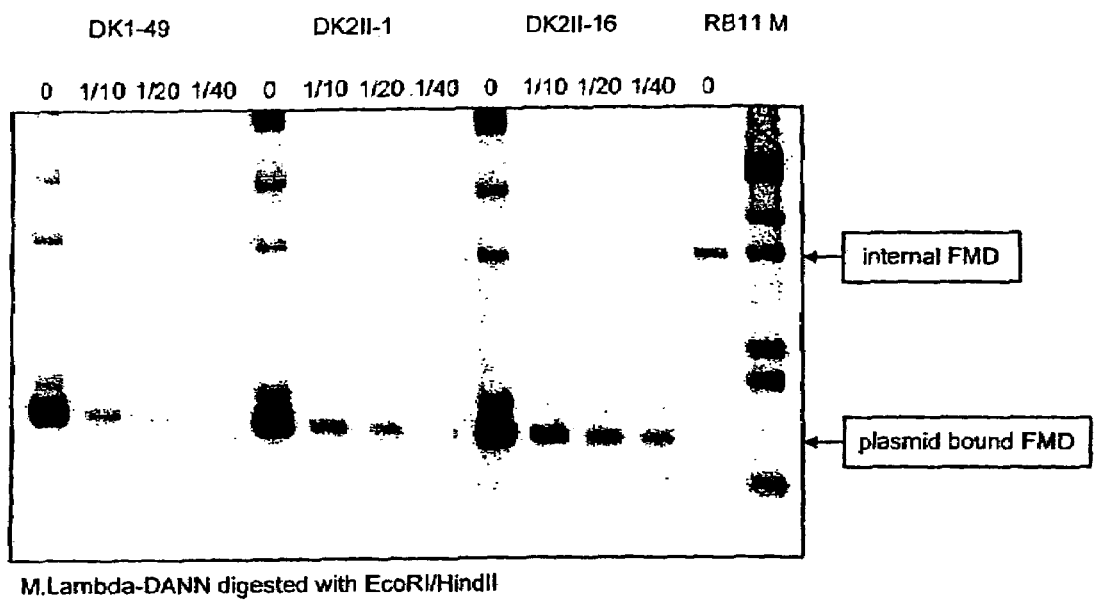
FIG. 2B provides a photographic representation.

FIG. 2B shows the gene copies of the integrated HOX gene. Lanes 1-12 show different recombinant isolates and their corresponding DNA dilution. Lane 13 shows an untransformed host strain and Lane 14 shows a size marker (M).

FIGS. 3A & 3B provide an SDS-PAGE analysis of HOX expression. FIG. 3A provides an SDS-PAGE analysis of culture filtrate from glycerol fermentation of the mutagenized strain DK8-27KanII3-mut25. Lane 1 shows a marker protein, lane 2 shows a HOX standard (0.03 U/ml; 18 ul), lane 3 shows a supernatant from probe 3 (18 ul), lane 4 shows a supernatant from probe 4 (18 ul), lane 5 shows a supernatant from probe 5 (18 ul), lane 6 shows a supernatant from probe 6 (18 ul), lane 7 shows a supernatant from probe 7 (18 ul), lane 8 shows a supernatant from probe 8 (18 ul), lane 9 shows a supernatant from probe 9 (18 ul) and lane 10 shows a supernatant from probe 10 (18 ul).

FIG. 3B provides a western blot analysis of recombinant strains expressing HOX. The samples applied in the lanes are the same as for FIG. 3A. The membrane was probed with a polyclonal HOX antibody.

Figure 4:
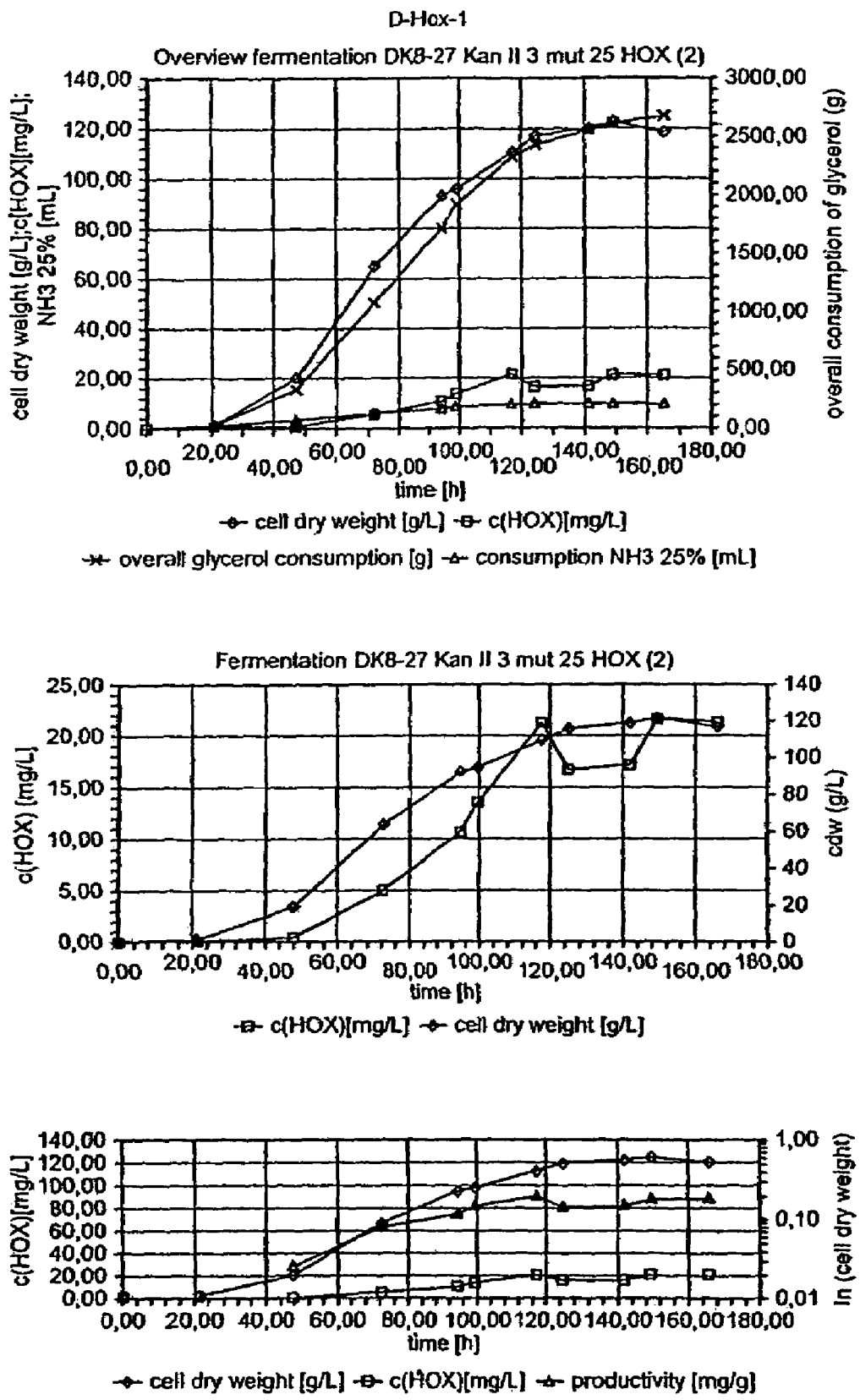
FIG. 4 provides a graph.

FIG. 4 shows the growth and productivity of a 10 liter fermentation culture of a secreting strain DK8-27KanII3-mut25. The fermentation was performed at 25° C. and pH 5.0 with glycerol and $pO_2$ control.

FIG. 5 provides the individual oligonucleotides used to synthesize the HOX gene with codon optimization (SEQ ID NOS 2-21, respectively in order of appearance).

FIG. 6 provides a nucleotide sequence of the synthetic HOX gene (SEQ ID NO: 22) and the corresponding amino acid sequence (SEQ ID NO: 23).

FIGS. 7A-7D show the localisation of the HOX enzyme in *H. polymorpha* as determined by immunofluorescence. The superimposition of the location of the HOX enzyme (green signal) with the nuclear location (blue signal) is shown. See A) RB11 strain without HOX gene. B) DK8-27. C) DK8-27 mut25. D) DK2II-I.

Figure 8:
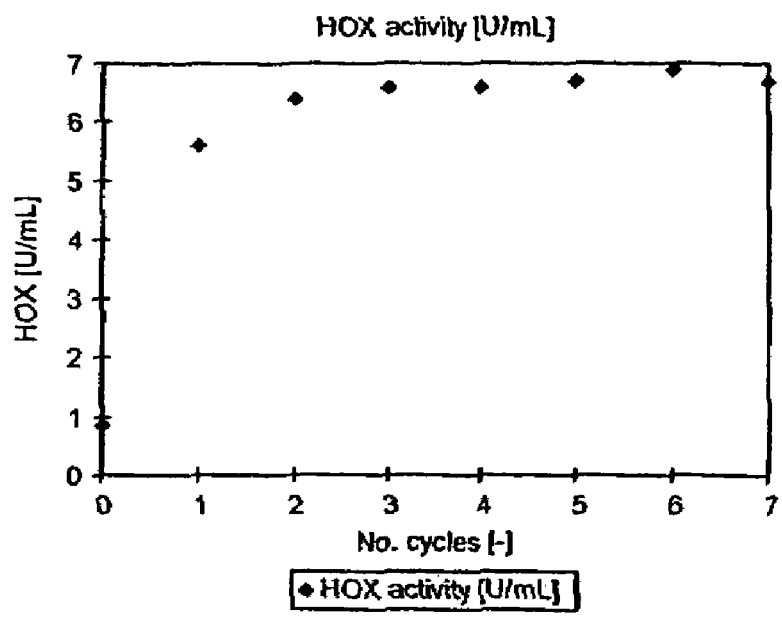
FIG. 8 provides a graph.

FIG. 8 provides a graph showing HOX activity as a function of number of cycles through a cell homogenizer.

Figure 9:
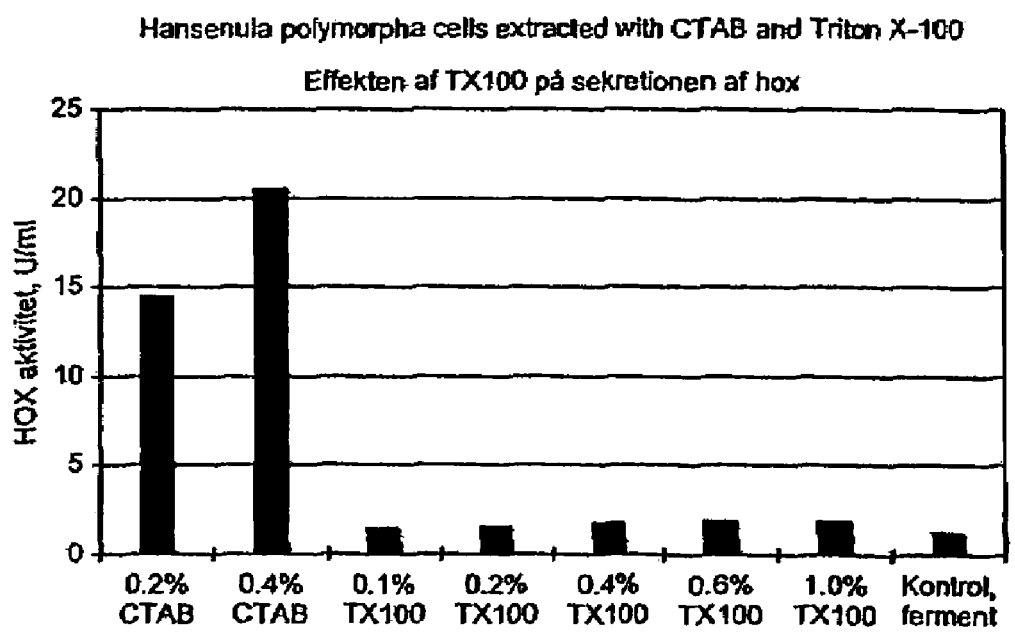
FIG. 9 provides a graph.

FIG. 9 provides a graph showing *Hansenula polymorpha* cells extracted with different concentration of CTAB and Triton X-100.

Figure 10A:
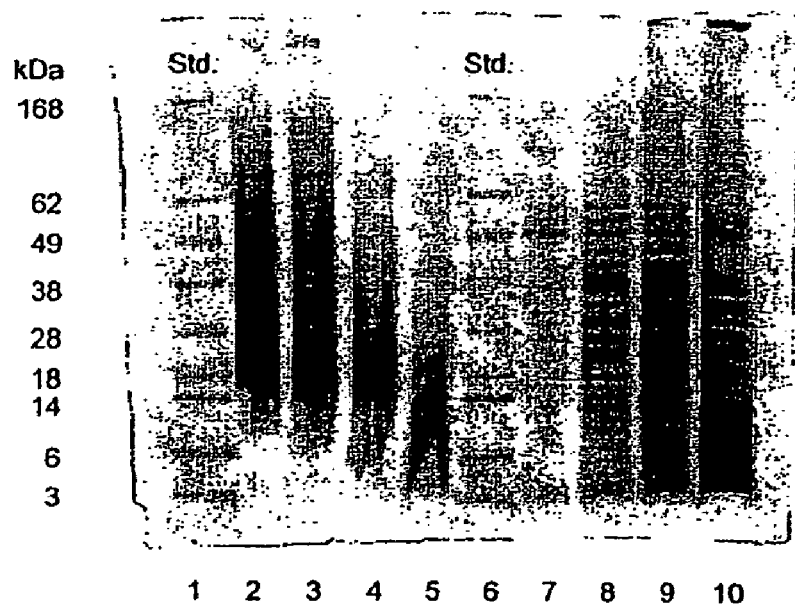
FIGS. 10A-10B provide a photographic representation.

FIG. 10A shows an SDS PAGE analysis of HOX enzyme levels in the cell supernatant (lanes 7-10) and pellet (lanes 2-5) after CTAB treatment. The HOX enzyme was released from the pellets by mechanical extraction. The samples were analysed on 4-12% NuPAGE gels from MES, Novex and 10 µl samples were loaded in each lane in the following order: Lane 2-5: residual HOX in the cell pellet; Lane 7-10: released HOX in the supernatant; Lane 1 and 6: Novex See Blue standard; Lane 2: control, lane 3: 0.1% CTAB; lane 4: 0.2% CTAB; lane 5: 0.4% CTAB; lane 7: control; lane 8: 0.1% CTAB; lane 9: 0.2% CTAB and lane 10: 0.4% CTAB.

Figure 10B:
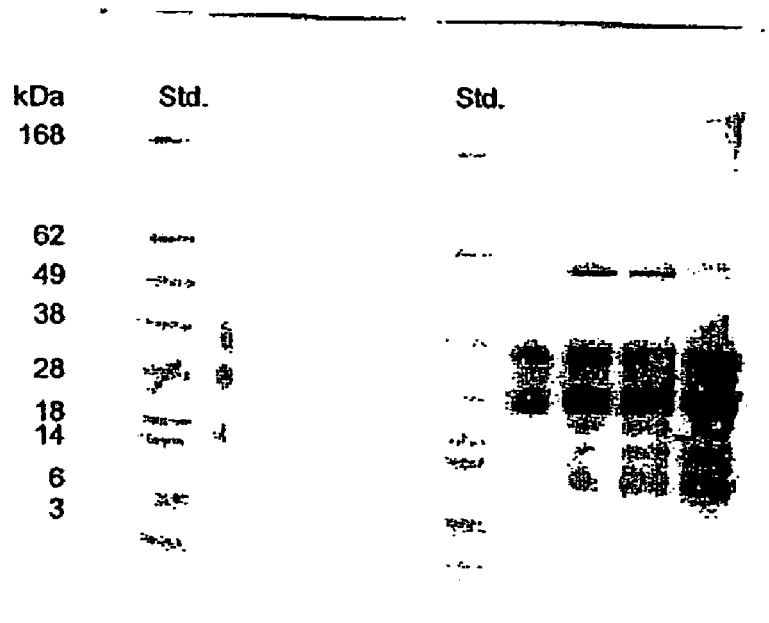

FIG. 10B shows a Western Blot analysis of HOX enzyme levels in the cell supernatant (lanes 7-10) and pellet (lanes 2-5) after CTAB treatment. The HOX enzyme was released from the pellets by mechanical extraction. The samples were analysed on 4-12% NuPAGE gels from MES, Novex and 5 µl samples were loaded in each lane in the following order: Lane 2-5: residual HOX in the cell pellet; Lane 7-10: released HOX in the supernatant; Lane 1 and 6: Novex See Blue standard, Lane 2: control, lane 3: 0.1% CTAB; lane 4: 0.2% CTAB; lane 5: 0.4% CTAB; lane 7: control; lane 8: 0.1% CTAB; lane 9: 0.2% CTAB and lane 10: 0.4% CTAB.

Figure 11A:
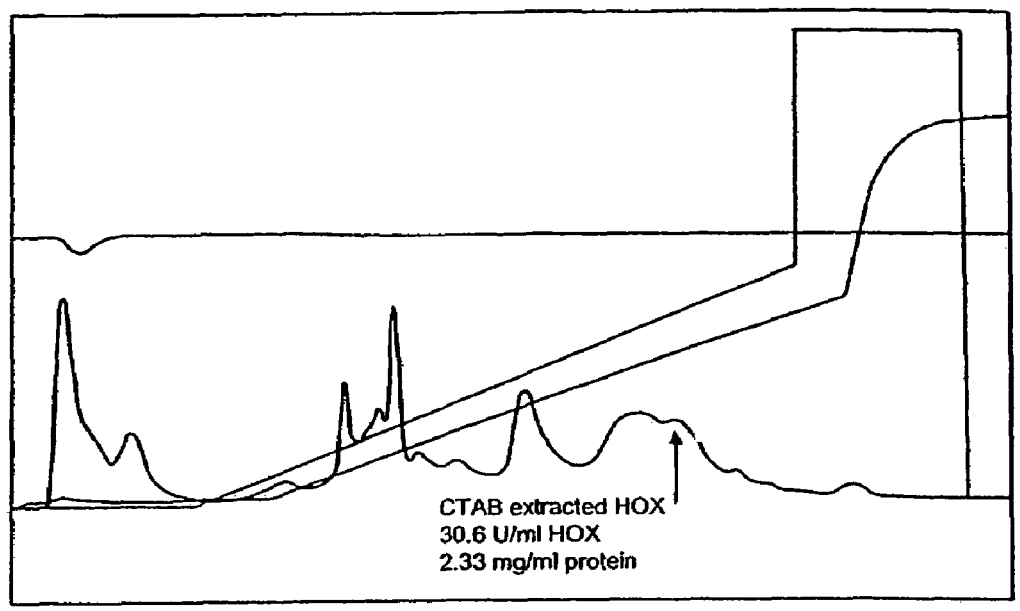
FIGS. 11A-11B provide a graph.

FIG. 11A shows the elution profile for CTAB extracted HOX.

Figure 11B:
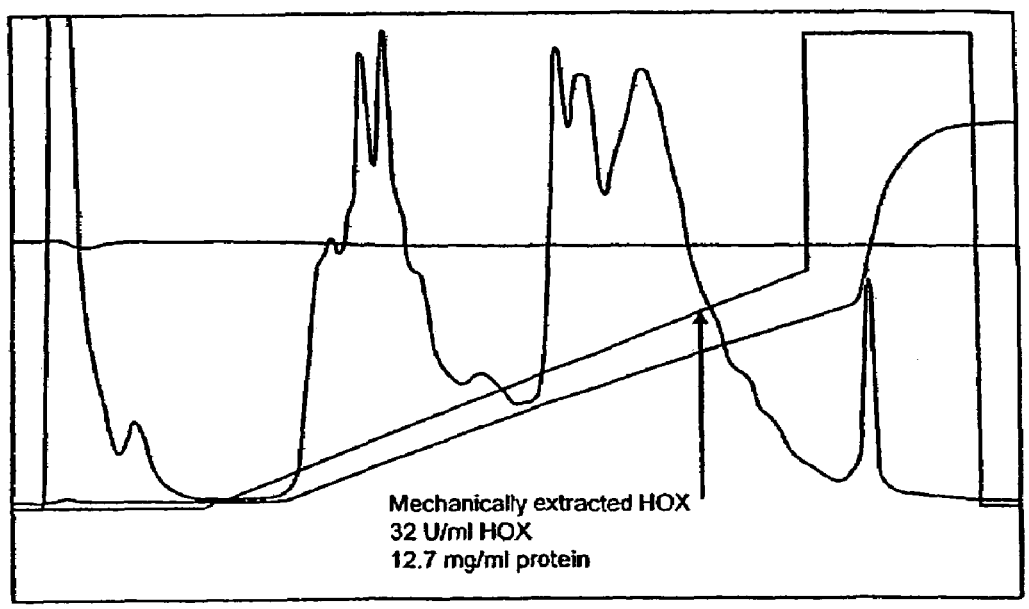

FIG. 11B shows the elution profile for mechanically extracted HOX.

Figure 12A:
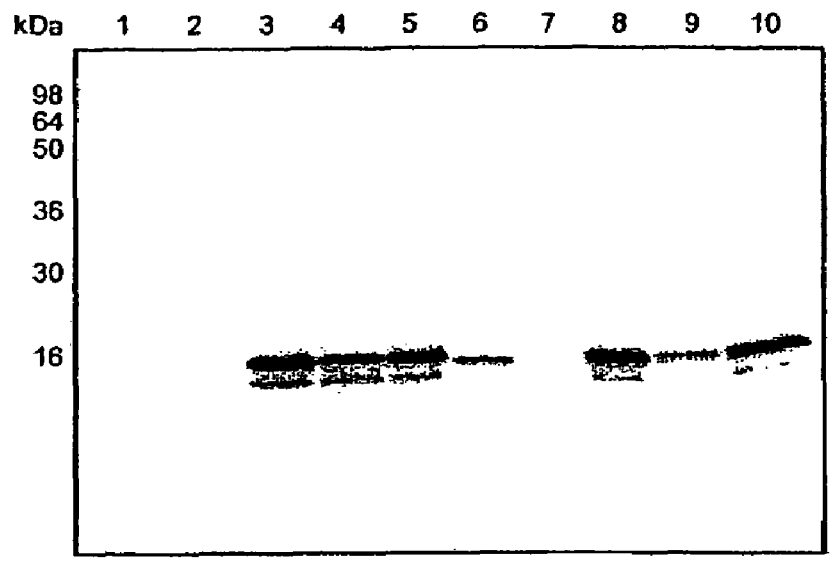
FIGS. 12A-12B provide a photographic representation.

FIG. 12A shows a Western Blot WB33. Lane 1 shows molecular weight markers See Blue 10 µL (total). Lane 2. 4-17 A SN 11.3 µL, Lane 3. 4-17 D CX 1:3 dil. 11.3 µL, Lane 4. 4-17C SN CTAB 11.3 µL, Lane 5.4-17 F CX CTAB 1:3 dil. 11.3 µL, Lane 6. rhII-1ra-standard (BSA-free) 30 ng, Lane 7. AL 9/2 A SN 11.3 µL, Lane 8. AL 9/2 D CX 1:3 dil. 11.3 µL, Lane 9. AL 9/2 C SN CTAB 11.3 µL, Lane 10. AL 9/2 F CX CTAB 1:3 dil. 11.3 µL.

Figure 12B:
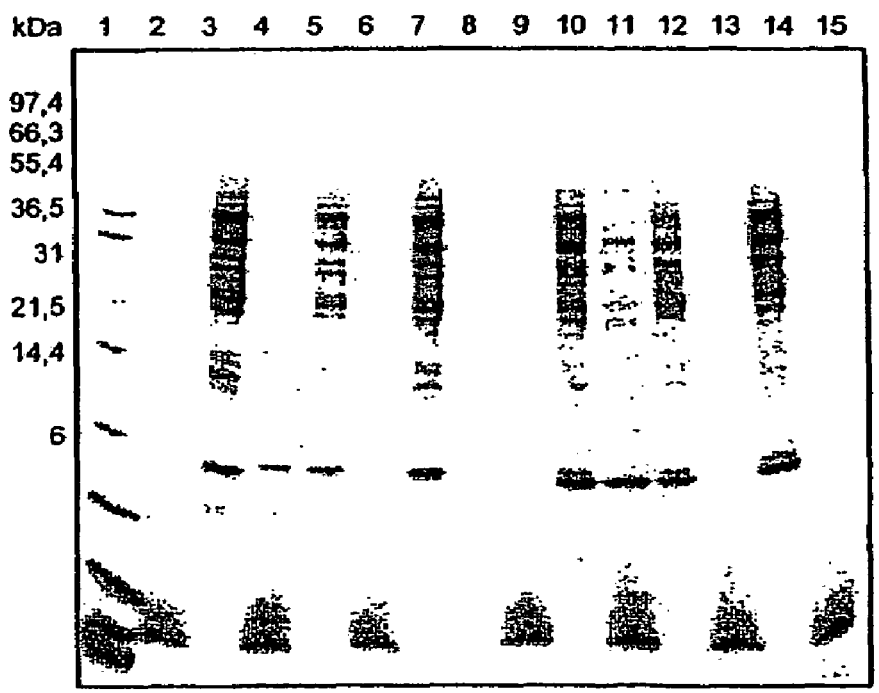

FIG. 12B shows a Coomassie Blot Coo2. Lane 1. MW marker Mark 12 10 µL (total), Lane 2. 4-17 A SN 11.3 µL, Lane 3. 4-17 D CX 1:3 dil. 11.3 µL, Lane 4. 4-17 C SN CTAB 11.3 µL, Lane 5. 4-17 F CX CTAB 1:3 dil. 11.3 µL, Lane 6. 4-17 B SN w/o CTAB 11.3 µL, Lane 7. 4-17 E CX w/o CTAB 1:3 dil. 11.3 µL, Lane 8.rhII-1ra-Standard (BSA-free) 100 ng, Lane 9. AL 9/2 A SN 11.3 µL, Lane 10. AL 9/2 D CX 1:3 dil. 11.3 µL, Lane 11. AL 9/2 C SN CTAB 11.3 µL, Lane 12. AL 9/2 F CX CTAB 1:3 dil. 11.3 µL, Lane 13. AL 9/2 B SN w/o CTAB 11.3 µL, Lane 14. AL 9/2 E CX w/o CTAB 1:3 dil. 11.3 µL, Lane 15. FPMT 8 A SN 11.3 µL.

Figure 13A:
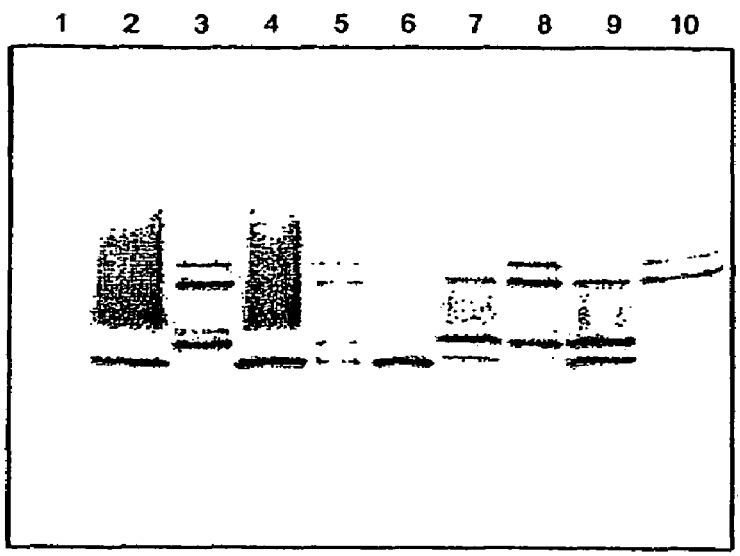
FIGS. 13A-13B provide a photographic representation.
Figure 13B:
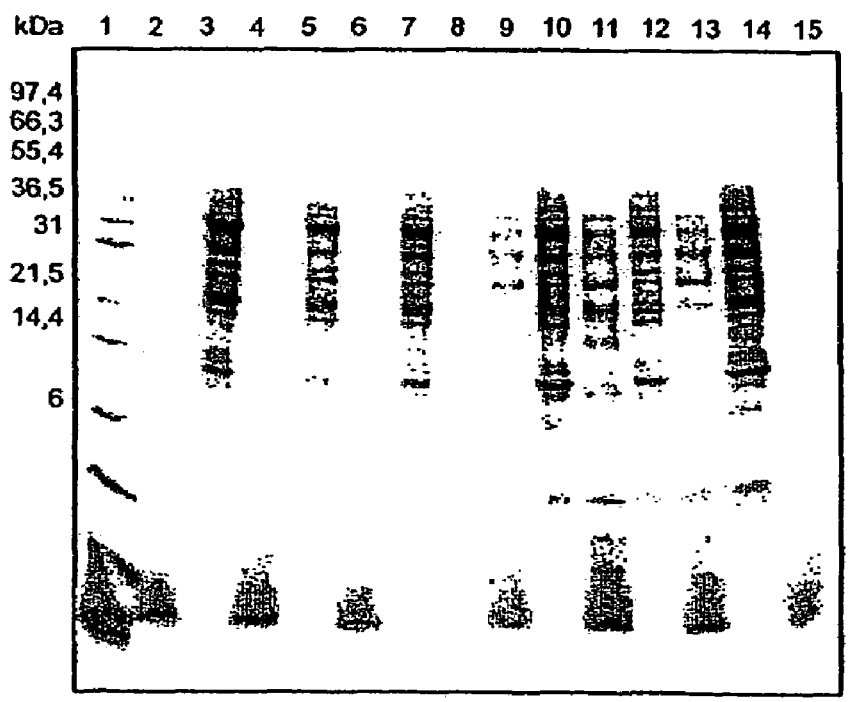
Figure 14A:
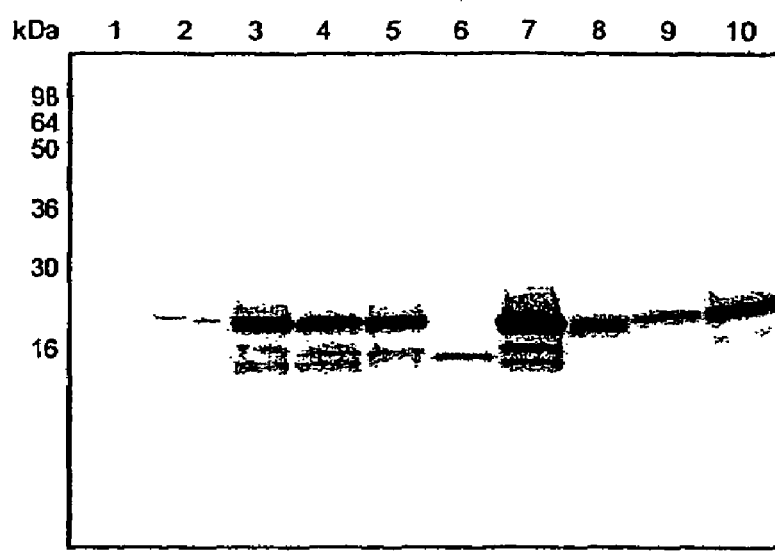
FIGS. 14A-14B provide a photographic representation.
Figure 14B:
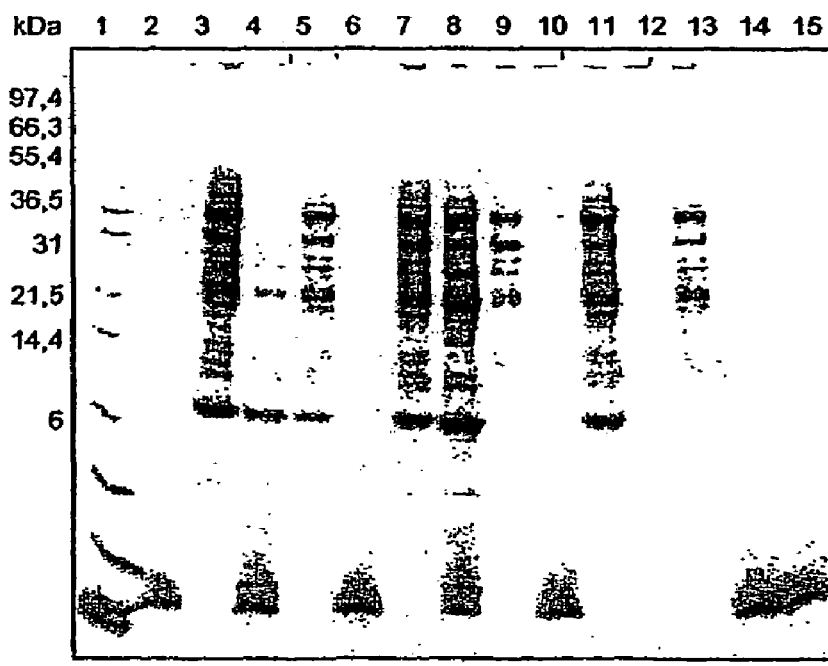

FIG. 13A shows a Western Blot WB 34. Lane 1. MW marker See Blue 10 µL (total), Lane 2. MFα☐2 A SN 11.3 µL, Lane 3. MFα2 D CX 1:3 dil. 11.3 µL, Lane 4. MFα☐2 C SN CTAB 11.3 µL, Lane 5. MFα☐2 F CX CTAB 1:3 dil. 11.3 µL, Lane 6. rhII-1ra-standard (BSA-free) 30 ng, Lane 7. MFα☐AL7/1 A SN 11.3 µL, Lane 8. MFα☐AL7/1 D CX 1:3 dil. 11.3 µL, Lane 9. MFαAL7/1 C SN CTAB 11.3 µL, Lane 10. MFα☐AL7/1 F CX CTAB 1:3 dil. 11.3 µL FIG. 13B shows a Coomassie Blot Coo 3 1. MW marker Mark 12 10 µL (total), Lane 2. MFα 2ASN 11.3 µL, Lane 3.MFα 2DCX 1:3 dil. 11.3 µL, Lane 4. MFα 2C SN CTAB 11.3 µL, Lane 5. MFα 2 F CX CTAB 1:3 dil. 11.3 µL, Lane 6. MFα 2 B SN w/o CTAB 11.3 µL, Lane 7. MFα 2 E CX w/o CTAB 1:3 dil. 11.3 µL, Lane 8.rhII-1ra-Standard (BSA-free) 100 ng, Lane 9. MFα AL7/1 A SN 11.3 µL, Lane 10. MFα AL7/1 D CX 1:3 dil. 11.3 µL, Lane 11. MFα AL7/1 C SN CTAB 11.3 µL, Lane 12. MFα AL7/1 F CX CTAB 1:3 dil. 11.3 µL, Lane 13. MFα AL7/1 B SN w/o CTAB 11.3 µL, Lane 14. MFα AL7/1 E CX w/o CTAB 1:3 dil. 11.3 µL, Lane 15. FPMT 8 C SN CTAB 11.3 µL FIG. 14A shows a Western Blot WB 35. Lane 1. MW marker See Blue 10 µL (total), Lane 2. II 3/1 SN 11.3 µL, Lane 3. II 3/1 CX 1:3 dil. 11.3 µL, Lane 4. II 3/1 SN CTAB 4° C. 11.3 µL, Lane 5. II 3/1 CX CTAB 4° C. 1:3 dil. 11.3 µL, Lane 6. rhII-1ra-Standard (BSA-free) 30 ng, Lane 7. II 3/1 SN CTAB 37° C. 11.3 µL, Lane 8. II 3/1 CX CTAB 37° C. 1:3 dil. 11.3 µL, Lane 9. II 3/1 SN w/o CTAB 37° C. 11.3 µL, Lane 10. II 3/1 CX w/o CTAB 37° C. 1:3 dil. 11.3 µL FIG. 14B shows a Coomassie Blot Coo 4 1. MW marker Mark 12 10 µL (total). Lane 2. II 3/1 SN 11.3 µL, Lane 3. II 3/1 CX 1:3 dil. 11.3 µL, Lane 4. II 3/1 SN CTAB 4° C. 11.3 µL, Lane 5. II 3/1 CX CTAB 4° C. 1:3 dil. 11.3 µL, Lane 6. II 3/1 SN w/o CTAB 4° C. 11.3 µL, Lane 7. II 3/1 CX w/o CTAB 4° C. 1:3 dil. 11.3 µL, Lane 8. II 3/1 SN CTAB 37° C. 11.3 µL, Lane 9. II 3/1 CX CTAB 37° C. 1:3 dil. 11.3 µL, Lane 10. II 3/1 SN w/o CTAB 37° C. 11.3 µL, Lane 11. II 3/1 CX w/o CTAB 37° C. 1:3 dil. 11.3 µL, Lane 12. rhII-1ra-Standard (BSA-free) 100 ng, Lane 13. FPMT 8 CX CTAB 4° C. 1:3 dil. 11.3 µL, Lane 14. FPMT 8 SN CTAB 4° C. 11.3 µL, Lane 15. FPMT 8 SN 11.3 µL.

Figure 15:
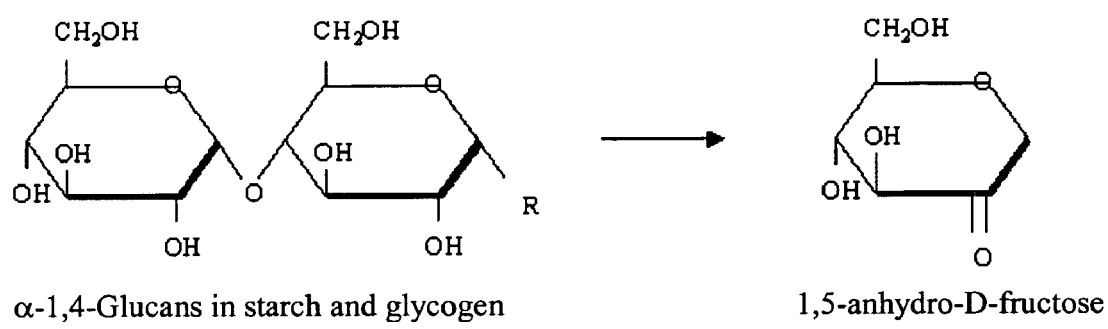
FIG. 15 provide a graphic representation of a reaction.

FIG. 15 shows the reaction catalyzed by glucan lyase.

Figure 16A:
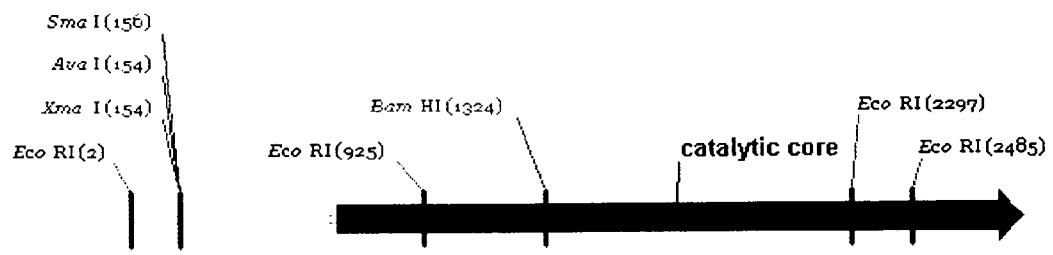
FIG. 16A shows a graphic representation of a gene structure.

FIG. 16A shows the structure of the full length glucan lyase gene (3153 bp). The central portion is well conserved among glucan lyases and alpha-glucocidases. The N terminal portion is believed to contain a starch-binding domain.

Figure 16B:
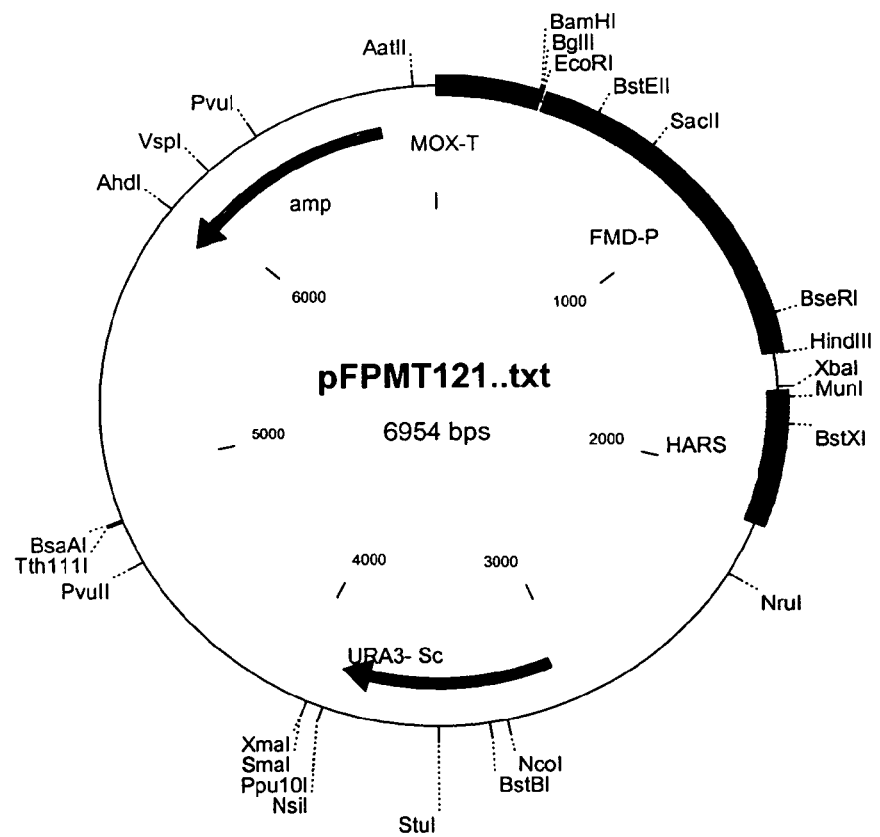
FIG. 16B shows a graphic representation of a expression vector structure.

FIG. 16B shows the structure of the Hansenula expression vector pFPMT121.

Figure 17A:
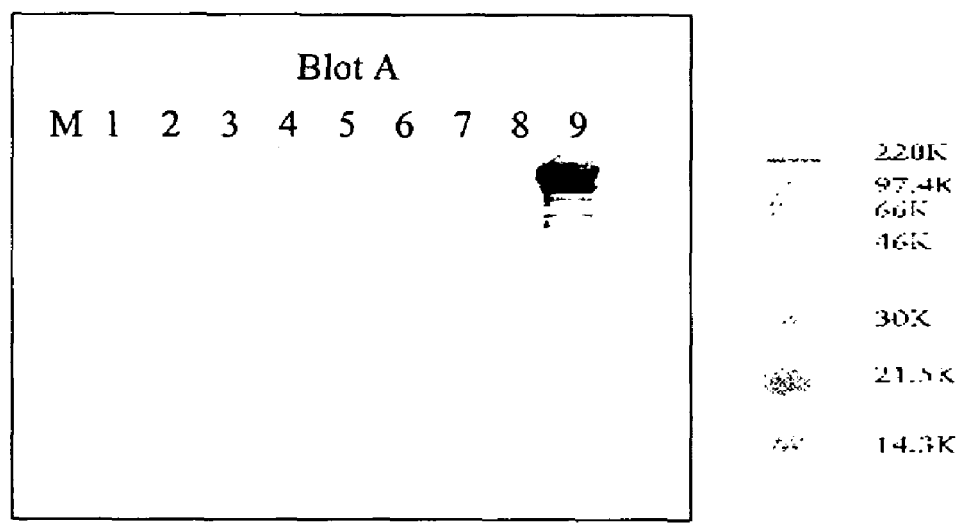
Figure 17B:
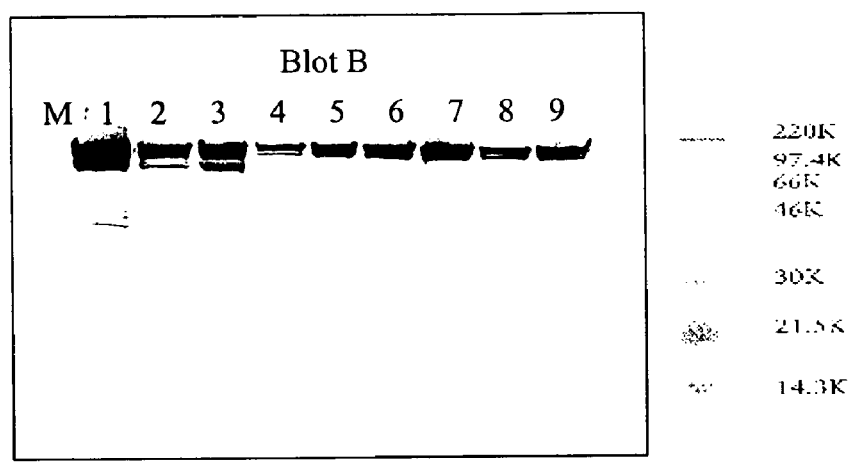

FIGS. 17A-17C. Western Blot analysis using anti-glucan lyase antibodies. 5 and 15 µl of cell-free extract of each transformant is loaded in two lanes.

FIG. 17A. Blot A: Lane 1-8: Transformants of the aglcore (transformant number 14, 15, 27 and 28). Lane 9: Transformant of the full-length glucan lyase gene (transformant number 2).

FIG. 17B. Blot B: Lane 1-9 Transformants of the full-length glucan lyase gene (transformant number 2, 4, 5, 6 and 8).

FIG. 17C. Blot C: Lane 1-8: Transformants of the 5' agl (transformant number 13, 14, 15 and 16). Lane 9-17: Transformants of the 3' agl (transformant number 6, 7, 8 and 9). The cell-free extracts are heat-treated in 10 µl of SDS sample buffer before loading on the SDS-gels. The proteins are transferred to nitrocellulose membranes that are blotted with Primary anti-algal glucan lyase antibodies from rabbits and secondary alkaline phosphatase Conjugated swine anti-rabbit immunoglobulins. 15 µl of Rainbow™ coloured protein molecular weight marker is loaded on each gel (M). The marker is not transferred very efficiently to the nitrocellulose membranes so the marker is shown to the right. Marker: Myosin 220 kDa (blue), phosphorylase b 97.4 kDa (brown), bovine serum albumin 66 kDa (red), ovalbumin 46 kDa (yellow), carbonic anhydrase 30 kDa (orange), trypsin inhibitor 21.5 kDa (blue), lysozyme 14.3 kDa (magenta).

Figure 18:
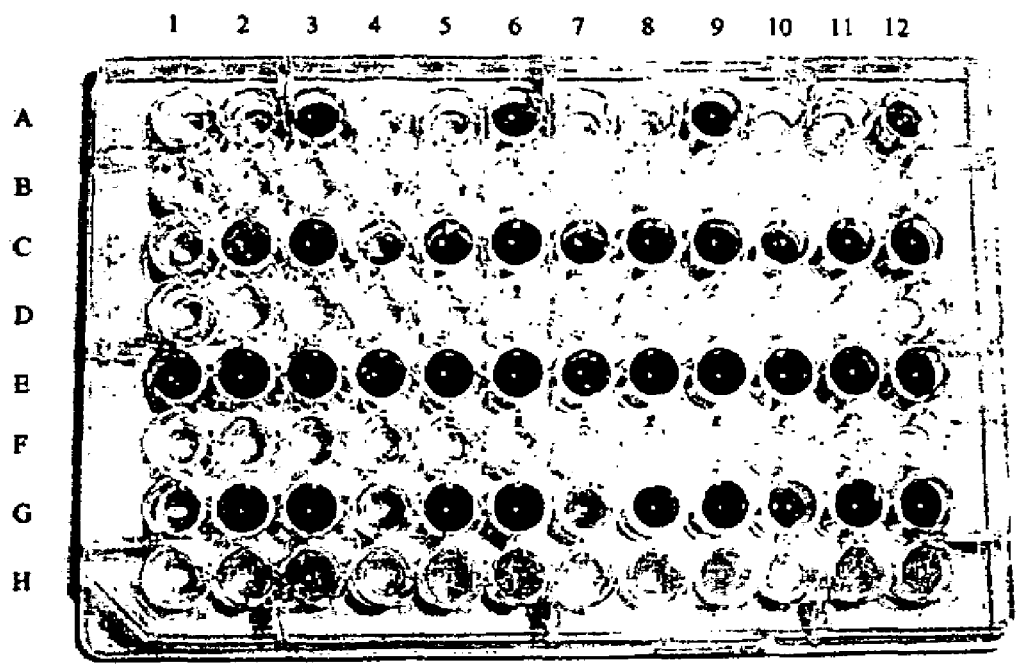
FIG. 18 shows a photographic representation.

FIG. 18. ELISA-plate from activity screening by the DNS method of repressed and induced extracts prepared from cultures of transformant 2 and 8 (2 cultures of each transformant are grown). In column 1-3 and 4-6 extracts from culture 1 and 2 of transformant 2 are assayed. In column 7-9 and 10-12 extracts from culture 1 and 2 of transformant 8 are assayed. A1-A12: Assay on 10, 20 and 50 µl of cell-free extracts from repressed cultures. The cells are opened mechanically on a Mini Bead-Beater. C1-C12: Assay on 10, 20 and 50 µl of cell-free extracts from induced cultures. The cells are opened mechanically on a Mini Bead-Beater. E1-E12: Assay on 1, 5 and 10 µl of cell-free extract from induced cultures. The cells are opened with the chemical reagent LTAB and the supernatant is used for the assay. G1-G12: The pellet from the LTAB opening is resuspended in 0.1 M MOPS-NaOH pH=6.2 and 1, 5 and 10 µl is used for the assay. The respective blanks are shown in B1-B12, D1-D12, F1-F12 and H1-H12.

Figure 19:
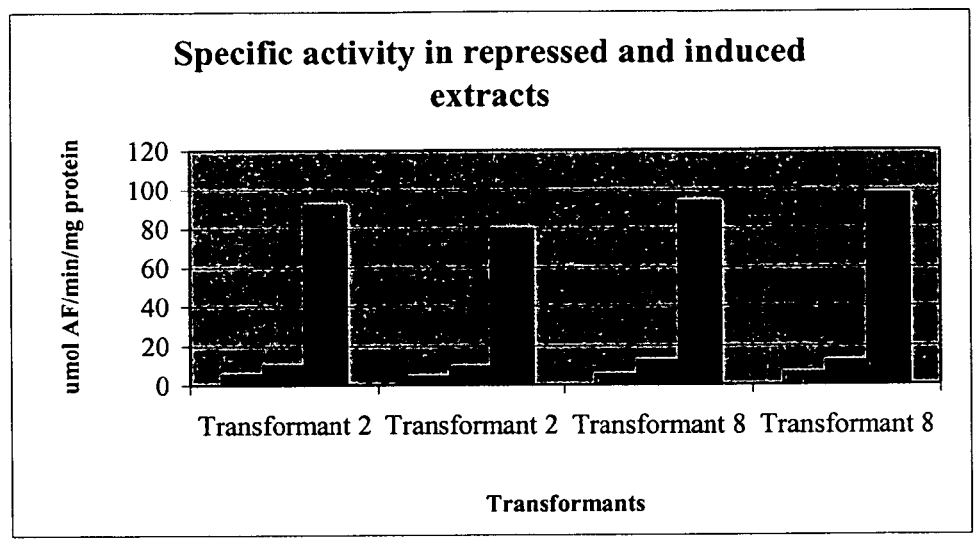
FIG. 19 shows a graph.

FIG. 19. The specific activity of algal α-1,4-glucan lyase is measured by the DNS method in cell-free extracts from repressed and induced cultures. The black columns show the specific activity when the cells are repressed in YND+2% glucose. The cells are opened mechanically on a Mini-Bead Beater. The pink and blue columns show the specific activity when the cells are depressed in YND+1% glycerol and induced with 1% methanol on the second day of growth. The cells are opened mechanically on a Mini Bead-Beater (pink) or opened with the chemical reagent LTAB (blue).

FIG. 20. Left: Native-PAGE on a homogenous polyacrylamide gel. Right: Native-PAGE on an 8-25% gradient polyacrylamide gel (right). The gels are loaded in the same order: Lane 1: Raw extract from Aspergillus Niger. Lane 2: Fraction III. Lane 3: Fraction II. Lane 4: Algal α-1,4-glucan lyase purified from Aspergillus Niger. Lane 5: Fraction I. Lane 6: Raw extract from H. polymorpha. The gels are stained with PhastGel Blue R.

Figure 21:
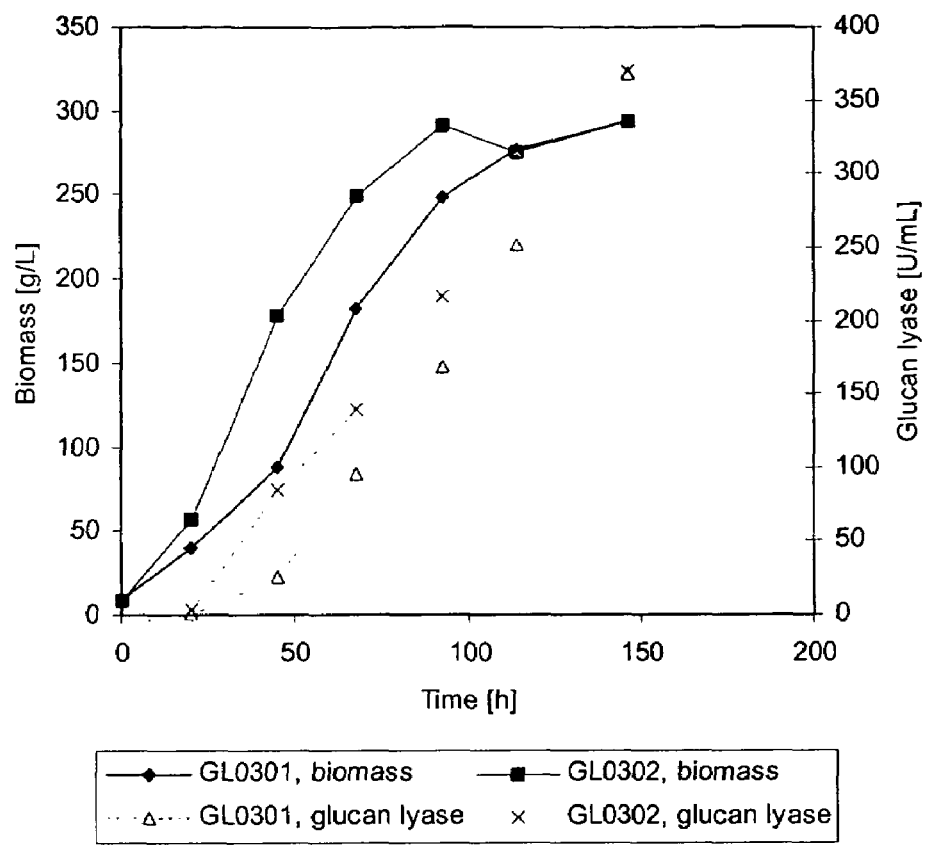
FIG. 21 shows a graph.

FIG. 21 shows the development of biomass concentration (g wet weight pr L) and glucan lyase activity in the two fermentations described in Example 26. The glucan lyase activity is based on the substrate containing glycogen at pH 4.

EXAMPLES

Materials and Methods for Examples 1 to 23

Chemicals

All chemicals used were of analytical reagent grade. Lecithin (3-sn-phosphatidylcholine) was commercially available as Stempur PM from Stem (Germany). Pronase E (a proprietary name for a mixture of various exo- and endo-peptidases, obtained from Streptomyces griseus, that is able to hydrolyse virtually any protein almost completely to free amino acids). Lysolecithin (lysophatidylcholine), D-glucose, o-dianisidine, peroxidase (P-8125), capric acid (decanoic acid), saponin (any member of a large group of glycosides, widely distributed in plants, that are powerful surfactants) and CTAB (cetyltrimethylammonium bromide also known as hexadecyltrimethylammonium bromide) (H-5882) were all from Sigina Chemical Co., USA. Methanol (HPLC) was from Lab-Scan Ltd. Hydrogen peroxide and Triton X-100 (a proprietary name for polyethoxylated octylphenol) were from Merck, Germany. Emulsifier YN also commercially known as Palsgaard 4445 was from Palsgaard, Denmark. The quaternary ammonium compounds such as LTAB (lauroyltrimethylammonium bromide), Cetrimide-40 (also known as cetrimidum which is a detergent disinfectant consisting of a mixture of alkylammonium bromides, principally CTAB), CTAB (cetyltrimethylammonium bromide), STAB (stearoyl trimethyl ammonium bromide), MTAC (myristyl trimethyl ammonium chloride), CTAC (Cetyl Trimethyl Ammonium Chloride), STAC (stearoyl trimethyl ammonium chloride) were all from FeF, Denmark. Rodalon comprises about 9.5% (95 g/l) alkyldimethylbenzylammonium chloride $(C_{12}H_{25}N(CH_3)_2C_7H_7Cl)$ was obtained from Superfos Biosector, 2950 Vedbaek, Denmark. Alkyldimethylbenzylammonium chloride is also known as benzalkoniumchloride. The emulsifier Sodium Lauroyl Lactylate (SLL) was from Danisco Cultor, Grindsted, Denmark.

Yeast Fermentation

The cultivation of yeast was performed in a 6 L or a 100 L fermentor according to Rhein Biotech fermentation manual for 10 L scale.

Example 1

Assembly of a Synthetic, Codon Optimized HOX Gene

Gene Design

The nucleotide sequence of the native HOX gene was altered resulting in a synthetic gene. The synthetic HOX gene (FIG. 6) was designed so that the codon usage was precisely matched to the known codon preferences of biotechnologically relevant yeasts such as *Pichia* sp., *Hansenula* sp., *Kluyveromyces, Yarrowinia, S. Pombe* in order to facilitate high level production in these organisms. The gene was divided into three separately assembled and/or cloned fragments. The sub-assemblies, designated as 5' proximal half were comprised of the following oligonucleotides as set out in FIG. 5 as complementary pairs: HOX1a/HOX2b (SEQ ID NOS: 1 and 2), HOX3a/HOX4b (SEQ ID NOS: 3 and 4), HOX5a/HOX6b (SEQ ID NOS: 5 and 6), HOX7a/HOX8b (SEQ ID NOS: 7 and 8), HOX9a/HOX10b (SEQ ID NOS: 9 and 10); 3' distal half A using primers 1-6 and 3' distal half B using primers 6-10.

5' Proximal Synthetic HOX Gene

The 5' proximal half of the synthetic HOX gene was synthesized using ten oligonucleotides HOX1A to HOX10B. The oligonucleotides having lengths ranging from 100-120 base pairs were used as primers (concentration=0.1 µM each) in a hot start PCR reaction of 100 µL (using the thermostable DNA polymerase Pwo (Boehringer). Hot start was performed by heating the mixture of oligonucleotides, buffer, MgSO$_4$ to 90° C. before dNTP (250 µM) and Pwo polymerase (2.5 units) was added. 40 cycles of PCR using the PCR profile: 94° C. for 30 seconds, 57° C. for 1 minute and 72° C. for 1 minute. A 10 minute elongation step at 72° C. was included at the end of the 40 cycles. Analysis of the products from this PCR in agarose gel electrophoresis showed a smear of DNA bands ranging in size from 100 to 850 base pairs. The first PCR was reamplified using 2 ul from the above reaction as template and the flanking primers (1 µM each) HOX1A and HOX 10B. The reaction contained 200 µM dNTP, 2.5 mM MgCl$_2$ and 2 units of AmpliTaq® (Perkin-Elmer Cetus). The PCR conditions were: 94° C. for 2 minutes, then 30 cycles of PCR with the profile 94° C. for 30 seconds, 60° C. for 1 minute and 72° C. for 45 seconds. A 10 minutes elongation step at 72° C. was included at the end of the above reaction. Analysis of the second PCR product by agarose gel electrophoresis showed the presence of a 850 bp DNA band which was subsequently purified from the gel and cloned into the vector pCR® (Invitrogen).

3' Distal Synthetic HOX Gene

Ten primers of lengths ranging from 90-126 base pairs were designed to synthesize the distal part of the HOX gene. The primers contained overlapping (complementary) regions of 16-21 base pairs with a calculated melting temperature of approximately 60° C. The distal part of the HOX gene was synthesized as two fragments (A & B), each with a size of 530 base pairs. Two PCR reactions were performed using 6 primers at a time. The PCR reaction 1 contained primers 1-6 and PCR reaction 2 contained primers 5-10. The PCR amplification reactions were performed using 0.1 µM of each of the primers, 250 µM each dNTP, 2 mM MgSO$_4$ and 2.5 units of Pfu DNA polymerase from *Pyrococcus furiosus* (Strategene) in a reaction volume of 100 µl. The cycling parameters for the 2 PCR reactions using Pfu DNA polymerase included a 1 minute denaturation at 95° C. followed by 30 cycles of PCR: 94° C. for 1 minute, 55° C. for 1 minute and 72° C. for 1 minute. This was followed by an elongation step at 72° C. for 3 minutes. Analysis of the PCR products from the two PCR reactions by agarose gel electrophoresis showed in both cases, the synthesis of one specific DNA band of the correct size of approximately 530 bps in length. The PCR products were cloned in pCR®-Blunt vector (Invitrogen). The cloned partial synthetic HOX genes were sequenced using primers flanking the multiple cloning sites (M13 reverse primer and T7 promoter primer). The sequencing results verified that the synthesized partial genes contained the correct sequence.

Assembly of the Final Codon-optimized HOX Gene

The three parts of the synthetic HOX gene were combined by ligation of the gel purified DNA fragments comprising of the Ncol/PvuII 5' proximal HOX, the 3' distal PvuII/SpeI HOX fragment A and fragment B cut with SpeI/NotI. The complete, codon optimized synthetic HOX gene (FIG. 6) was assembled into the *Hansenula* expression vector, which was developed to mediate the expression and secretion of foreign proteins from *Hansenula*. The expression vector is based upon the formate dehydrogenase promoter (FMD), the MOX terminator, with and without a yeast secretion signal.

Results 1

Expression of the Recombinant HOX in *H. polymorpha*

Table 1 shows the various HOX/secretion fusion constructs which were inserted as Eco RI/Not I blunt fragments into the multiple cloning site of the *H. polymorpha* expression/integration vector. The different signal sequences were derived from the glucoamylase gene from *Schwanniomyces occidentalis*, α-factor mating type gene from *Saccharomyces cerevisiae* and the TAKA-amylase from *Aspergillus oryzae*. A NcoI/NotI HOX construct without a signal sequence was also cloned into the vector.

TABLE 1

The term mutant synthetic relates to a putative KEX 2 protease cleavage site $R_{331}$-$K_{332}$ to $R_{331}$-$P_{332}$.

| Name of Clone | signal sequence | HOX | Fusion junction |
|---|---|---|---|
| 1. DK 1 | glucoamylase | wildtype synthetic | SAIQA MATLP (SEQ ID NOS 24 and 25) |
| 2. DK 2 | glucoamylase | wildtype synthetic | SAIQA ATLP (SEQ ID NOS 24 and 26) |
| 3. DK 3 | α-factor | wildtype synthetic | KREAEA MATLP (SEQ ID NOS 27 and 25) |
| 4. DK 4 | α-factor | wildtype synthetic | KREAEA ATLP (SEQ ID NOS 27 and 26) |
| 5. DK 5 | α-factor | mutant synthetic | KREAEA MATLP (SEQ ID NOS 27 and 25) |
| 6. DK 6 | α-factor | mutant synthetic | KR MATLP (SEQ ID NO:25) |
| 7. DK 7 | TAKA amylase | mutant synthetic | APALA MATLP (SEQ ID NOS 28 and 25) |
| 8. DK 8 | No signal sequence | wild type synthetic | none - MATLP (SEQ ID NO:25 |

Example 2

Transformation and Passaging

The different HOX expression plasmids were used to transform the uracil auxotrophic *H. polymorpha* strain RB11 to uridine prototrophy. The HOX transformants harbouring the different expression plasmids were cultivated under selective conditions for 30 generations to amplify the plasmid DNA and allow integration into the genome. The transformants were grown on complete non-selective medium for 20 generations. In addition to the selection, PCR and southern analysis were used to characterize the transformants.

Copy Number Determination of the Integrated Heterologous DNA

The genomic DNA of the untransformed host strain and the various recombinant isolates of a particular HOX construct were digested with the restriction enzymes, Asp718/NcoI. The restricted DNA was separated on 0.8% agarose gels, transferred to membrane (nitrocellulose) and hybridized to a $^{32}$P-labelled fragment of the cloned FMD promoter. The hybridization pattern reveals two signals, one for the genuine single copy 1.4 kb FMD gene and one originating from the slightly smaller heterologous fusion. A series of dilutions enabled the estimation of the signal intensity of the integrated DNA compared to the intrinsic single copy control.

Results 2

Screening for HOX Expression

Transformants were grown in 3 mL tube cultures and cultivated under derepressing conditions by supplementing the medium with 1% glycerol. HOX expression was analysed by SDS-PAGE analysis of cultures from glycerol fermentation. Western blot analysis using a polyclonal HOX antibody was used to detect the presence of HOX protein. Table 2 shows the characteristics of selected transformants expressing HOX.

TABLE 2

Characteristics of selected transformants expressing HOX.

| Transformant | Copy Number | N-terminus | Localization of expression | HOX Activity |
|---|---|---|---|---|
| DK1-49 | ≈10 | unprocessed signal peptide | soluble & insoluble fractions | none |
| DK 2II-1 | ≈20 | unprocessed signal peptide | soluble & insoluble fractions | none |
| DK3II-4 | ≈20 | unprocessed signal peptide | soluble & insoluble fractions | none |
| DK4-39 | ≈10 | unprocessed signal peptide | soluble & insoluble fractions | none |
| DK5-13 | ≈30-40 | unprocessed signal peptide | soluble & insoluble fractions | none |
| DK6-16 | ≈10 | unprocessed signal peptide | soluble & insoluble fractions | none |
| DK7-1 | ≈10 | unprocessed signal peptide | soluble & insoluble fractions | none |
| DK8-1 | ≈2-3 | same as mature | soluble & insoluble fractions | active |
| DK8-27 | ≈20 | same as mature | soluble & insoluble fractions | active |
| DK8-27* Kan II3-mut25 | ≈20 | same as mature | extracellular intracellular | active active |
| DK8-27Kan* IV2-mut301 | ≈20 | same as mature | extracellular intracellular | active active |

*The strain DK8-27 was subjected to chemical mutagenesis (NTG-nitrosoguanidine).

Example 3

Localisation of Recombinant HOX in *H. polymorpha*

For immunofluorescence microscopy of recombinant *H. polymorpha*, cells were precultured in Yeast Nitrogen Base (YNB)+glucose to a density of $10^8$ cells/ml. To induce expression, $3\times10^8$ cells were shifted to 100 mL shake flask cultures supplemented with YNB+1% glycerol. After 1, 2 or 3 days of growth under derepressing condition $5\times10^8$ cells were fixed by a combined para-formaldehyde (4%) and glutaraldehyde (0.2%) treatment (Hagen and Hyam, 1988). After three washes with 1 mL of PEM (100 mM Pipes, 1 mM EGTA, 1 nM MgSO$_4$, pH 6.9), the cell walls were partially removed in PEMS (PEM+1 M sorbitol) supplemented with 0.5 mg/mL Zymolyase-100T. After approximately 60 minutes of digestion, cells were shifted to PEMS+1% Triton X-100, incubated 30 seconds and washed three times with 0.5 mL PEM. To quench unreacted glutaraldehyde cells were resuspended in PEM+1 mg/mL sodium borohydride. Immediately after this, cells were washed twice in PEM, resuspended in PEMBAL (PEM+1% BSA (globulin free), 1 mM lysine hydrochloride, 0.1% NaN$_3$), and incubated on a rotating wheel for 30 minutes. 25% of the cell suspension, equalling $10^8$ cells, was supplemented with 10 µg/ml of affinity purified polyclonal anti-HOX antibodies and incubated overnight at room temperature. After three washes in 0.5 mL PEMBAL, cells were suspended in PEMBAL, and incubated 5-20 hours in the dark with 0.5% FITC-conjugated goat anti-rabbit antibodies (Sigma). After wash in PEMBAL, the cells were washed once in PBS, once in PBS+0.2 µg/mL diamidinophenylindole (DAPI) and finally resuspended in PBS+0.1% NaN$_3$. For microscopic observation, small samples of cell suspensions were dried onto poly-L-lysine coated coverslips and inverted into drops of 100% glycerol containing 1 mg/mL para-phenylene diamine. Cells were examined with a Zeiss microscope equipped for indirect immunofluorescence at 1.000× and images were captured by a CCD camera (MicroMAX Kodak) and processed using MetaMorph software.

Results 3

Immunofluorescence microscopy of the DK8-27 transformant revealed that the recombinant HOX protein primarily localises to the periphery of the cell as aggregates (FIG. 7b). Combined with the biochemical data, these results indicate that HOX to some extent may be a membrane associated protein (as opposed to a substantially membrane bound protein). It is most likely that HOX localises to the plasma membrane in *H. polymorpha*. Also, in the DK8-27 mut25 strain, which is derived from DK8-27, HOX is associated with the plasma membrane (FIG. 7c). The protein, however, does not accumulate in aggregates but is more uniformly distributed. When fused to various leader peptides HOX accumulates in huge intracellular aggregates (FIG. 7d)

Example 4

Extraction of HOX from Recombinant *Hansenula* Cells by Means of Different Detergents and Proteases The experiment was carried out by using 5.0 mL cell suspension (cells+supernatant) in a 15 mL centrifuge tube (HOX9926-7, 317 g cells/L wet weight, 0.3 U/mL extracellular HOX activity). Cells were separated by centrifugation at 4000 g for 10 min. For permeabilisation experiments, the supernatant was then supplemented with either, CTAB, CTAB+Pronase E, Pronase E, Tween 20 (a proprietary name for polyoxyethylene sorbitan monolaurate) and Tween 80 (a proprietary name for sorbitan monooleate). The cells were then resuspended in 4.0 mL supernatant and incubated for 23 hours at 25° C. (500 rpm). In order to examine the effect of time with CTAB, the cells in one of the tubes were only incubated for 7 min at 25° C. in 4 mL 0.4% CTAB. The cells were then separated by centrifugation. The cells were then re-suspended again in the original supernatant without CTAB added and then incubated for 23 hours as above. After incubation, the extracellular HOX in the cell-free extracts was measured by the HOX assay.

Assay Method for Determination of HOX Activity (HOX Assay)

HOX activity was estimated by the assay of Sullivan and Ikawa (1973). The assay was scaled down to be run in microtiter plates.

Principle

The HOX assay is based on the measurement of hydrogen peroxide generated in the oxidation of glucose. The hydrogen peroxide oxidizes o-dianisidine in presence of peroxidase (POD) to form a dye.

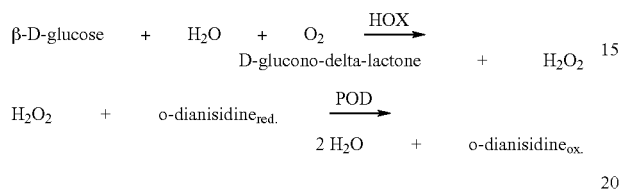

Reagents 1. 100 mM phosphate buffer, pH 6.3
2. 100 mM D-glucose in 100 mM phosphate buffer, pH 6.3
3. o-Dianisidine, 3.0 mg/mL in distilled water Peroxidase, 0.10 mg/mL in 100 mM phosphate buffer, pH 6.3

Assay

120 µl reagent 1

150 µl reagent 2

10 µl reagent 3

10 µl reagent 4 and 10 µl enzyme solution (in proper dilution)

The assay is performed in a microtiter plate. The reaction is initiated by the addition of enzyme solution. The mixture is incubated at 25° C. for 10 min with shaking. The blank run contains all the components with water instead of enzyme solution. The formation of the dye is measured in a microtiter plate reader at 405 nm. The linearity of the reaction is checked by using a kinetics programme on the microplate reader.

Hydrogen Peroxide Standard Curve

A hydrogen peroxide standard curve is constructed by using varying concentrations of fresh $H_2O_2$.

One unit of enzyme activity is defined as the amount of enzyme which produces 1 µmol of $H_2O_2$ per min at 25° C.

Results 4

The data presented in Table 3 shows that CTAB is very efficient in extracting HOX. CTAB is also much more efficient than Tween 20 and Tween 80. There is no significant benefit of adding a protease. Very interestingly CTAB exerts its positive effect even when used only for a 7 min preincubation, this indicates that CTAB very quickly binds to and permeabilizes the *Hansenula* cell wall. This is supported by analysis of the cell free supernatant for CTAB (see below) which shows that only 50-100 ppm out of 4000 ppm CTAB added is present in the cell free supernatant.

A comparison of the sediment in the centrifuge tubes for each test agent also indicates that the packed cell volume of the CTAB treated cells is smaller than the volume of the control cells or cells treated with detergents other than CTAB. This shrinkage of the cells indicates that the cells have indeed been permeabilized and emptied for some of their soluble content.

TABLE 3

Effect of detergent, detergent in combination with protease and preincubation on the extraction of intracellular HOX.

| Test | HOX activity % |
|---|---|
| Control | 100 |
| 0.4% CTAB | 4600 |
| 0.4% CTAB + Pronase E (400 PU) | 5000 |
| 0.4% CTAB + Pronase E (800 PU) | 4800 |
| Pronase E (400 PU) | 120 |
| 0.4% Tween 20 | 140 |
| 0.4% Tween 80 | 140 |
| Pre-incubation in 0.4% CTAB for 7 min | 5100 |

Example 5

Extraction of HOX Using CTAB and Benzalkonium Chloride (BAC)

The experiment was carried out by using a 5.0 mL cell suspension (cells+supernatant) in a 15 mL centrifuge tube (HOX9959, Mut 45). The cell suspension was then supplemented either with CTAB (from a 10% CTAB stock solution) or benzalkonium chloride (Rodalon, 9.5% benzalkonium chloride) and incubated for 22 hours at 25° C. (200 rpm). After incubation, extracellular HOX (cells were removed by 10 min centrifugation at 4000 g) was measured by HOX assay.

Results 5

The data presented in Table 4 indicate that benzalkonium chloride (3AC) is very effective in releasing the HOX enzyme from the cells.

TABLE 4

Effect of CTAB and Benzalkonium chloride (BAC) on HOX release from cells.

| Test | HOX activity, % |
|---|---|
| Control | 100 |
| 0.4% CTAB | 1300 |
| 0.08% BAC | 2500 |
| 0.17% BAC | 2300 |
| 0.50% BAC | 2300 |
| 0.70% BAC | 2100 |
| 0.83% BAC | 1700 |
| 1.00% BAC | 1600 |

Example 6

Extraction of HOX by CTAB Combined with Salts and at Different Temperatures

In order to examine the mechanism of the CTAB effect, CTAB was combined with chaotrophic and nonchaotrophic salts. Five mL cell suspension (cells+supernatant) was added to a 15 mL centrifuge tube (HOX9926-7, 317 g cells/liter wet weight, 0.3 U/mL extracellular HOX activity). Cells were separated by centrifugation at 4000 g for 10 min. The supernatant was then supplemented with either CTAB, CTAB+ NaCl, CTAB+urea, CTAB+ammonium sulphate, or the nonionic detergent, octyl-glucoside. The cells were then re-suspended in 4.0 mL supernatant and incubated for 26 hours at 25° C. (500 rpm). In this experiment, the effect of shaking and temperature was also investigated. After incubation, the cell-free extract was used to estimate HOX activity using the HOX assay as outlined in Example 4.

Results 6

The results are shown in Table 5. It is clear that shaking is not necessary in order to have extraction of HOX in the presence of CTAB. There is a clear temperature effect, meaning that extraction at 4° C. results in only half the activity extracted at 25° C. The addition of sodium chloride and ammonium sulphate both decrease the effect of the CTAB treatment, which may indicate that the ionic nature of CTAB is important. The addition of urea had a less drastic effect but still reduced the amount of extracted HOX to approximately half of the amount extracted with 0.4% CTAB. Although urea is non-ionic, it may interfere with hydrophobic interaction. Urea has been reported in the prior art as a means of permeabilizing *Pichia* cells for extraction of lipophilic proteins (Craig 1987). The non-ionic detergent octyl glucoside has no significant extracting effect.

TABLE 5

Effect of detergent, detergent in combination with salt, shaking, and temperature on the extraction of intracellular HOX.

| Test | HOX activity, % |
|---|---|
| Control | 100 |
| 0.4% CTAB | 6700 |
| 0.4% CTAB, without shaking | 7700 |
| 0.4% CTAB, without shaking, at 4° C. | 2800 |
| 0.4% CTAB + 1.0M NaCl | 1900 |
| 0.4% CTAB + 1.0M urea | 3600 |
| 0.4% CTAB + 1.0M ammonium sulphate | 2300 |
| 0.2% octyl-glycoside | 130 |
| 0.4% octyl-glycoside | 190 |

Example 7

Determination of CTAB and LTAB by LC-ESI-MS in Cell Extracts Containing HOX

The samples of extracted HOX from Example 5 were analyzed for their content of CTAB by means of LC-ESI-MS on a Hewlett-Packard 1100 HPLC-MS system consisting of the following units:

(a) Binary gradient pump, HP 1100
(b) Autosampler, HP 1100,
(c) Thermostated Column Compartment, HP 1100
(d) Mass Selective Detector, HP 1100
(e) Chromatographic data system, HP ChemStation, Version 6.01

The system was equipped with a Zorbax Eclipse® XDB-C8, 5 µM, 150×4.6 mM id. (Hewlett-Packard) column. Column temperature was 25° C.

The chromatographic conditions were a mobile phase consisting of two solvents. Solvent A: 1 mM $NH_4OAc$/Water, solvent B: 1 mM $NH_4OAc$/Methanol. The column was run with isocratic conditions (that is, using conditions where the composition of the eluant is maintained constantly during the chromatographic period): 5% A+95% B, with a solvent flow rate of 0.80 mL/min and an injection volume of 10 µL. The samples were injected directly.

The mass spectrometric conditions were with the following spray chamber settings:

Ionisation mode: Electrospray in positive mode
Drying gas ($N_2$) temperature: 350° C.
Drying gas flow rate: 6.0 l/min
Nebuliser pressure: 60 psi
Capillary voltage: −4000 Volts
Fragmentor voltage: 100 Volts The detector settings were the following: SIM parameters: m/z 284.1 (hexadecyltrimethylammonium cation). A stock solution containing 500 µg CTAB/mL water (concentration index 1000) was diluted with water to obtain standard solutions with the following concentration indices: 300-100-30-10. To the samples was added 0.4% CTAB which would give 4000 pg/mL if all the CTAB was present in the extract.

The analysis method for the quaternary ammonium compounds was optimised by using a different column, and by using different mobile phase. Two 90 L scale fermentations (Vest0002b with a biomass concentration of 314 g/L wet cells and Vest0003b with a biomass concentration of 332 g/L wet cells) were added LTAB to a concentration of 0.20% (w/v), and HOX was extracted for 24 h. A sample from each fermentation was centrifuged at 10000 g for 10 minutes, and the resulting supernatants were withdrawn for LTAB analysis. The following method was used to quantify the LTAB content in the supernatants by means of LC-ESI-MS on a Hewlett-Packard 1100 HPLC-MS system consisting of the following units:

(a) Binary gradient pump, HP 1100
(b) Autosampler, HP 1100,
(c) Thermostated Column Compartment, HP 1100
(d) Mass Selective Detector, HP 1100
(e) Chromatographic data system, HP ChemStation, Version 6.01

The system was equipped with a PLRP-S, 100 Å, 5 µm, 250×4.6 mM id. (Polymer Laboratories) column. Column temperature was 25° C.

The chromatographic conditions were a mobile phase consisting of 0.1% heptafluorobutyric acid in methanol. The column was run with a solvent flow rate of 1.00 mL/min and an injection volume of 5 µL. The samples were diluted 25 fold with methanol and filtered through Gelman GHP Acrodisc 13 mM Minispike 0.45 µM before injection.

The mass spectrometric conditions were with the following spray chamber settings:

Ionisation mode: Electrospray in positive mode
Drying gas ($N_2$) temperature: 350° C.
Drying gas flow rate: 13.0 L/min
Nebuliser pressure: 60 psi
Capillary voltage: −4000 Volts
Fragmentor voltage: 150 Volts The detector settings were the following: SIM parameters: m/z 228.1 (lauroyltrimethylammonium cation). A stock solution containing 250 µg LTAB/mL methanol (concentration index 1000) was diluted with methanol to obtain standard solutions with the following concentration indices: 400-200-120-80-36-10.8-5.4-2.16-0.864.

Results 7

It is clear from Table 6 that the level of CTAB in cell extracts containing the HOX enzyme is much lower than the amount added to the cells. This is explained by the binding and therefore immobilization of the CTAB to the yeast cell walls. This means that the resulting HOX enzyme only contains a very low level of CTAB.

TABLE 6

Content of CTAB in the extracted HOX supernatants from Example 6.

| Test | [1]CTAB concentration, μg/mL |
|---|---|
| Control no CTAB added | 21 |
| 0.4% CTAB | 115 |
| 0.4% CTAB, without shaking | 52 |
| 0.4% CTAB, without shaking, at 4° C. | 35 |
| 0.4% CTAB + 1.0M NaCl | 212 |
| 0.4% CTAB + 1.0M urea | 235 |
| 0.4% CTAB + 1.0M ammonium sulphate | 246 |

[1]Analysed by the first method.

The results obtained on LTAB in the supernatant (see Table 6A) show that only about 27% of the added LTAB is found in the cell free fraction. This result shows the same tendency as the results with CTAB in Table 6.

TABLE 6A

Content of LTAB in the supernatants extracted from fermentation Vest0002b and Vest0003b from Example 6.

| Fermentation | LTAB added [μg/mL] | [1]LTAB in cell free extract [μg/mL] |
|---|---|---|
| Vest0002b | 2000 | 538 |
| Vest0003b | 2000 | 550 |

[1]Analysed by the optimised method

Example 8

Effect of Temperature on Time End Efficiency of HOX Extraction by CTAB

The effect of temperature on time end efficiency of HOX extraction by CTAB was examined on a *Hansenula* sample: Mut 45, HOX9949, 282 g/L, 2.6 U/mL.

To 5 mL of ferment (cells+supernatant) in a centrifuge tube, either 0.2% or 0.4% CTAB (from a 10% CTAB solution) was added. The tubes were incubated at 25, 30, 35 and 40° C., respectively (200 rpm). At the indicated times samples were taken and after centrifugation for 5 min at 10000 g, the supernatant was assayed for HOX activity. The results are shown in Table 7.

TABLE 7

Time course of HOX extraction from *H. polymorpha* at different temperatures.

| Extraction conditions | Extracted HOX [U/mL] | | | | |
|---|---|---|---|---|---|
| | 4 h | 8 h | 24 h | 31 h | 48 h |
| 25° C., 0.2% CTAB | 5.1 | 7.5 | 31 | 36 | 44 |
| 25° C., 0.4% CTAB | 5.9 | 9.2 | 25 | 29 | 37 |
| 30° C., 0.2% CTAB | 6.8 | 15 | 38 | 45 | 44 |
| 30° C., 0.4% CTAB | 7.4 | 15 | 36 | 40 | 42 |
| 35° C., 0.2% CTAB | 6.4 | 16 | 36 | 44 | 41 |
| 35° C., 0.4% CTAB | 8.2 | 15 | 33 | 37 | 23 |
| 40° C., 0.2% CTAB | 16 | 27 | 44 | 43 | 32 |
| 40° C., 0.4% CTAB | 17 | 28 | 56 | 59 | 40 |

Results 8

It is clear that CTAB extraction is dependent on the temperature and that a faster extraction can be achieved by using a higher temperature. This is, however a parameter which has to be balanced with the stability of the extracted protein. In this experiment no significant difference seems to exist between using 0.2% or 0.4% CTAB. However, this depends on the cell concentration in the specific experiment.

Example 9

HOX Extraction with Different Quaternary Ammonium Compounds

Several quaternary ammonium compounds were tested with respect to extraction of the intracellular HOX enzyme from *Hansenula polymorpha*. A sample of fermentation broth was withdrawn from a 6 L scale fermentation where the biomass concentration was approximately 340 g wet weight per L. One mL of a 4% (w/v) solution of each of the quaternary ammonium compounds listed in Table 8 was added to 9 mL of fermentation broth in plastic tubes. After 24 h of incubation at 25° C. at 200 RPM the tubes were centrifuged 10 min. at 12000 g. The supernatants were analysed for HOX activity using the HOX assay as previously described.

The time course of HOX extraction was studied with CTAB, LTAB and CTAC. A fermentation sample containing 280 g wet weight of *Hansenula polymorpha* per L was withdrawn from the fermentor. A 4% (w/v) solution of CTAB, LTAB and CTAC was added to a final concentration of 0.2 or 0.4% (w/v) to plastic tubes containing 9 mL of fermentation broth. After 0, 7, 17, 24, and 48 h of incubation at 25° C. at 200 RPM the tubes were centrifuged 10 min. at 12000×g. The supernatants were analysed for HOX activity using the HOX assay as previously described.

The extracting effect of LTAB was tested on the *Pichia pastoris* strain #349 that produces HOX intracellularly. A sample of fermentation broth was withdrawn from a 6 L scale fermentation where the biomass concentration was approximately 232 g wet weight per L. Nine mL of fermentation broth was added to plastic tubes together with 0 (control) or 180 μL of a 10% (w/v) solution of LTAB. After 24 h of incubation at 30° C. at 20 RPM the tubes were centrifuged 5 min. at 9000 g. The supernatants were analysed for HOX activity using the HOX assay as previously described.

Results 9

HOX could be extracted with all the tested quaternary ammonium compounds (see Table 8) when added to a fermentation sample in a final concentration of 0.4% (w/v). After 24 h of incubation at 25° C., LTAB was superior to the other tested compounds with respect to extraction of HOX. The amount of HOX extracted seemed to decrease with increasing chain length of the quaternary ammonium compound.

The time course of HOX extraction with CTAB, LTAB or CTAC is shown in Table 9. It is clear that both incubation time and the concentration of the extraction reagent influences the amount of HOX activity extracted. LTAB is found to be the best extraction reagent at all analysed incubation times which is consistent with the results shown in Table 8. The extraction of HOX with LTAB seems to proceed at a slower pace at a concentration of 0.2% (w/v) LTAB, than at a concentration of 0.4% (w/v) LTAB. There seems to be little difference between using 0.2 or 0.4% (w/v) CTAB in terms of extraction of the HOX enzyme.

TABLE 8

Extraction of HOX from *Hansenula polymorpha* with various quaternary ammonium compounds.

| Trade name | [a]Methylene groups in chain | Counter ion | Extracted HOX activity normalised with extracted amount with LTAB | [b]Standard deviation |
|---|---|---|---|---|
| LTAB | 11 | bromide | 100 | 7 |
| Cetrimide-40 | 13 | bromide | 62 | 6 |
| Cetrimide-40 dissolved in butanol | 13 | bromide | 65 | 1 |
| CTAB | 15 | bromide | 53 | 10 |
| STAB | 17 | bromide | 38 | 11 |
| MTAC | 13 | chloride | 71 | 2 |
| CTAC | 15 | chloride | 67 | 7 |
| STAC | 17 | chloride | 54 | 10 |
| *Pichia pastoris* LTAB | 11 | bromide | 3000[c] | not determined |
| *Pichia pastoris* Control | — | bromide | 100[c] | not determined |

The extracellular HOX levels in the fermentation broth before addition of extraction reagents was about 9% of the HOX activity extracted with LTAB after 24 h.
[a]The compounds are all of the structure: $CH_3-(CH_2)_n-N(CH_3)^+_3$ with chloride or bromide as counter ion.
[b]All experiments were performed in duplicate
[c]The results from *Pichia pastoris* were normalised with respect to extracted HOX in the control tube without any LTAB added. The extracellular HOX level in the fermentation before start of the extraction was about 24% of the extracted level in the control, i.e. the plastic tube without any LTAB added.

TABLE 9

Time course of extraction of the HOX enzyme with CTAB, LTAB, and CTAC.

| Time [h] | 0.4% (w/v) | | | 0.2% (w/v) | |
|---|---|---|---|---|---|
| | CTAB | LTAB | CTAC | CTAB | LTAB |
| 0 | 3 ± 1, n = 3 | 6 ± 1, n = 3 | 4 ± 1, n = 3 | 2 | 5 |
| 7 | 9 | 25 | 8 | 8 | 15 |
| 17 | 28 | 74 | 27 | 38 | 49 |
| 24 | 36 ± 5, n = 3 | 83 ± 8, n = 3 | 38 ± 6, n = 3 | 43 | 65 |
| 48 | 65 ± 8, n = 3 | 100 ± 25, n = 3 | 64 ± 20, n = 3 | 65 | 78 |

The extracellular HOX level in the fermentation broth before addition of extraction reagents was about 4% of the HOX activity extracted with 0.4% (w/v) LTAB after 48 h.

Values are given ±1 standard deviation. n: the number of experiments.

All values are normalised to the extracted levels with 0.4% (w/v) LTAB after 48h.

Example 10

Comparison Between CTAB and Other Emulsifiers for Extraction of HOX

It is known that lysolecithin (lysophosphatidylcholine) can permeabilize at least mammalian cells, with selective release of macromolecules. In order to test the effect of lysolecithin and a number of other emulsifiers and short chain fatty acids, their ability to extract HOX was examined and compared with CTAB.

Five mL of cell suspension (cells+supernatant) was added to a 15 mL centrifuge tube (HOX9910B, 305 g cells/liter wet weight, 1.6 U/ml extracellular HOX activity). Cells were separated by centrifugation at 4000 g for 10 min. Cells were then re-suspended in 4.0 mL 25 mM citric acid, pH 6.3 supplemented with either CTAB, emulsifiers SLL, YN, capric acid, lysolecithin, or lecithin. The cells were then incubated for 20 hours at 25° C. (500 rpm).

Results 10

After incubation, the level of HOX activity in the cell free extract was measured by the HOX assay. The data presented in Table 10 indicate that the tested emulsifiers other than CTAB are only capable of releasing very low levels of active enzyme. The results also indicate that CTAB is capable of activating latent enzyme in the supernatant, possibly by releasing the enzyme from membrane bound fragments.

TABLE 10

Effect of detergent, Emulsifier and Phospho-lipids on the extraction of HOX.

| Test | HOX activity, % |
|---|---|
| Control (Cells and buffer) | 100 |
| 0.4% CTAB | 1100 |
| 0.5% emulsifier SSL | 160 |
| 1.0% emulsifier SSL | 140 |
| 0.5% emulsifier YN | 130 |
| 1.0% emulsifier YN | 130 |
| 0.5% capric acid | 120 |
| 1.0% capric acid | 140 |

TABLE 10-continued

Effect of detergent, Emulisifier and Phospho-lipids on the extraction of HOX.

| Test | HOX activity, % |
| --- | --- |
| 0.4% lyso-lecithin | 260 |
| 0.4% lecithin | 140 |
| Control (Cells + supernatant) | 170 |
| Cells + supernatant + 0.4% CTAB | 1900 |

Example 11

Comparison Between CTAB and Saponin for Extraction of HOX

In order to establish whether saponin works like digitonin, the effect of saponin on the extraction of the HOX enzyme from *Hansenula* was examined.

The experiment was carried out with 5.0 mL cell suspension (cells+supernatant) in a 15 mL centrifuge tube (HOX190799, 340 g cells/liter wet weight, 0.5 U/mL extracellular HOX activity). Cells were separated by centrifugation at 4000 g for 10 min. The cells were then re-suspended in 4.0 mL of supernatant which was supplemented with either CTAB, or saponin, or re-suspended in 25 mM citric acid, pH 6.3 supplemented with either CTAB, or saponin.

In order to confirm that the measured HOX activity in the cell-free extract (after treatment with CTAB) is actually the result of extraction and not just the result of HOX activation in the supernatant (it could be that HOX already exists in the supernatant but is inactive), the cell-free supernatant (after supplementation with CTAB or saponin) was also incubated and analysed for HOX activity. The tubes were incubated for 19 hours at 25° C. (500 rpm). After incubation, the extracellular HOX in the cell-free extract was measured by the HOX assay.

Results 11

The results in Table 11 show that saponin has a negligible ability to extract HOX from the cells. In addition, there is no indication of HOX activation neither by saponin nor by CTAB.

TABLE 11

Comparative HOX extraction/activation by using different permeabilising 1530 agents.

| Test | HOX activity, % |
| --- | --- |
| Control 0 (cells + supernatant) | 100 |
| 0.2% CTAB (cells + supernatant) | 1200 |
| 0.4% CTAB (cells + supernatant) | 3100 |
| 0.2% Saponin (cells + supernatant) | 150 |
| 0.4% Saponin (cells + supernatant) | 140 |
| 0.8% Saponin (cells + supernatant) | 140 |
| Control 1 (cells + buffer) | 100 |
| 0.2% CTAB (cells + buffer) | 3100 |
| 0.4% CTAB (cells + buffer) | 7700 |
| 0.2% Saponin (cells + buffer) | 230 |
| 0.4% Saponin (cells + buffer) | 230 |
| 0.8% Saponin (cells + buffer) | 230 |
| Supernatant + 0.2% CTAB | 80 |
| Supernatant + 0.4% CTAB | 80 |
| supernatant + 0.2% Saponin | 80 |
| Supernatant + 0.4% Saponin | 80 |
| Supernatant + 0.8% Saponin | 80 |

Example 12

CTAB Extraction of HOX in 100 L Fermentor

After 120 h of fermentation (FermID Vest9910b) a CTAB solution (360 g CTAB dissolved in 3.6 L water at 40° C.) was added directly to the broth through an inlet port in the 100 L fermentor. The final concentration of CTAB in the fermentation broth was approximately 4 g/L, since the active fermentor volume was approximately 90 L. Simultaneously, agitation, aeration, pH control and feed addition were stopped. The temperature was controlled to 25° C., and after 22 h of CTAB treatment the broth's HOX content had increased from 1.6 U/mL to 30 U/mL.

Example 13

Homogenization of HOX Producing *Hansenula Polymorpha* in Lab Scale

In order to test the efficiency of HOX extraction as a result of the CTAB treatment, the cells from two different fermentation trials were disrupted by using a cell disruption equipment "Z Plus" 2.2 kW (Constant Systems Ltd, UK). The cells (5 mL) were disrupted using a one shot pump head at various pressures. After opening, the cell debris was separated from the supernatant by centrifugation (5 min at 10,000 g) and the intracellular HOX level in the cell-free supernatant was measured using the HOX assay as previously described. The same cells have also been treated with 0.2% CTAB (25° C., 500 rpm, 20h) and cell-free extract was used as a comparable matter.

Results 13

The data presented in Table 12 indicate that the total amount of intracellular HOX is extracted by treatment with 0.2% CTAB.

TABLE 12

Efficiency of CTAB-treatment.

| Test | Pressure [bar] | HOX activity [U/mL] |
| --- | --- | --- |
| HOX9931-8 | 1500 | 14.1 |
| HOX9931-8 | 2000 | 16.3 |
| HOX9931-8 | 2200 | 16.4 |
| HOX9931-8 | 2500 | 16.2 |
| HOX9931-8 | 2600 | 16.7 |
| HOX9931-8 | 2700 | 15.7 |
| HOX9931-8 + 0.2% CTAB* | — | 18.6 |
| HOX9934-8 | 2700 | 8.9 |
| HOX9934-8 + 0.2% CTAB* | — | 7.3 |

*Cells were incubated for 48 hours at 25° C.

Example 14

Homogenization of HOX Producing *Hansenula polymorpha* in Large Scale

10 L of fermentation broth (FermID Vest9907b) was homogenised in an APV Gaulin high pressure homogenizer model 30 CD. The homogenizer was operated by maximum flow rate (100 L/min) and by a pressure of 1000 bar. During the homogenisation procedure the broth was cooled with ice water, and the product temperature never exceeded 20° C. A rapid increase in HOX activity was observed during the first three cycles, followed by an almost steady level after 5-7 cycles.

Results 14

The results are shown in Table 13 and in FIG. 8.

TABLE 13

Mechanical extraction of HOX from *Hansenula polymorpha*

| Cycle # | HOX activity [U/mL] |
|---|---|
| 0 | 0.86 |
| 1 | 5.6 |
| 2 | 6.4 |
| 3 | 6.6 |
| 4 | 6.6 |
| 5 | 6.7 |
| 6 | 6.9 |
| 7 | 6.7 |

Example 15

The Effect of Triton X-100 on the Extraction of HOX from *Hansenula polymorpha*

CTAB or Triton X-100 was added to 5 mL of ferment, (sample HOX9954, Mut 45, 18.10.99, HVP) in a centrifuge tube. Water was added to the control. The samples were incubated at 25° C. for 22 h at 200 rpm. After incubation the samples were centrifuged and the supernatant was analyzed for HOX activity as previously described.

Results 15

The results are shown in Table 14 and FIG. 9. The non-ionic detergent, Triton X-100 has been used to permeabilize yeast cells (see Naglak et al 1990 and U.S. Pat. No. 5,124,256) but it is clear from this experiment that Triton X-100 has no extracting effect, contrary to CTAB which has not been described in the prior art to be capable of extracting an intracellular enzyme such as a HOX enzyme, although it has been described to give permeabilisation of cells.

TABLE 14

HOX extraction with CTAB compared to Triton X-100.

| Test | HOX activity [U/mL] |
|---|---|
| 0.2% CTAB | 14.5 |
| 0.4% CTAB | 20.5 |
| 0.1% Triton X-100 | 1.5 |
| 0.2% Triton X-100 | 1.6 |
| 0.4% Triton X-100 | 1.8 |
| 0.6% Triton X-100 | 1.9 |
| 1.0% Triton X-100 | 1.9 |
| Control, ferment | 1.2 |

Example 16

Western Blotting

Western blotting was used to test the efficiency of HOX secretion by analysing the amounts of residual (pellet) and released (supernatant) HOX enzyme. Cells were treated with 0, 0.1, 0.2 and 0.4% CTAB, respectively, for 20 hours. After incubation the cells were separated by centrifugation at 4000 g for 10 min. SDS-Page (4-12% Mes Nu-Page) of the resultant supernatant is shown in lane 7-10 of FIG. 10A. The pellets were washed twice with buffer, and then re-suspended in buffer and disrupted on a FastPrep cell disrupter. The pellet extracts were also applied to an SDS-PAGE (see lanes 2-5 in FIG. 10A), using precast Novex gels according to manufacturer's instructions (Novex, San Diego, US). The SDS-Page gel was blotted to a nitrocellulose membrane according to manufacturer's instructions (Novex, San Diego, US). The blot was incubated with antibodies (rabbit antiserum # 4364 BI/OCH 190797) raised against the HOX enzyme, the preparation of which is described below.

Production of HOX Specific Antibodies

A recombinant HOX enzyme was produced in *Escherichia coli* from the expression plasmid PUPO181 as described in WO 96/40935. The crude extract of *E. coli* cells expressing recombinant HOX was analysed by SDS-PAGE. A prominent protein band at the relative molecular weight (Mr) of 62 kD corresponding to HOX was transferred to a polyvinylidene difluoride (PVDF) membrane and subjected to N-terminal amino acid sequence analysis as described in WO 96/40935. The amino acid sequence identified was: Ala-Thr-Leu-Pro-Gln-Lys-Asp-Pro-Gly-Tyr- (SEQ ID NO: 1). This sequence corresponded to amino acids Nos. 2-11 in the published sequence for HOX (Hansen and Stougaard, 1997). Therefore, it was concluded that the expressed 62 kD protein was recombinant HOX lacking the N-terminal amino acid methionine, $Met_1$.

The 62 kD HOX band observed in SDS-PAGE was purified by preparative SDS-PAGE and electroelution from the gel as described by Hunkapiller et al (1983). The purity of the electroeluted 62 kD HOX band was analysed by SDS-PAGE and by amino acid sequence analysis as described above. The purified HOX was used for antibody production in rabbits. Portions of approximately 50 μg were mixed with an equal volume of incomplete Freund's adjuvant and used for immunization.

The HOX specific polyclonal antibodies produced in the rabbits were used throughout this study in Western blot analyses. Proteins to be analysed by Western blot analysis were electrophoresed as described above and transferred to a nitrocellulose filter according to standard procedures. The nitrocellulose membrane was blocked 1 hour in a TBS-T solution (50 mM Tris, pH 7.5; 150 mM NaCl; 0.1% Tween-20) containing 3% skimmed milk powder. HOX specific antibodies diluted 1:10,000 in TBS-T containing 1.5% skimmed milk powder were added and the blot was incubated overnight. The blot was washed three times in TBS-T before incubation (1 to 2 hours) with the secondary antibody (alkaline phosphatase-conjugated goat anti-rabbit immunoglobulins, DAKO, cat. no. D0487), diluted 1:1000 in TBS-T containing 1.5% skimmed milk powder. The blot was subsequently washed in TBS-T (2×20 min) and in TBS (50 mM Tris, pH 7.5; 150 mM NaCl; 1×5 min) before development in Nitroblue tetrazolium/ 5-Bromo-4-chloro-3-indolylphosphate (NBT/BCIP) buffer according to standard procedures.

The specificity of the antibodies was investigated in a series of Western blots with HOX containing extracts from *Chondrus crispus*, *E. coli* and *Pichia pastoris*, respectively. Western blot analysis of HOX containing extracts of *P. pastoris* showed a strong HOX specific band at Mr 62 kD in addition to two or three weaker bands at lower molecular weight.

Results 16

The results of the Western blot are shown in FIG. 10B. This Western blot confirms that practically no HOX is left in the cells after treatment with 0.4% CTAB.

Example 17

Description of High Throughput Screening (HTS) for Increased Levels of Intracellular Enzymes A *Hansenula polymorpha* strain expressing the intracellular HOX enzyme was mutated with UV light at a wavelength of 254 nm. The mutated strain was plated on agar plates (1.4 g/L Yeast Nitrogen Base (YNB) from Gibco, 5 g/L $(NH_4)_2SO_4$, 1 g/L glycerol and 2% (w/v) agar) and incubated at 30° C. until colonies were formed. The colonies were inoculated with a robotic colony picker (Q-Pix, Genetix, Christchurch Dorsett, UK) into 96 well microtiter plates. Each microtiter well contained 200 µL YNB medium (100 mM MES pH 6.1, 1.4 g/L YNB from Gibco, 5 g/L $(NH_4)_2SO_4$ and 10 g/L glycerol). The microtiter plates were incubated at 25° C. with shaking for 7 days in an IOC400.XX2.C shaking incubator (SANYO Gallenkamp BV, Breda, The Netherlands). HOX activities were measured on 10 µL fermentation broth with the HOX assay modified to contain only 105 µL reagent 1 and 15 µL 0.4% (w/v) CTAB was added to the assay. The reaction time was 60 minutes at 30° C. The HOX assay was carried out with a Plato 7 pipetting robot (Rosys, Hombrechtikon, Switzerland) and the absorbencies were measured in a Spectramax plus microtiter plate reader (Molecular Devices, UK). The growth in each individual microtiter well was measured by transferring 10 µL of fermentation broth to a new microtiter plate, adding 100 µL of 100 mM phosphate buffer, pH 6.3 and measuring the absorbency at 600 nm. The HOX measurements were normalized with respect to the absorbency at 600 nm to take poor growth into account.

Results 17

The results demonstrate that it is possible to screen for mutants of *Hansenula polymorpha* producing elevated levels of intracellular HOX enzyme.

Example 18

Comparison of Specific Activity from CTAB Extracted HOX and "Mechanically Extracted" HOX Comparison of specific activity from CTAB extracted HOX (see for example Table 12) and "mechanically extracted" HOX enzymes (see for example Table 13 and FIG. 8).

Results 18

The results demonstrate that the specific activity of CTAB extracted HOX is higher than the specific activity of "mechanically extracted" HOX. These results indicate that the CTAB does not extract all of the intracellular proteins localised in the organelle, but mainly the cytosolic proteins.

Example 19

Characterisation of CTAB- and Mechanically Extracted HOX by Anion Exchange Chromatography In order to analyse the purity of the CTAB extracted HOX, it was compared to HOX extracted by using cell disruption. The specific activity was determined and compared, and the nucleic acid contents of the extracts were compared. Furthermore the purity was examined by anion exchange chromatography.

Seven mL cell suspension (cell+supernatant) was added to a 15 mL centrifuge tube (HOX9957, Mut 45). Upon addition of 0.4% CTAB the cell suspension was incubated for 23 hours at 30° C. (200 rpm). The cells were removed by centrifugation (10000 g and 10 min) and cell-free supernatant was used as a source of CTAB extracted HOX. Another 7 mL of the same cell suspension (without adding CTAB) was disrupted by using a one shot pump head at 2×2400 bar (Z Plus, 2.2 kW, Constant Systems Ltd, UK). The cell debris was then separated by centrifugation (10000 g and 10 min) and the supernatant was used as a source of mechanically extracted HOX.

Both samples were desalted on a PD 10 column (Pharmacia Biotech.) in 20 mM TEA (triethanolamin, Merck) buffer, pH 7.3. The samples were analysed for HOX activity and protein-concentration (protein assay is based on the assay method described by Schleif and Wensink, 1981. The nucleic acid content was determined by measurement of the absorption at 260 and 280 nm (Bollag and Edelstein, 1991.

Ion Exchange Chromatography was carried out by using a Biologic Duo Flow (Bio-Rad, CA, USA) system. 500 µl of desalted sample was applied to a Source Q 15 column (HR5/5, Pharmacia Biotech.) equilibrated in TEA buffer (buffer A, 20 mM, pH 7.3). The HOX was eluted with a 20 mL linear gradient from 0-0.5 M NaCl in buffer A with a flow rate of 1.5 mL/min during which 1.5 mL fractions were collected and assayed for HOX activity.

Results 19

Determination of specific activity shows that CTAB extracted HOX is much more pure compared to mechanically extracted HOX (Table 15). Also the nucleic acid content is much lower in the CTAB extracted HOX than in the mechanically extracted HOX (Table 15).

TABLE 15

HOX- and protein concentration in CTAB- and mechanically extracted HOX.

| Test | HOX activity [U/mL] | Protein concentration [mg/mL] | Specific activity [U/mg protein] | Nucleic acid concentration [µg/mL] |
| --- | --- | --- | --- | --- |
| CTAB extracted | 30.6 | 2.33 | 13.1 | 102 |
| Mechanically extracted | 32.0 | 12.7 | 2.5 | 384 |

The anion exchange chromatography analyses in FIGS. 11A and 11B which show chromatograms of the Source Q analyses for the CTAB- and mechanically extracted HOX also strongly confirm this result.

Examples 20, 21 and 22 describe experiments with CTAB. In Examples 20 and 21, two different media were chosen for experiments with CTAB: YP/1% glyceroln (Example 20) and YNB/1% glycerol+0.1 M NaPi pH 6.0 (Example 21).

Example 20

HOX/CTAB/Cultivation in YP/1% Glycerol 50 mL medium was inoculated with 2.5 mL of a YPD preculture and cultivated at 37° C., 160 rpm.

After 28 h cultivation, 1% (v/v) methanol was added and further incubated for 18 h at 37° C., 160 rpm.

The $OD_{600\ nm}$ was measured to calculate the amount of CTAB which is necassary.

Aliquots of the supernatant (SN) and the cell pellet of 1.5 mL culture were taken.

After mechanical disruption of the cells the soluble fraction (CX) was isolated.

SN of these conditions was designated A
CX of these conditions was designated D
Same volumes of the culture (20 mL) were aliquoted into two shake flasks.

20 mL of the culture was supplemented with 0.005 g CTAB.

(CTAB—stock solution: 0.02 g/mL; DANISCO: 0.4% in fermentor culture ($OD_{600\ nm}$~300)
shake flask experiments $OD_{600\ nm}$~20=>0.027 g CTAB/ 100 mL culture)
incubation of the culture: 24 h, 4° C. without shaking
SN of these conditions was designated C
CX of these conditions was designated F
The second shake flask without CTAB was incubated under the same conditions as the CTAB—flask and served as reference culture.
SN of these conditions was designated B
CX of these conditions was designated E Strains, harbouring five different IL-1ra constructions were cultivated. The strains 4-17, AL 9/2 and II 3-1 contained three different constructions without a signal sequence, while the strains MFα 2 and MFα AL7/1 represented two different constructions with the MFα pre-pro sequence.

Strain FPMT 8 was cultivated under the same conditions as the recombinant strains. This strain is an RB11 integrant with nearly 30 copies of the empty Hansenula vector pFPMT121 and served as negative control.

After treatment with CTAB, a 40 fold (20 fold) to 110 fold increase of the IL-1ra concentration was detected in the supernatant of strains, harbouring constructions without signal sequences.

For the MFα-strains treated with CTAB, a lower increase (2 to 5 fold) of the IL-1ra concentration was measured.

Results 20

The results are summarized in Table 16.

TABLE 16 experiments with CTAB in YP/glycerol/methanol

| strain | sequence | $OD_{600\ nm}$ | SN sample | ELISA IL-1ra [µg/mL] | factor |
|---|---|---|---|---|---|
| 4-17 | 2 | 20.5 | A | 0.345 | C/A = 113 |
| | | | B | 0.346 | C/B = 113 |
| | | | C | 39.0 | |
| AL 9/2 | 3 | 22.6 | A | 0.166* | C/A = 20 |
| | | | B | 0.179 | C/B = 19 |
| | | | C | 3.39 | |
| II 3/1 | 4 | 18.7 | A | 1.67 | C/A = 49 |
| | | | B | 1.94 | C/B = 42 |
| | | | C | 81.2 | |
| MF α2 | 6 | 20.4 | A | 4.85 | C/A = 6 |
| | | | B | 5.69 | C/B = 5 |
| | | | C | 27.7 | |

TABLE 16-continued experiments with CTAB in YP/glycerol/methanol

| strain | sequence | $OD_{600\ nm}$ | SN sample | ELISA IL-1ra [µg/mL] | factor |
|---|---|---|---|---|---|
| MF αAL 7/1 | 8 | 22.6 | A | 2.28 | C/A = 2.3 |
| | | | B | 2.02 | C/B = 2.6 |
| | | | C | 5.23 | |

A: supernatant after cultivation for 46 h in YP/glycerol/methanol
B: supernatant after cultivation for 46 h in YP/glycerol/methanol, than incubated for 24 h without CTAB
C: sterile filtrated supernatant after cultivation for 46 h in YP/glycerol/methanol, than incubated for 24 h with CTAB
*remarks:
The IL-1ra concentration in supernatant of strain AL 9/2 was unusually low. In further experiments concentrations between 0.6 and 0.7 µg/mL were detected.
The reason for the low yield is not known.

Example 21

HOX/CTAB/Cultivation in YNB/1% glycerol+0.1 M Na Pi pH 6.0

For further experiments with CTAB, three strains harbouring three different constructs without signal sequences were selected (strain 4-17; AL 9/2; II 3-1).

45 mL medium was inoculated with 5 mL of a YPD preculture and cultivated at 37° C., 160 rpm.

After 28 h cultivation 1% (v/v) methanol was added and further incubated for 18 h at 37° C., 160 rpm.

The $OD_{600\ nm}$ was measured to calculate the amount of CTAB which is necessary.

Aliquots of the supernatant (SN) and the cell pellet of 3 mL culture were taken.

After mechanical disruption of the cells the soluble fraction (CX) was isolated.

SN of these conditions was designated A
CX of these conditions was designated D
Same volumes of the culture (20 mL) were aliquoted into two shake flasks.

20 mL of the culture was supplemented with 0.003 g CTAB.

incubation of the culture: 24 h, 4° C. without shaking
SN of these conditions was designated C
CX of these conditions was designated F
The second shake flask without CTAB was incubated under the same conditions as the CTAB—flask and served as reference culture.
SN of these conditions was designated B
CX of these conditions was designated E In all cases, incubation with CTAB led to an significant increase of the IL-1ra concentration in the supernatant (100 to 130 fold).

Results 21

The ELISA results of the CTAB experiments after cultivation in two different media are compared in the following Table 17.

TABLE 17 comparison of CTAB experiments in YP/glyc/methanol and YNB/glyc/methanol

| strain | SN sample | YP/glyc/methanol | | | YNB/glyc/methanol (pH 6.0) | | |
|---|---|---|---|---|---|---|---|
| | | $OD_{600\,nm}$ | ELISA IL-1ra [µg/mL] | factor | $OD_{600\,nm}$ | ELISA IL-1ra [µg/mL] | factor |
| 4-17 | A | 20.5 | 0.345 | C/A = 113 | 10.2 | 0.205 | C/A = 108 |
| | B | | 0.346 | C/B = 113 | 10.8 | 0.069 ? | (C/B = 322) |
| | C | | 39.0 | | 9.8 | 22.2 | |
| AL 9/2 | A | 22.6 | 0.166 | C/A = 20 | 10.1 | 0.045 | C/A = 137 |
| | B | | 0.179 | C/B = 19 | 11.6 | 0.025 ? | (C/B = 246) |
| | C | | 3.39 | | 11.0 | 6.16 | |
| II 3/1 | A | 18.7 | 1.67 | C/A = 49 | 10.0 | 0.276 | C/A = 105 |
| | B | | 1.94 | C/B = 42 | 11.4 | 0.279 | C/B = 104 |
| | C | | 81.2 | | 10.6 | 29.1 | |

A: supernatant after cultivation for 46 h in YP/glycerol/methanol (or YNB/glycerol/methanol)
B: supernatant after cultivation for 46 h in YP/glycerol/methanol (or YNB/glycerol/methanol), than incubated for 24 h without CTAB
C: steril filtrated supernatant after cultivation for 46 h in YP/glycerol/methanol (or YNB/glycerol/methanol), than incubated for 24 h with CTAB Example 22

Test of Different Incubation Conditions

For strain II 3/1, cultivated in YP/glycerol/methanol (see 1.a) different incubation conditions after addition of CTAB were tested.
conditions:
24 h CTAB, 4° C. without shaking ("standard" condition)
24 h CTAB; 4° C. gently shaking
24 h CTAB, 37° C. without shaking
24 h CTAB; 37° C. gently shaking
Results 22
The concentration of IL-1ra in the supernatant was measured by ELISA. The results are summarized in Table 18.

TABLE 18 different incubation condition of CTAB (ELISA results)

| strain II 3/1 | | ELISA IL-1ra [µg/mL] | factor |
|---|---|---|---|
| supernatant | A | 1.67 | |
| 4° C. without shaking | } B | 1.94 | C/B = 42 |
| | C | 81.2 | C/A = 49 |
| 4° C. gently shaking | } B | 1.62 | C/B = 28 |
| | C | 44.7 | C/A = 27 |
| 37° C. without shaking | } B | 8.04 | C/B = 16 |
| | C | 127.4 | C/A = 76 |
| 37° C. gently shaking | } B | 11.1 | C/B = 4 |
| | C | 46.2 | C/A = 28 |

A: supernatant after cultivation for 46 h in YP/glycerol/methanol
B: supernatant after cultivation for 46 h in YP/glycerol/methanol, than incubated for 24 h without CTAB
C: steril filtrated supernatant after cultivation for 46 h in YP/glycerol/methanol, than incubated for 24 h with CTAB The highest increase of IL-1ra in the supernatant was measured after CTAB incubation at 37° C. without shaking (76fold) and after CTAB incubation at 4° C. without shaking (49fold).

The highest IL-1ra concentration was detected at 37° C., but the concentration in the reference sample incubated without CTAB was also increased (16 fold).

The high concentration in the reference sample could be caused by cell lysis.

best conditions: 4° C. (to avoid cell lysis) without shaking

Example 23

SDS-PAGE, Western Blot and Coomassie Staining

The supernatant and the soluble fraction of the crude extract isolated from the shake flask experiments were analyzed by SDS-PAGE under reducing conditions.
gel: 16% Novex-gel TG 1 mm; reducing conditions
colloidal coomassie staining (BIO-SAFE Coomassie, Bio-rad)
Referenz-Stämme: samples:
A: supernatant after cultivation for 46 h in YP/glycerol/methanol
B: reference supernatant without CTAB
C: supernatant after treatment with CTAB
D: soluble fraction (CX) of crude extract 1:3 diluted
E: soluble fraction (CX) of crude extract reference culture 1:3 diluted
F: soluble fraction (CX) of crude extract after CTAB treatment 1:3 diluted
Results 23
WB 33 and Coo2
strains: 4-17 pFPMT icIL 1raI
Al 9/2 pFPMT icIL 1ral+Al
CTAB: incubation for 24 h; 4° C. without shaking
The western blot (WB 33) results are presented in FIG. 12A.
The test samples and quantities added are presented in the following legend to FIG. 12A.

| 1. MW marker See Blue | | | | 10 µL (total) |
|---|---|---|---|---|
| 2. 4-17 | A | SN | | 11.3 µL |
| 3. 4-17 | D | CX | 1:3 dil. | 11.3 µL |
| 4. 4-17 | C | SN | CTAB | 11.3 µL |
| 5. 4-17 | F | CX | CTAB 1:3 dil. | 11.3 µL |
| 6. rhIl-1ra-standard (BSA-free) | | | | 30 ng |
| 7. AL 9/2 | A | SN | | 11.3 µL |
| 8. AL 9/2 | D | CX | 1:3 dil. | 11.3 µL |
| 9. AL 9/2 | C | SN | CTAB | 11.3 µL |
| 10. AL 9/2 | F | CX | CTAB 1:3 dil. | 11.3 µL |

The results demonstrate that for both strains an increase of IL-1ra in the SN (lane 4, lane 9) and a decrease in the CX (lane 5, lane 10) was detected after treatment with CTAB.

The colloidal coomassie (Coo 2) blue staining is shown in FIG. 12B

The test samples and quantities addded are presented in the following legend to FIG. 12B.

| 1. MW marker Mark 12 | | | | 10 μL (total) |
|---|---|---|---|---|
| 2. 4-17 | A | SN | | 11.3 μL |
| 3. 4-17 | D | CX | 1:3 dil. | 11.3 μL |
| 4. 4-17 | C | SN | CTAB | 11.3 μL |
| 5. 4-17 | F | CX | CTAB 1:3 dil. | 11.3 μL |
| 6. 4-17 | B | SN | w/o CTAB | 11.3 μL |
| 7. 4-17 | E | CX | w/o CTAB 1:3 dil. | 11.3 μL |
| 8. rhIl-1ra-Standard (BSA-free) | | | | 100 ng |
| 9. AL 9/2 | A | SN | | 11.3 μL |
| 10. AL 9/2 | D | CX | 1:3 dil. | 11.3 μL |
| 11. AL 9/2 | C | SN | CTAB | 11.3 μL |
| 12. AL 9/2 | F | CX | CTAB 1:3 dil. | 11.3 μL |
| 13. AL 9/2 | B | SN | w/o CTAB | 11.3 μL |
| 14. AL 9/2 | E | CX | w/o CTAB 1:3 dil. | 11.3 μL |
| 15. FPMT 8 | A | SN | | 11.3 μL |

WB 34 and Coo 3
strains: MF α2 pFPMT MFα IL-1raI
MFαAL 7/1 pFPMT MFα IL-1raI+Al
CTAB: incubation for 24 h; 4° C. without shaking
The western blot (WB 34) results are presented in FIG. 13A The test samples and quantities addded are presented in the following legend to FIG. 13A.

| 1. MW marker See Blue | | | | 10 μL (total) |
|---|---|---|---|---|
| 2. MFα 2 | A | SN | | 11.3 μL |
| 3. MFα 2 | D | CX | 1:3 dil. | 11.3 μL |
| 4. MFα 2 | C | SN | CTAB | 11.3 μL |
| 5. MFα 2 | F | CX | CTAB 1:3 dil. | 11.3 μL |
| 6. rhIl-1ra-standard (BSA-free) | | | | 30 ng |
| 7. MFα AL7/1 | A | SN | | 11.3 μL |
| 8. MFα AL7/1 | D | CX | 1:3 dil. | 11.3 μL |
| 9. MFα AL7/1 | C | SN | CTAB | 11.3 μL |
| 10. MFα AL7/1 | F | CX | CTAB 1:3 dil. | 11.3 μL |

The results indicate that after treatment with CTAB a mixture of intracellular and secreted IL-1ra was detected in the supernatants C in lane 4 and 9.

MFα 2: additional band of 20 kDa and 34 kDa derived from intracellular IL-1ra

MFα 7/1: additional band of <17 kDa derived from intracellular IL-1ra intensity of 18 kDa signal increased The colloidal coomassie (Coo 3) results are presented in FIG. 13B The test samples and quantities addded are presented in the following legend to FIG. 13B.

| 1. MW marker Mark 12 | | | | 10 μL (total) |
|---|---|---|---|---|
| 2. MFα 2 | A | SN | | 11.3 μL |
| 3. MFα 2 | D | CX | 1:3 dil. | 11.3 μL |
| 4. MFα 2 | C | SN | CTAB | 11.3 μL |
| 5. MFα 2 | F | CX | CTAB 1:3 dil. | 11.3 μL |
| 6. MFα 2 | B | SN | w/o CTAB | 11.3 μL |
| 7. MFα 2 | E | CX | w/o CTAB 1:3 dil. | 11.3 μL |
| 8. rhIl-1ra-Standard (BSA-free) | | | | 100 ng |
| 9. MFα AL7/1 | A | SN | | 11.3 μL |
| 10. MFα AL7/1 | D | CX | 1:3 dil. | 11.3 μL |
| 11. MFα AL7/1 | C | SN | CTAB | 11.3 μL |
| 12. MFα AL7/1 | F | CX | CTAB 1:3 dil. | 11.3 μL |
| 13. MFα AL7/1 | B | SN | w/o CTAB | 11.3 μL |
| 14. MFα AL7/1 | E | CX | w/o CTAB 1:3 dil. | 11.3 μL |
| 15. FPMT 8 | C | SN | CTAB | 11.3 μL |

WB 35 and Coo 4
strain: II 3/1 pFPMT icIL-1ra type II
different incubation conditions after addition of CTAB:
24 h CTAB, 4° C. without shaking ("standard" condition)
24 h CTAB, 37° C. without shaking
The western blot (WB 35) results are presented in FIG. 14A The test samples and quantities addded are presented in the following legend to FIG. 14A.

| 1. MW marker See Blue | | | | | 10 μL (total) |
|---|---|---|---|---|---|
| 2. II 3/1 | SN | | | | 11.3 μL |
| 3. II 3/1 | CX | | | 1:3 dil. | 11.3 μL |
| 4. II 3/1 | SN | CTAB | 4° C. | | 11.3 μL |
| 5. II 3/1 | CX | CTAB | 4° C. | 1:3 dil. | 11.3 μL |
| 6. rhIl-1ra-Standard (BSA-free) | | | | | 30 ng |
| 7. II 3/1 | SN | CTAB | 37° C. | | 11.3 μL |
| 8. II 3/1 | CX | CTAB | 37° C. | 1:3 dil. | 11.3 μL |
| 9. II 3/1 | SN | w/o CTAB | 37° C. | | 11.3 μL |
| 10. II 3/1 | CX | w/o CTAB | 37° C. | 1:3 dil. | 11.3 μL |

The colloidal coomassie (Coo 4) results are presented in FIG. 14B

The test samples and quantities added are presented in the following legend to FIG. 14B.

| 1. MW marker Mark 12 | | | | | 10 μL (total) |
|---|---|---|---|---|---|
| 2. II 3/1 | SN | | | | 11.3 μL |
| 3. II 3/1 | CX | | | 1:3 dil. | 11.3 μL |
| 4. II 3/1 | SN | CTAB | 4° C. | | 11.3 μL |
| 5. II 3/1 | CX | CTAB | 4° C. | 1:3 dil. | 11.3 μL |
| 6. II 3/1 | SN | w/o CTAB | 4° C. | | 11.3 μL |
| 7. II 3/1 | CX | w/o CTAB | 4° C. | 1:3 dil. | 11.3 μL |
| 8. II 3/1 | SN | CTAB | 37° C. | | 11.3 μL |
| 9. II 3/1 | CX | CTAB | 37° C. | 1:3 dil. | 11.3 μL |
| 10. II 3/1 | SN | w/o CTAB | 37° C. | | 11.3 μL |
| 11. II 3/1 | CX | w/o CTAB | 37° C. | 1:3 dil | 11.3 μL |
| 12. rhIl-1ra-Standard (BSA-free) | | | | | 100 ng |
| 13. FPMT 8 | CX | CTAB | 4° C. | 1:3 dil. | 11.3 μL |
| 14. FPMT 8 | SN | CTAB | 4° C. | | 11.3 μL |
| 15. FPMT 8 | SN | | | | 11.3 μL |

The results demonstrate that after CTAB incubation at 4° C. as well as at 37° C. an increase of IL-1ra in the SN (WB 35: lane 4, lane 8) and a decrease in the CX (WB 35: lane 5, lane 9) was detected.

In SN CTAB 37° C. (lane 8) the highest amount of IL-1raII was obtained. This result is in agreement with the ELISA results (see Table 3).

In this supernatant not only more IL-1raII but more other proteins (>35 kDa) were stained (Coo 4: lane 8). This observation confirmed the assumption that a significant cell lysis took place at 37° C. as compared to 4° C.

Discussion

The codon usage of the *Chondrus crispus* HOX gene (Stougaard and Hansen 1996, Hansen and Stougaard, 1997) was modified by replacement of the low-usage codons with those of the more frequently used codons of the *Hansenula* host organism. A transformant of the methylotrophic yeast, *Hansenula polymorpha*, expression system (developed at Rhein Biotech, Düsseldorf/Germany), containing a codon optimized HOX DNA fragment for the expression of HOX was prepared.

The codon optimisation of the gene encoding the HOX enzyme resulted in high levels of expression (in terms of high levels of enzyme activity) of the HOX enzyme in the *Hansenula polymorpha* yeast host organisms. When a signal sequence was not present the HOX enzyme was localized intracellularly. However, even when a number of different signal sequences were used in different constructs, little or no HOX activity could be measured in the extracellular medium. These results indicated that the HOX enzyme is incapable of being secreted even from host strains expressing a HOX enzyme comprising a signal sequence. Western blots also confirmed that the HOX enzyme may be localized in a membrane associated fraction even when a signal sequence was present, indicating that although there is transcription and translation of the HOX gene, the HOX enzyme was not secreted and seemed to get lodged in the secretion pathway.

The extraction of the intracellular enzymatically active HOX enzyme using the method of the present invention was compared with a traditional cell disruption method and with extraction procedures using other ionic/non ionic detergents and emulsifiers. Combinations of detergents with protease and salts were also investigated.

Example 24

Expression of Glucan Lyase in *Hansenula*

The glucan lyase from the seaweed *Gracilariopsis lemaneiformis* is an enzyme (EC 4.2.2.13) which catalyses the degradation of α-1,4-glucans in starch and glycogen to 1,5-anhydro-D-fructose (see FIG. 15).

Details of the identification of glucan lyase, including its purification from red alga, are set out in Yu et al., 1999, *Biochimica et Biophysica Acta* 1430, 396-402.

The enzyme consists of 1038 amino acids and has a molecular weight of 117 kDa. The optimal pH range is between pH 4-7 and the temperature optimum for the glucan lyase is in the range 37-50° C. The enzyme is very stable showing no loss of activity when kept for several months at 22° C. at pH 5.5-5.8.

FIG. 16A shows the structure of the full length glucan lyase gene (3153 bp). The central part is well conserved among glucan lyases and a-glucosidases. The N-terminal part is thought to have a starch-binding domain (Yu et al (1999), Biochimica et Biophysica Acta 1433 p.1-15).

Example 25

Expression and Purification of Glucan Lyase from *Hansenula polymorpha* Using LTAB In this and the following Examples, glucan lyase in is expressed in an industrial organism for mass production of the enzyme and therefore the sugar. The expression and catalytic role of the N- and C-terminal and the central of the lyase is also examined.

Expression constructs for expression of glucan lyase are described in Larsen, KS.

Expression of algal α-1,4-glucan lyase in *Hansenula polymorpha*. B.Sc. report, incorporated by reference. In particular, tranformant 42 (also referred to as HP#42 and DCDK0129) is an expression construct comprising the full length glucan lyase gene, which encodes a glucan lyase with 1035 amino acids and molecular weight of 117 kDa.

In Examples 25 to 32, four constructs are made by standard PCR and recombinant DNA techniques: (1) the full length gene (1038 aa); (2) the 5' end+the central part (938 aa, 5' agl); (3) the central part (715 aa, aglcore); and (4) the 3' end+the central part (815 aa, 3' agl).

The constructs are transformed into *H. polymorpha* by electroporation. The aim of the study is to obtain an efficient expression of algal glucan lyase in order to get a large scale production of the enzyme.

Construction of Glucan Lyase Expression Vector

The *Hansenula* expression vector pFPMT121 (FIG. 16B) is used to construct the glucan lyase expression vector.

The glucan lyase gene is assembled using PCR using the following primers

```
                                          (SEQ ID NO:29)
US-agl1: GAA TTC ATG ACC GCA TTG TCC GAC AAA CAA
         ACG GCT (SEQ ID NO:30)
LS-agl2: ACC CGG GGT AGA AGA GCC GGC AGC AAA CCA
         GTT (SEQ ID NO:31)
US-agl5: GGG TGA GCT CTG CCA CTT CCA GGG CTG CGC
         TGT TC (SEQ ID NO:32)
LS-agl6: GGA GAT CTT TAT TAA TGG TGA TGG TGA TGG
         TGG GTA ATT GTG ATC ACA GCG TCC GG
```

The PCR protocol used is as follows: The 3' end of the glucan lyase gene is amplified using primers US-agl5 and LS-agl6, and the 5' end is amplified using US-agl1 and LS-agl2, and the respective PCR products are ligated into pCR-Blunt II-TOPO and transformed into TOP10 *E. coli* cells using standard protocols (Strategene/Invitrogen).

The 3' end product is excised from pCR Blunt using EcoRI and BglII and ligated into pFPMT121 and transformed into TOP10 *E. coli* cells, the resultant plasmid is cut with EcoRI to produce vector fragment 1. The 5' end product is excised using EcoRI and XmaI to make insert fragment 1. Insert fragment 1 and vector fragment 1 are ligated using standard protocols to prepare the pFPMT121-glucan lyase expression vector. The PCR products are sequenced to ensure no errors had been introduced during the cloning strategy.

Preparation of *Hansenula polymorpha* Competent Cells

The strain RB11 (ura⁻) is grown in 5 ml of YPD containing 2% peptone, 1% yeast extract and 2% glucose at 37° C. with shaking over night. The culture is diluted 50-fold in 200 ml of prewarmed YPD and the culture is grown at 37° C. to an $OD_{660\,nm}$=1.0-1.3. The culture is transferred to a centrifuge tube and the cells are harvested by centrifugation at 3000 rpm for 5 minutes at room temperature.

The cells are resuspended in 20 ml of PPD buffer (prewarmed to 37° C.) and incubated for 15 minutes at 37° C. Cells are harvested by centrifugation at 3000 rpm for 5 minutes at room temperature. The cells are washed three times with 50 ml of STM buffer. After last wash and centrifugation the cells are put on ice and resuspended in 1 ml of ice-cold STM buffer. Batches of 60 μl cell suspensions are transferred to storage tubes and directly frozen in liquid $N_2$ and kept at −80° C.

Transformation of Gene Constructs in *Hansenula polymorpha* by Electroporation

The constructs are transformed into *H. polymorpha* by electroporation in which the cells get an electric pulse that perforates their cell walls and facilitates the uptake of foreign DNA. 1 μg DNA of each gene construct is used for the transformations. DNA of pFPMT121 without insert and sterile distilled water are transformed as positive and negative control, respectively.

The DNA is added to 60 μl of RB11 competent cells and the mixture is transferred to a prechilled 2-mm electroporation cuvet that is kept on ice until electroporation. The genepulser is adjusted to 1.5 kV, 25 μF, 200Ω so it is ready to fire. Immediately after the pulse 1 ml of YPD medium is added to the cuvet. The cell suspension is incubated at 37° C. for one hour and transferred to eppendorf tubes. The cells are harvested by centrifugation at 3600 rpm for 5 minutes. The cells are washed twice with YND medium (0.14% yeast nitrogen base without amino acids and ammonium sulfate, 2% ammonium sulfate, 2% glucose (2% agarose is added for plates)) and resuspended in 0.5 ml of YND. The samples are plated on YND plates and incubated at 37° C. Transformants appeared on the plates after 3-5 days.

Integration of the construct into the genome of *H. polymorpha* requires time and proper conditions. From the YND-plates transformants are inoculated in 3 ml YND and grown at 37° C. with shaking for two days. As a control 5 transformants of vector DNA are also picked. Every second day 50 μl of cells are transferred to 3 ml fresh YND (repeated 7 times). After the seventh passage 50 μl of cells are transferred to 3 ml YPD and grown over night (repeated once). 20 μl of cells are transferred to 3 ml YND and streaked on YND-plates. The plates are incubated at 37° C. until transformants appeared. This passaging of transformants allows stabilization of the construct that initially exists as a free replicating plasmid and results in forced integration into the chromosomal DNA (1,2). One colony from each YND-plate is inoculated in 3 ml YPD and grown overnight at 37° C. with shaking. To induce the expression of the integrated constructs 100 μl of cells are transferred to 3 ml YND containing 1% glycerol and grown for two days at 37° C.

Transformants are screened using PCR using primers US3-alcore and LS4.

1.0 ml of cell culture is pelleted by centrifugation in a microcentrifuge tube. The supernatant is decanted. One third of the tube is filled with acid washed glass beads (425-600 microns) and 400 μl of 0.1 M MOPS-NaOH (pH=6.2) is added. The cells are opened by shaking in a Mini Bead-Beater (Biospec Products, Bartlesville, Okla.) 4 times 20 seconds at maximum speed. With a hot glowing needle a hole is made in the bottom of each microcentrifuge tube and the tubes are placed in eppendorf tubes. The tubes are centrifuged at low speed so the cell-free extracts are transferred to the eppendorf tubes and the glass beads are retained in the microcentrifuge tubes.

In a PCR tube 10 μl of cell-free extract is mixed with 50 pmole of primers, 1 μl of each dNTP, 10 μl of AmpliTaq DNA Polymerase Buffer, 1 U of AmpliTaq DNA Polymerase and water to a final volume of 50 μl. After preheating for 30 seconds at 950° C. the PCR-program consisted in 30 cycles of 95° C. for 30 seconds, 55° C. for 1 minute and 68° C for 2 minutes and 5 minutes at 72° C. extension at the end. The PCR products are loaded on 2% agarose gels to check the size of the products. The two primers US3-aglcore and LS4-aglcore are used for the PCR-screening

```
                                        (SEQ ID NO:33)
US3-aglcore:  GGA GAT ACT ACC TGG AAC TCT GGA CAA
              GAG GAC (SEQ ID NO:34)
LS4-aglcore:  GTT TGG ATC CCC GCC AGT ACC CAC
```

Intracelluar protein expression is determined using western blot analysis using polyclonal antibodies raised against the glucan lyase protein and raised in rabbit, and conjugated swine anti-rabbit immunoglobulin (DAKA A/S) using standard techniques.

Expression and Purification

Two transformants from transformation of the full-length glucan lyase gene are grown in 250 ml of YND+1% glycerol in 2 L shakeflasks with baffles at 24° C. with shaking. The cultures are inoculated with cells grown in YND+2% glucose so an $OD_{600\ nm}=1$ is obtained in the new media. YND=0.14% yeast nitrogen base without amino acids and ammonium sulphate, 2% ammonium sulphate, 2% glucose.

On the second day of growth the cultures are induced with 1% methanol. After three days of growth the cells are harvested by centrifuging for 10 minutes at 4000 rpm.

The cells are resuspended in 5 mM sodium acetate pH=5.5 with 0.2% LTAB at 30% wet biomass in order to lyse the cells and release the intracellular glucan lyase.

The tubes are incubated over night with shaking at 37° C. The cells are harvested by centrifuging at 4000 rpm in 10 minutes and the glucan lyase activity is determined in the cell-free extract and in the pellet. This is done to check if LTAB had opened the cells successfully before starting the purification of glucan lyase.

Further Purification of Recombinant Algal α-1,4-Glucan Lyase

The recombinant algal α-1,4-glucan lyase expressed in *H. polymorpha* may be further purified by affinity chromatography on a starch column connected to a Fast Protein Liquid Chromatography system (FPLC).

An ÄKTA explorer 10S from Pharmacia Biotech is used and it measured the absorbance at 260 nm and 280 μm. 1.5 g of starch/mg glucan lyase resuspended in 5 mM potassium acetate pH=4 is used to pack a column with a diameter of 1.6 cm and a volume of 23 ml. The column is equilibrated with 5 mM potassium acetate pH=4. The cell-free extract is adjusted to pH=4 and loaded on another column. Both columns are connected to the ÄKTA.

Before starting the purification the system is washed with sterile distilled water and the pumps are washed with 5 mM potassium acetate pH=4 and 20 mM Bis-Tris-HCl pH=6.6+2% dextrin10 (elusion buffer). The starch column is equilibrated with 5 column volumes of 5 mM potassium acetate pH=4. Then the cell-free extract is loaded automatically on the starch column and the column is washed with 5 column volumes of 5 mM potassium acetate pH=4. Glucan lyase is eluted with 20 mM Bis-Tris-HCl pH=6.6 with 2% dextrin10 in fractions of 1 ml. The fractions with a high absorbance at 260 and 280 nanometers are tested for glucan lyase activity and the fractions with highest activity are collected into three large fractions. The three fractions are separately concentrated with a Centriprep YM-30 from Millipore by centrifuging at 1500 rpm at 4° C. so molecules smaller than 30 kDa are removed.

The three fractions are mixed and filtrated, and the glucan lyase is purified by ion-exchange chromatography on a MonoQ column (an anion exchange column from Pharmacia Biotech) connected to the same FLPC system as used above. The column is equilibrated with 10 mM Bis-Tris-HCl pH=7 and the glucan lyase fractions are injected into the system with a needle. The column is washed with 10 mM Bis-Tris-HCl pH=7 and the glucan lyase is eluted with 10 mM Bis-Tris-HCl pH=7+1 M NaCl. The fractions with a high absorbance at 260 nm and 280 nm are tested for glucan lyase activity. Two fractions with high glucan lyase activity are concentrated separately with a Centriprep YM-10 from Millipore by centrifuging at 3000 rpm at 4° C. where the molecule cutoff is 10 kDa.

Example 26

Characterisation of Expressed α-1,4 Glucan Lyase: Western Blot Analysis

A Western blot analysis was done to examine if transformants of the truncated forms express glucan lyase. The Western blot is shown in FIGS. 17A, 17B and 17C.

From the Western blot we can conclude that transformants of the aglcore and the 3' agl construct do not express any algal α-1,4-glucan lyase even though the constructs have been integrated into the genome of *H. polymorpha* as seen during the PCR screening (FIG. 17A. Blot A lanes 1-8 and blot C lanes 9-17). All the transformants from transformation of the full-length glucan lyase gene express large amounts of algal α-1,4-glucan lyase with a molecular weight of over 100 kDa (FIG. 17A. Blot A lane 9 and FIG. 17B Blot B lanes 1-9). Transformation of the 5' agl construct has resulted in a single transformant that also express algal α-1,4-glucan lyase (transformant number 14 in lanes 3 and 4, blot C, FIG. 17C). Several smaller bands are also seen in these two lanes.

In summary, glucan lyase expression is observed in transformants with the full-length gene and in a single transformant harbouring the 5' agl construct as shown in FIGS. 17A, 17B and 17C. No expression is observed for the other two constructs.

Example 27

Characterisation of Expressed α-1,4 Glucan Lyase: Activity Screening

Cell-free extracts from all transformants are used in the activity screening by the DNS method (Yu et al (1998), Carbohydrate Research 305 p.73-82). The absorbance measured at 550 nanometers in the assay is a measurement of the amount of 1,5-anhydrofructose produced and can be used to determine the specific activity of the glucan lyase.

Activity screening of the transformants only detected glucan lyase activity when the full-length gene was transformed. Determination of the specific activity indicated that glucan lyase was expressed at a very high level in 8 transformants as shown in Table 19 below.

TABLE 19

Eight transformants from transformation of the full-length glucan lyase gene showed a high lyase activity when assayed by the DNS method. The protein concentration was determined by the BioRad protein assay. The specific activity and the protein concentration is the average of four independent measurements.

| Transformant | Specific activity (μmol 1,5-anhydrofrucose/ min · ml) | Protein concentration (mg/ml) |
| --- | --- | --- |
| 1 | 4.0 | 0.65 |
| 2 | 9.3 | 0.86 |
| 3 | 7.2 | 0.74 |
| 4 | 4.2 | 0.64 |
| 5 | 2.5 | 0.63 |
| 6 | 5.4 | 0.70 |
| 7 | 6.7 | 0.79 |
| 8 | 8.9 | 0.92 |

As expected no activity was seen when assaying the cell-free extracts from the control transformation of vector DNA.

Example 28

Comparison of α-1,4 Glucan Lyase Expressed in *H. polymorpha* and vs α-1,4 Glucan Lyase Expressed in *Pichia pastoris*

The specific activity of algal α-1,4-glucan lyase expressed from *H. polymorpha* and purified using LTAB, (from data shown in Table 19) expressed in μmol 1,5-anhydrofrucose/ min·mg protein is as follow:

| Transformant | Specific activity (μmol 1,5-anhydrofrucose/ min · mg) |
| --- | --- |
| 1 | 6.11 |
| 2 | 10.78 |
| 3 | 9.70 |
| 4 | 6.61 |
| 5 | 3.98 |
| 6 | 7.76 |
| 7 | 8.42 |
| 8 | 9.62 |

Transformation of the algal α-1,4-glucan lyase gene in the methylotrophic yeast *Pichia pastoris* has previously resulted in a specific activity of 0.7 μmol 1,5-anhydrofrucose/min mg protein (Bojsen K, et al 1999). The expression construct contained a signal sequence, and purification was by secretion into the medium.

This indicates that the expression of glucan lyase in *H. polymorpha* is very efficient, compared to previous methods. Expression in the fingi *Aspergillus niger* has also been done but a low yield is obtained (Yu, et al, 1999, supra).

Specifically, other expression systems tried (*P. pastoris* and *A. niger*) only result in a specific activity of 0.70 μmol AF/min·mg protein, indicating that the expression in *H. polymorpha* is highly efficient in comparison.

Example 29

Comparison Between Mechanical and Chemical Recovery Methods

In this Example, a comparison is made between the efficiency of recovering lyase from the yeast cells by mechanical means, and by using LTAB.

Two transformants that expressed a high level of glucan lyase (transformant number 2 and 8) are grown at 24° C. (2 cultures of each transformant are started) since the expression of glucan lyase can be optimised at this temperature as seen in the growth experiment.

To compare the specific activity under repressed and induced conditions samples are collected when the cells are grown in YND+2% glucose (repressed) and in YND+1% glycerol with 1% methanol added on the second day of growth (induced).

FIG. 18 shows the ELISA-plate from the activity screening by the DNS method of the repressed and induced extracts. The assay is performed as described in S. Yu et al., 1998. The red colour indicates glucan lyase activity is much stronger when the induced cells are opened with LTAB compared with opening of the cells mechanically on a Mini Bead-Beater (E1-E12 compared with C1-C12). The specific activity is almost 60-fold higher in the case of LTAB-treated cells indicating that this is a much more effective way of releasing intracellular proteins in *H. polymorpha* (See FIG. 19). When the cells are grown in YND+2% glucose a very low specific activity is observed as expected since the FMD promoter is repressed in this media. The pellet from the LTAB opening is resuspended in 0.1 M MOPS-NaOH pH=6.2 and also assayed to check if some glucan lyase is still bound in the pellet. The assay detected a quite high glucan lyase activity in the pellet. A second round of LTAB incubation of the pellet did not release the glucan lyase so it is possible that the protein is bound to membranes.

The cell-free extract from the LTAB treated cells is used to purify the recombinant algal α-1,4-glucan lyase by FPLC on a starch column. The glucan lyase is eluted with 20 mM Bis-Tris-HCl pH=6.6+2% dextrin10 and a broad peak in the absorbance at 260 nm and at 280 is observed. Fraction 21-40 is tested for glucan lyase activity and the fractions with highest specific activity are collected into three larger fractions: Fraction I (fractions 21-26), fraction II (fraction 27-32) and fraction III (fraction 32-38) with fraction II having the highest specific activity. The purification of glucan lyase resulted in a yield of 61% and a fold of purification of 1.43 (See Table 20 below).

TABLE 20

Purification of recombinant algal α-1,4-glucan lyase by affinity chromatography on a starch column.

| Fraction | Total activity (U) | Total protein (mg) | Specific activity (U/mg) | Fold | Yield (%) |
| --- | --- | --- | --- | --- | --- |
| 1. Cell-free extract | 1237.95 | 11.76 | 105.26 | 1 | 100 |
| 2. Starch column | 757.86 | 5.04 | 150.34 | 1.43 | 61% |

In summary, the detergent LTAB is found to selectively extract the glucan lyase from the yeast biomass. This method proves to be much more effective than the mechanical method using glass beads as bullets (FIGS. 18 and 19).

Compared to previous expression systems (*P. pastoris* and *A. niger*) which only result in a specific activity of 0.70 μmol AF/min·mg protein, this Examples shows clearly that expression in *H. polymorpha* combined with purification using a quaternary ammonium compound CTAB is highly efficient in comparison.

Example 30

Further Purification of Recombinant Algal Glucan Lyase

The three fractions are concentrated with a Centriprep YM-30 and the purity of the glucan lyase is analysed by native PAGE (FIG. 20).

Comparison of the gels in FIG. 20 clearly indicates that a much better separation of the proteins is obtained on the gradient gel. On the homogenous gel it is not possible to distinguish between the raw extract and the purified glucan lyase. In lane 1 on the gradient gel it is very clear that glucan lyase is the predominant protein in the raw extract which is consistent with the very high expression of glucan lyase observed in the raw extract—90.2% of the proteins expressed in the raw extract is glucan lyase. Native-PAGE of all three fractions shows that the one-step purification on a starch column has resulted in a pure glucan lyase with an estimated purity of ≧95% FIG. 20 lane 2, 3 and 5 on the gradient gel). The broader band in some of the lanes is due to dextrin10 in the elusion buffer.

In summary, FIG. 20 clearly shows that the glucan lyase expressed in *H. polymorpha* can easily be purified to a high degree of purity—the protein is already 95% pure in the cell-free extract obtained by LTAB treatment.

Example 31

MALDI-TOF Mass Spectrometry and N-Terminal Sequencing

Glucan lyase in the three fractions is further purified by FPLC on an ion-exchange column in order to remove dextrin10 from the elution buffer. This is necessary since we wanted to analyze the purified protein by MALDI-TOF mass spectrometry that requires a very pure sample. The glucan lyase is eluted from the ion-exchange column with 10 mM Bis-Tris-HCl pH=7+1 M NaCl and activity screening of fraction B2-B6 revealed that all glucan lyase had been eluted in fraction B4 and B5. These two fractions are concentrated with a Centriprep YM-10 and the buffer is changed to 10 mM Bis-Tris-HCl pH=7 to remove the salts. A few microliter of fraction B5 is further desalted prior to the mass spectrometry analysis.

The molecular weight of the purified glucan lyase is determined to 115794±57 Da and 115722±57 Da, respectively; by two MALDI-TOF mass spectrometry analyses with the second analysis resulting in a molecular weight of 115722 Da being the best analysis. This purified algal α-1,4-glucan lyase from *H. polymorpha* has a smaller molecular weight than the algal α-1,4-glucan lyase purified from *Aspergillus niger* which has a molecular weight of 117030 Da as determined by MALDI-TOF mass spectrometry.

The N-terminal sequencing of the purified glucan lyase resulted in a sequence of 20 amino acids (GSTDNPDG-IDYKTYDYV GVW) (SEQ ID NO: 35) that was 100% identical with the wild type algal glucan lyase (See Table 21 below). Surprisingly the glucan lyase from *H. polymorpha* is very active even though the N-terminal is 11 amino acids shorter than the wild type protein.

TABLE 21

The N-terminal sequence of the wildtype algal α-1,4-glucan lyase and of the algal α-1,4-glucan lyase from *H. polymorpha*. An Applied Biosystems 476A Protein Sequencer was used for the N-terminal sequencing.

| | N-terminal sequence |
| --- | --- |
| Wild type glucan lyase (SEQ ID NO:36) | TALSDKQTATAGSTDNPDGIDYKTYDYVGVW |
| Algal glucan lyase from *H. Polymorpha* (SEQ ID NO:35) | GSTDNPDGIDYKTYDYVGVW |

The shorter N-terminal observed in the glucan lyase from *H. polymorpha* can explain the lower molecular weight determined by MALDI-TOF mass spectrometry. The molecular weight of the 11 amino acids in the N-terminal is 1088 Da. Thus, the molecular weight of the glucan lyase from *H. polymorpha* is expected to be 115942 Da (117030 Da−1088 Da) which is consistent with the molecular weight of 115722 Da determined by MALDI-TOF mass spectrometry.

The results shown in Examples 24 to 31 show that a glucan lyase of red algal origin with a mass over 117 kDa can be efficiently expressed in the yeast *Hansenula polymorpha*. It is also concluded the central and central+C-terminal parts of the gene are not sufficient for enzyme activity. Furthermore, it is clear from these Examples that the detergent LTAB is capable of selectively extracting the intracellularly expressed glucan lyase from the yeast biomass.

Example 32

Discussion (Examples 24 to 31)

The DNS method is used to assay for glucan lyase activity in the different transformants. This assay is specific for glucan lyase activity since only 1,5-anhydrofructose reacts so fast with the DNS reagent. The reaction of 1,5-anhydrofructose with the DNS reagent is completed in less than 10 minutes at room temperature (22° C.). In contrast it takes 5-10 minutes at 100° C. to complete the same reaction with D-glucose (Yu, S et al, 1998).

The DNS method is therefore a good way to assay for glucan lyase activity. The activity is determined in cell-free extracts prepared in two different ways: The cells are either opened mechanically on a Mini Bead-Beater or opened with the chemical reagent LTAB. The LTAB procedure resulted in a much more efficient release of the glucan lyase and is a good alternative for opening of *H. polymorpha* cells instead of the time consuming and inefficient mechanical method.

All four gene constructs had been integrated into the genome of *H. polymorpha* as determined by PCR screening and western blot analysis showed that glucan lyase is only expressed in the transformants containing the full-length gene and in a single transformant containing the 5' agl construct. Activity screening revealed that transformation of the full-length gene resulted in a very high glucan lyase activity. Thus, the expression of glucan lyase in *H. polymorpha* is much more efficient than seen in other expression systems (*Pichia pastoris* and *Aspergillus niger*).

No glucan lyase activity is detected with the truncated forms except in one case where the 5' agl construct is transformed. The aglcore construct consists of the minimum catalytic domain and this domain is probably not sufficient for activity since all 30 transformants failed to show any activity. In addition the aglcore and the 3' agl construct lacked the N-terminal domain which includes a starch-binding domain that is important for substrate binding. Since glucan lyase activity and expression only is detected for one transformant of the 5' agl construct it is possible that the starch-binding domain is damaged during the construction when different gene fragments are ligated. These data could indicate that the 5' end of the glucan lyase gene is more important than the 3' end but one active transformant is not sufficient to conclude this. It would be necessary to make some other truncated forms where a bigger part of the catalytic core is included so a higher number of transformants expressing the constructs can be compared.

The growth experiment revealed that the expression of glucan lyase is temperature dependent and can be optimised when growing the cells at 24° C. or 30° C. A 10-fold increase in expression of glucan lyase is observed compared with growth at 37° C. so these two temperatures are recommended for high expression of glucan lyase in *H. polymorpha*.

The glucan lyase expressed in *H. polymorpha* is purified on a starch column connected to a FPLC system. The identity of the purified glucan lyase is confirmed by MALDI-TOF mass spectrometry and N-terminal sequencing. The molecular weight of the purified glucan lyase is determined to 115722 Da by the MALDI-TOF mass spectrometry analysis and the N-terminal sequencing resulted in a sequence of 20 amino acids that is identical with the wild type protein. This two-step purification procedure by affinity chromatography and ion-exchange chromatography allows a quick and very efficient purification of algal glucan lyase and the protein is very pure even after the first step of purification (>95% purity).

Example 33

High Yields of Glucan Lyase in *Hansenula polymorpha* (Large Scale)

In this Example, two large scale fermentations with *Hansenula polymorpha* #42 containing an algal glucan lyase gene are carried out, and the intracellular levels of glucan lyase are quantified.

Microorganisms

The following strain of *H. polymorpha* is used in this study: HP #42 (DCDK0129, internal strain collection) obtained from Susan Madrid and Shukun Yu, DIC. This strain and the expression construct contained therein is also described in detail in Larsen, KS. 2003. Expression of algal α-1,4-glucan lyase in *Hansenula polymorpha*. B.Sc. report. The strain contained the glucan lyase gene under control of the formate dehydrogenase promoter and the methanol oxidase terminator from *H. polymorpha*.

Growth Media and Culture Conditions

YNB-Glycerol Medium

The medium used for preparation of inoculum for the bioreactor fermentations and for growth in shake flasks contained: 1.7 g/L Yeast Nitrogen Base (DIFCO, Detroit, USA, 0335-15-9), 5 g/L $(NH_4)_2SO_4$, 10 g/L glycerol, and 0.1 M 2-[N-Morpholino]ethanesulfonic acid (MES) as a buffer. The pH is adjusted to 6.1 (the pKa of MES) with 4 M NaOH (before autoclaving). Yeast Nitrogen Base and $(NH_4)_2SO_4$ are filter-sterilized to the medium after autoclaving. This medium is used for growth in shake flasks (250 mL medium in a shake flask with a total volume of 500 mL).

YNB Agar

The defined medium used for plating of stock cultures (kept at −80° C. in 25% (w/v) glycerol) contained: 1.7 g/L Yeast Nitrogen Base (DIFCO, Detroit, USA, 0335-15-9), 5 g/L $(NH_4)_2SO_4$, 10 g/L glycerol, and 20 g/L agar (DIFCO, Detroit, USA, 0140-01). Yeast Nitrogen Base and $(NH_4)_2SO_4$ are filter-sterilized to the medium after autoclaving.

YPD Agar

The rich medium is used for contamination check in the fermentors and for isolation of mutants. The medium contained: 10 g/L yeast extract, 10 g/L peptone, 20 g/L glycerol and 20 g/L agar.

Fermentation in Bioreactor

The batch medium (3 L) used for the fermentation in 6 L bioreactors contained: 13.3 g/L $NH_4H_2PO_4$, 3.0 g/L $MgSO_4.H_2O$, 3.3 g/L KCl, 0.3 g/L NaCl, 15 g/L glycerol, and 3 mL/L ADD APT® Foamstop Sin 260 (ADD APT Chemicals AG, Helmond, The Netherlands), 1.0 g/L $CaCl_2.2H_2O$, 67 mg/L $(NH_4)_2Fe(SO_4)_2.6H_2O$, 5 mg/L $CuSO_4.5H_2O$, 20 mg/L $ZnSO_4.7H_2O$, 21 mg/L $MnSO_4.H_2O$, and 67 mg/L EDTA), 0.65 mg/L $NiSO_4.6H_2O$, 0.65 mg/L $CoCl_2$, 0.65 mg/L $H_3BO_4$, 0.65 mg/L KI, 0.65 mg/L $Na_2MoO_4.2H_2O$), 2 mg/L D-biotin and 0.67 g/L thiaminchloride-hydrochloride.

The feed medium contained 630 g/kg glycerol and 133 g/kg formic acid. The pH is controlled by adding 8.75% (w/v) $NH_3$-water.

The fermentations are carried out as fed-batch cultivations in in-house built 6 L fermentors. The following fermentation conditions are used: pH 3.5 (GL0301) or 5.0 (GL0302), aeration 1 VVM, temperature 26° C., and stirring from 400 to 700 RPM.

The fermentor containing 3 L batch medium is inoculated 500 mL of *H. polymorpha* grown to an $OD_{600}$ of 10 in YNB medium at 25° C. at 200 RPM. The feed is initiated when more than 0.45 moles of carbon dioxide are evolved. The feed, 630 g/kg glycerol and 133 g/kg formic acid, is fed with a rate controlled by the accumulated $CO_2$ evolution, and based on the following equations:

Feed-flow$[g/h]$=0, $AccCO_2$<0.45

Feed-flow$[g/h]$=1.33·$V$·$AccCO_2$,
0.45≦$AccCO_2$≦3.25

Feed-flow$[g/h]$=4.33·$V$, 3.25≦$AccCO_2$

V: The fermentation broth volume [L]
$AccCO_2$: The accumulated $CO_2$ evolution [moles]

Analytical Procedures

Determination of Glucan Lyase Activity

A fermentation sample (10 mL) is centrifuged at 9000×g for 10 minutes, and the supernatant is replaced with 100 mM MES, pH 6.1 containing 0.2% (w/v) LTAB. The glucan lyase is extracted from the cells at 30° C. for 24 hours followed by centrifugation at 9000×g for 10 minutes to remove the cell debris. The supernatant is used for glucan lyase measurements.

The following reagents are used in the glucan lyase assay:

Substrate:

The following substrate is used: 20 g/L glycogen (Type III from rabbit liver, Sigma G8876) in 50 mM acetic acid, pH 4.0.

DNS Reagent

The DNS reagent is prepared by dissolving 1 g 3,5-dinitrosalicylic acid in 40 mL 1 M NaOH+30 mL water. Then 3 g potassium-sodium tartrate is added, and water is added to a total volume of 100 mL. The reagent is stored in a brown bottle.

Standard Curve

A standard curve is prepared by adding 0, 20, 40, 60, 80 and 100 µL 21 mmol/L 1,5-anhydro-D-fructose to microtiter wells, and adding water to a total volume of 100 µL. Then 100 µL DNS reagent is added and the micro titer plate is incubated at room temperature for 10 minutes, followed by measurement of absorbance at 550 nm.

Measurement of Glucan Lyase Activity

25 µL of sample and 75 µL substrate (preheated to 45° C.) is added to a micro titer well, and incubated for 15 minutes at 45° C. Then 100 µL DNS reagent is added, and the micro titer plate is incubated 10 minutes at room temperature, followed by absorbance measurement at 550 run. A blank, 100 mM MES, pH 6.1, is included.

The glucan lyase activity is calculated from the standard curve, and expressed in U/mL. 1 U is defined as the amount of glucan lyase that produces 1 µmol of 1,5-anhydro-D-fructose per minute at 45° C. at the above described conditions.

Biomass Growth

Growth of the yeast is followed by measuring the culture turbidity at 600 nm. The biomass concentration in a culture fluid is determined by centrifugation of 10 mL of culture fluid at 9000×g for 10 minutes in a pre weighed container. After centrifugation, the supernatant is removed and the container is weighed. The biomass concentration is calculated as g wet weight of cells per L culture fluid.

Results and Discussion

The two fermentations carried out are conducted exactly identically, except that GL0301 is carried out at pH 3.5 and GL0302 is carried out at pH 5.

FIG. 21 shows the development in biomass concentration and glucan lyase activity in the two fermentations.

It is seen that the biomass and glucan lyase development is somewhat slower for GL0301 than for GL0302. This may be explained by the sudden shift from pH 6.1 in the shake flask culture to pH 3.5 in the fermentor for GL0301, which may have slowed down the biomass growth and glucan lyase production. For GL0302 the pH shift is only from pH 6.1 to 5, which is probably not as harsh as the shift experienced by the culture in GL0301. From FIG. 21 it is seen that the activity of glucan lyase reaches about 370 U/mL for both fermentations. The biomass concentration reaches about 300 g/L for both fermentations.

Larsen (Larsen, K S. 2003. Expression of algal α-1,4-glucan lyase in *Hansenula polymorpha*. B.Sc. report) reported that the specific activity of glucan lyase is 105 U/mg when assayed on 20 g/L glycogen at pH 4, which may be considered comparable to the assay conditions used in this study (15 g/L glycogen, pH 4). Using this specific activity, the level of glucan lyase reaches 3.5 g/L protein at the end of the fermentations.

Conclusions

Glucan lyase from *G. lemaneiformis* is effectively produced in *H. polymorpha*. The estimated level of glucan lyase reached 370 U/mL at the end of the fermentation, both when the fermentation is carried out at pH 3.5 and at pH 5. This corresponds to a glucan lyase yield of 3.5 g/L.

Further Aspects of the Invention

Further aspects and embodiments of the invention are now set out in the following numbered paragraphs; it is to be understood that the invention encompasses these aspects:

Paragraph 1. A method for releasing a soluble or membrane associated intracellular protein of interest (POI) from a cell comprising the steps of: (a) providing a cell comprising a soluble or membrane associated intracellular POI; (b) contacting the cell with a membrane extracting composition; and (c) causing the POI to be released from the cell under conditions sufficient for the specific release of the POI and in a soluble form.

Paragraph 2. A method according to Paragraph 1 wherein the cell is a transformed cell.

Paragraph 3. A method according to Paragraph 1 or Paragraph 2 for releasing a POI from a transformed cell; wherein said POI is a HOX enzyme; said method comprising the steps of: (a) providing a transformed cell comprising a HOX enzyme; (b) contacting the transformed cell with a membrane extracting composition; and (c) causing the HOX enzyme to be released from the transformed cell under conditions sufficient for the specific release of the a HOX enzyme and in a soluble form.

Paragraph 4. A method for releasing a POI from a transformed cell; wherein said POI is an interleukin 1 receptor antagonist (IL-1ra) said method comprising the steps of: (a) providing a transformed cell comprising an IL-1ra; (b) contacting the transformed cell with a membrane extracting composition; and (c) causing the IL-1ra to be released from the transformed cell under conditions sufficient for the specific release of the IL-1ra and in a soluble form.

Paragraph 5. A method according to any one of the preceding Paragraphs wherein the cell is selected from the group consisting of yeast cells, fungal cells and bacterial cells, preferably from yeast and fungal cells.

Paragraph 6. A method according to any one of the preceding Paragraphs wherein the intracellular POI is produced by recombinant DNA techniques.

Paragraph 7. A method according to any one of the preceding Paragraphs wherein the membrane extracting composition comprises a quarternary ammonium compound.

Paragraph 8. A method according to any one of the preceding Paragraphs wherein the quarternary ammonium compound is selected from the group consisting of Lauroyl Trimethyl Ammonium Bromide (LTAB), Myristyl Trimethyl Ammonium Chloride (MTAC), Cetyl Trimethyl Ammonium Chloride (CTAC), Cetrimide, Cetyl Trimethyl Ammonium Bromide (CTAB), Stearoyl Trimethyl Ammonium Chloride (STAC), Stearoyl Trimethyl Ammonium Bromide (STAB), Benzalkonium Chloride (alkyldimethylbenzylammonium chloride), N-Cetylpyridinium Bromide (N-Hexadecylpyridinium bromide), N-Cetylpyridinium Chloride (N-Hexadecylpyridinium chloride), Benzyl Dimethyl Tetradecyl Ammonium Chloride, Benzyl Dimethyl Hexadecyl Ammonium Chloride and a combination of any two or more thereof.

Paragraph 9. A method according to any one of the preceding Paragraphs wherein the membrane extracting composition comprises from about 0.05% to about 0.6% by weight of the quarternary ammonium compound, preferably from about 0.1% to about 0.5% by weight of the quarternary ammonium compound, preferably from about 0.2% to about 0.45% by weight of the quarternary ammonium compound, more preferably about 0.4% by weight of the quarternary ammonium compound.

Paragraph 10. A method according to any one of preceding Paragraphs wherein the cell is contacted with the membrane extracting composition at temperatures from about 4° C. to 40° C., preferably from about 20° C. to about 30° C., more preferably about 25° C.

Paragraph 11. A method according to any one of preceding Paragraphs wherein the cell is contacted with the membrane extracting composition at a pH optima of from about 2.0 to about 11.0 (more especially from about to 5.0 to about 7.0, more especially about 6.3).

Paragraph 12. A method for screening for mutated cells or transformed cells producing elevated levels of a soluble or membrane associated intracellular POI comprising the steps of: (a) growing the mutated cells at 30° C.; (b) incubating the mutated cells or transformed cells with the membrane extracting composition as defined in Paragraph 7 or Paragraph 8; (c) recovering the cell free medium; (c) screening the cell free medium for elevated levels of the intracellular POI; such that the presence of the intracellular POI in the cell free medium is indicative that the intracellular POI has been released.

Paragraph 13. A membrane extracting composition suitable for specifically releasing a soluble or membrane associated intracellular POI wherein the composition is contacted with the cell under the following conditions: (a) a percentage by weight of quarternary ammonium compound from about 0.05% to about 0.6% (more especially from about 0.1% to about 0.5%, more especially from about 0.2% to about 0.45%, more especially about 0.4%); (b) a pH optima of from about 2.0 to about 11.0 (more especially from about to 5.0 to about 7.0, more especially about 6.3); (c) a temperature optima of from about 4° C. to about 40° C., (more especially from about 20° C. to about 30° C., more especially about 25° C.); such that the intracellular POI substantially free of contaminating proteins is obtained.

Paragraph 14. Use of a membrane extracting composition comprising a quarternary ammonium compound to selectively release a soluble or membrane associated intracellular POI.

Paragraph 15. A method according to any one of the preceding Paragraphs wherein the POI is a HOX enzyme.

Paragraph 16. A method according to Paragraph 15 wherein the HOX enzyme comprises the amino acid sequence set out in SEQ ID No 22 or a variant, homologue, derivative or fragment thereof.

Paragraph 17. A method according to Paragraph 15 or Paragraph 16 wherein the HOX enzyme is encoded by a nucleotide sequence set out in SEQ ID No 22 or a variant, homologue, derivative or fragment thereof.

Paragraph 18. A method according to Paragraph 15 or Paragraph 16 or Paragraph 17 wherein the HOX enzyme is encoded by a nucleotide sequence capable of hybridising to the nucleotide sequence set out in SEQ ID No 22 or a variant, homologue, derivative or fragment thereof or a sequence complementary to the hybridisable sequence.

Paragraph 19. A HOX enzyme producible by the method according to any one of the preceding Paragraphs wherein the HOX enzyme is encoded by a nucleotide sequence as defined in any one of Paragraphs 16-18 and wherein the nucleotide sequence is synthesised by the oligonucleotides as set out in SEQ ID Nos 2-22.

Paragraph 20. A POI as defined in Paragraph 1 or any dependent Paragraph thereon wherein the POI is released in a substantially non-glycoslyated form from a eukaryotic host organism Paragraph 21. A substantially non-glycosylated POI released from a eukaryotic host organism.

Paragraph 22. A substantially non-glycosylated POI according to Paragraph 21 wherein the POI is released by the method of any one of the preceding Paragraphs.

Paragraph 23. A method according to any one of the preceeding Paragraphs, in which the POI is an IL-1ra enzyme.

Paragraph 24. A method according to any one of the preceeding Paragraphs, in which the POI is a glucan lyase enzyme.

Paragraph 25. A method according to paragraph 24, in which the yield of glucan lyase is 1 g/litre or more.

Summary

In one broad aspect of the present invention a method is provided for releasing a soluble or membrane associated intracellular protein of interest (POI) comprising the steps of: providing a cell comprising a soluble or membrane associated intracellular POI; contacting the cell with a membrane extracting composition; and causing the POI to be released from the cell under conditions sufficient for the release of the POI and in a soluble form.

In another broad aspect of the present invention a method is provided for specifically releasing a soluble or membrane associated intracellular protein of interest (POI) comprising the steps of: providing a cell comprising a soluble or membrane associated intracellular POI; contacting the cell with a membrane extracting composition; and causing the POI to be released from the cell under conditions sufficient for the release of the POI but insufficient for the release of other contaminating proteins.

REFERENCES

Bojsen, K., S. Yu, Kragh, K. M., and Marcussen, J. A group of □-1,4-glucan lyases and their genes from the red alga *Gracilariopsis lemaneiformis*: purification, cloning, and heterologous expression. Biochim. Biophys. Acta 1430(1999): 396-402.

Bollag, D. M. and Edelstein, S. J. (1991) Protein Methods. New York, Wiley-Liss.

Crahay, J., Delcour, J. M. A. G. and Hanotier, J. D. V. (1992) Process for recovering polypeptides localized in the periplasmic space of yeast without breaking the cell wall by using an non-ionic detergent and a neutral salt. U.S. Pat. No. 5,124,256.

Craig, W. S. (1987) Purification of *pichia* produced lipophilic proteins. U.S. Pat. No. 4,683,293.

Gowda, L. R., Bachhawat, N. & Bhat, S. G. (1991) Permeabilization of baker's yeast by cetyltrimethylammonium bromide for intracellular enzyme catalysis. Enzyme Microb. Technol. 13, 154-157.

Hagen, I. M. and Hyam, J. S. (1988) *J. Cell Sci.* 89, 343-357.

Hansen, O. C. and Stougaard, P. (1997) Hexose oxidase from the red alga *Chondrus crispus*: purification, molecular cloning, and expression in *Pichia pastoris*. J. Biol. Chem. 272, 11581-11587.

Hunkapiller, M. W., Lujan, U., Ostrander, F., and Hood, L. E. (1983). Isolation of proteins from polyacrylamide gels for amino acid sequence analysis. Methods in Enzymology, 91: 227-236.

Joshi, M. S., Gowda, L. R. and Bhat, S. G. (1987) Permeabilization of yeast cells (*Kluyveromyces fragilis*) to lactose by cetyltrimethylammonium bromide. Biotechnol. Lett. 9, 549-554.

Joshi, M. S., Gowda, L. R., Katwa, L. C. and Bhat, S. G. (1989) Permeabilization of yeast cells (*Kluyveromyces fragilis*) to lactose by digitonin. Enzyme Microb. Technol. 11, 439-443.

King, A. T., Davey, M. R., Mellor, I. R, Mulligan, B. J. and Lowe, K. C. (1991) Surfactant effects on yeast cells. Enzyme Microb. Technol. 13, 148-153.

Miyake, T. and Shiosaka, M. (1974) Process for the extraction of enzymes from microorganisms. U.S. Pat. No. 3,801,461.

Naglak, T. J., Hettwer, D. J. and Wang, H. Y. (1990) Chemical permeabilization of cells for intracellular product release. In Separation processes in biotechnology (Asenjo, J. A. ed) Vol 9, chapter 7. M. Dekker, New York.

Poulsen, C. H. and Høstrup, P. B. (1998) Purification and characterization of a hexose oxidase with excellent strengthening effects in bread. Cereal Chem. 75, 51-57.

Schleif, R. F. and Wensink, P. C. (1981) Practical Methods in Molecular Biology. New York, Springer-Verlag.

Sekhar, S., Bhat, N. and Bhat, S. G. (1999) Preparation of detergent permeabilized Bakers' yeast whole cell catalase. Process Biochem. 34, 349-354.

Stougaard, P. and Hansen, O. C. (1996) Recombinant hexose oxidase, a method of producing same and use of such enzyme. WO 96/40935.

Sullivan, J. D., and Ikawa, M. (1973) Purification and characterization of hexose oxidase from the red alga *chondrus crispus*. Biochem. Biophys. Acta 309,11-22.

Yu, S., K. Bojsen, B. Svensson, and J. Marcussen: alpha-1,4-Glucan lyases producing 1,5-anhydro-D-fructose from starch and glycogen have sequence similarity to alpha-glucosidases. Biochim. Biophys. Acta. 1433(1-2) (1999): 1-15.

Yu, S., Olsen C E, Marcussen J: Methods for the assay of 1,5-anhydro-D-fructose and alpha-1,4-glucan lyase. Carbohydr Res 305: 73-82 (1998).

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

SEQUENCE LISTING PART OF THE DESCRIPTION

SEQ ID No 1
Ala-Thr-Leu-Pro-Gln-Lys-Asp-Pro-Gly-Tyr-

SEQ ID Nos 2-21
HOX1A
ACTCCATGGCTACTTTGCCACAAAAGGACCCAGGTTACATTGTTATTGAC
GTCAACGCTGG

HOX2B
CGAAATCGATGTTGGTACCAATCCATCTTCTGTTGAAACCTTGCTTCATG
GATGGCAATCTTGGGTCAGGCTTGTCTGGAGTACCAGCGTTGACGTCAAT
AACAATG

HOX3a
GATTGGTACCAACATCGATTTCGTTTACGTCGTTTACACTCCACAAGGTG
CTTGTACTGCTTTGGACAGAGCTATGGAAAAGTGTTCTCCAGGTACCGTC
AGAATC

HOX4b
TTCAACCAAACCAGTAACGTTGATAATAGCCTTGACACATTCGTCGAAAA
CGAAGTCTTCGTAACAGTGACCACCAGAAACGATTCTGACGGTACCTGGA
GAACAC

HOX5a
ATCAACGTTACTGGTTTGGTTGAATCTGGTTACGACGACGATAGAGGTTA
CTTCGTCTCTTCCGGTGACACCAACTGGGGTTCCTTCAAGACCTTGTTCA
GAGACCACGGTAGAGTTTTG

HOX6b
CAAACCGTGCAATCTGGCCAAAATACCGTCACCTCCACCGACAATGTGAC
CACCCAAACCGACGGAGTAACAGGAACCACCTGGCAAAACTCTACCGTGG
TCTCTGAAC

HOX7a
TTTGGCCAGATTGCACGGTTTGCCAGTCGATTGGTTATCCGGTGTTGAAG
TTGTCGTTAAGCCAGTCTTGACCGAAGACTCTGTTCTTAAGTACGTTCAC
AAGGATTCC

HOX8b
GGCAAATCCTTGAAGTAGTATTTGGTGATAATACCGAAGTTACCTCCACC
TCCACCAGTGTGAGCCCAAAACAACTCACCGTCGTTACCTTCGGAATCCT
TGTGAACGTACTTAAG

HOX9a
CAAATACTACTTCAAGGATTTGCCAATGTCTCCAAGAGGTGTCATCGCTT
CTAACTTACACTTCTCTTGGGACGGTTTCACTAGAGATGCCTTGCAAGAT
TTGTTGACTAAGTACTTC

HOX10b
GGAGGTATACAAGTACATAACAAACTCTTCAGCTGCTTGGTGGAAGATTT
GGAACTTACCAACAGTATTCTTCCAATCACATCTAGCCAACTTGAAGTAC
TTAGTCAACAAATCTTGC primer 1
ATCTTCCATCAGGCAGCTGAAGAGTTTGTTATGTACTTGTATACATCCTA
CTCTAACGACGCCGAGAGAGAAGTTGCCCAAGACAGACACTATCAT -continued primer 2
GAAAGGAGCCCAACCAGCATGACCACCAAGAGCTTTGGTAGGCTCGCATG
TTTTGTAGATCTGTTCAAT GTCAGCCTCCAAATGATAGTGTCTGTCTTG
GGC primer 3
GCTGGTTGGGCTCCTTTCCCTGTTAGACCTAGACCTAGACACACATCCAA
GACTTCTTATATGCATGAC GAGACTATGGACTACCCTTTC primer 4
AATCTGGAAGTCTGGAAAGTCCTTGATCATGTAAGCAGACTTGTACTTAC
CTCTCTGATTAGGACCGGAACCGTTGATAGTCTCAGTCAAAGCGTAGAAA
GGGTAGTCCATAGTCTCGTC primer 5
GACTTTCCAGACTTCCAGATTGATGTTATCTGGAAATACCTTACTGAGGT
TCCTGACGGTTTGACTAGTGCCGAAATGAAGGATGCTCTTCTTCAGGTTG
ATATGTTC primer 6
CTTGTCTTCTTCCTGCCAGTATGTCTGGTACTGCAGTTTGATGATGTACT -continued
CTCTCTGAGCAACTGCAGTAGCATCCCAAACAACCTTGTGAATCTCACCA
CCGAACATATCAACCTGAAGAAGAGC primer 7
ACATACTGGCAGGAAGAAGACAAGGATGCAGTTAACTTGAAGTGGATTAG
AGACTTTTACGAGGAGATGTATGAGCCTTATGGTGGTGTTCCAGACCCTA
ACACTCAG primer 8
GGCACCATACTTACCGTTCTTCCAGTTGTTCAAGTCAACATCAGGGTAGT
TGAAGTAGCATCCCTCAAAAACACCTTTACCACTCTCAACCTGAGTGTTA
GGGTCTGGAAC primer 9
AAGAACGGTAAGTATGGTGCCTTGGAACTTTACTTTTTGGGTAACCTGAA
CAGATTGATCAAGGCCAAATGGTTGTGGGATCCTAACGAGATCTTCACAA
ACAAACAGTCTATCCCT primer 10
GAATTCCGCGGCCGCCTACTATTTAGTCTGCTTAGGCTCCTTAAGAGGTT
TAGTAGGGATAGACTGTTT GTTTGTGAA

```
  1 ATG GCT ACT TTG CCA CAA AAG GAC CCA GGT TAC ATT GTT ATT
    M   A   T   L   P   Q   K   D   P   G   Y   I   V   I

43 GAC GTC AAC GCT GGT ACT CCA GAC AAG CCT GAC CCA AGA TTG
    D   V   N   A   G   T   P   D   K   P   D   P   R   L

85 CCA TCC ATG AAG CAA GGT TTC AAC AGA AGA TGG ATT GGT ACC
    P   S   M   K   Q   G   F   N   R   R   W   I   G   T

127 AAC ATC GAT TTC GTT TAC GTC GTT TAC ACT CCA CAA GGT GCT
    N   I   D   F   V   Y   V   V   Y   T   P   Q   G   A

169 TGT ACT GCT TTG GAC AGA GCT ATG GAA AAG TGT TCT CCA GGT
    C   T   A   L   D   R   A   M   E   K   C   S   P   G

211 ACC GTC AGA ATC GTT TCT GGT GGT CAC TGT TAC GAA GAC TTC
    T   V   R   I   V   S   G   G   H   C   Y   E   D   F

253 GTT TTC GAC GAA TGT GTC AAG GCT ATT ATC AAC GTT ACT GGT
    V   F   D   E   C   V   K   A   I   I   N   V   T   G

295 TTG GTT GAA TCT GGT TAC GAC GAC GAT AGA GGT TAC TTC GTC
    L   V   E   S   G   Y   D   D   D   R   G   Y   F   V

337 TCT TCC GGT GAC ACC AAC TGG GGT TCC TTC AAG ACC TTG TTC
    S   S   G   D   T   N   W   G   S   F   K   T   L   F

379 AGA GAC CAC GGT AGA GTT TTG CCA GGT GGT TCC TGT TAC TCC
    R   D   H   G   R   V   L   P   G   G   S   C   Y   S

421 GTC GGT TTG GGT GGT CAC ATT GTC GGT GGA GGT GAC GGT ATT
    V   G   L   G   G   H   I   V   G   G   G   D   G   I

463 TTG GCC AGA TTG CAC GGT TTG CCA GTC GAT TGG TTA TCC GGT
    L   A   R   L   H   G   L   P   V   D   W   L   S   G

505 GTT GAA GTT GTC GTT AAG CCA GTC TTG ACC GAA GAC TCT GTT
    V   E   V   V   V   K   P   V   L   T   E   D   S   V

547 CTT AAG TAC GTT CAC AAG GAT TCC GAA GGT AAC GAC GGT GAG
    L   K   Y   V   H   K   D   S   E   G   N   D   G   E

589 TTG TTT TGG GCT CAC ACT GGT GGA GGT GGA GGT AAC TTC GGT
    L   F   W   A   H   T   G   G   G   G   G   N   F   G

631 ATT ATC ACC AAA TAC TAC TTC AAG GAT TTG CCA ATG TCT CCA
    I   I   T   K   Y   Y   F   K   D   L   P   M   S   P

673 AGA GGT GTC ATC GCT TCT AAC TTA CAC TTC TCT TGG GAC GGT
    R   G   V   I   A   S   N   L   H   F   S   W   D   G

715 TTC ACT AGA GAT GCC TTG CAA GAT TTG TTG ACT AAG TAC TTC
    F   T   R   D   A   L   Q   D   L   L   T   K   Y   F
```

```
 757 AAG TTG GCT AGA TGT GAT TGG AAG AAT ACT GTT GGT AAG TTC
      K   L   A   R   C   D   W   K   N   T   V   G   K   F

799 CAA ATC TTC CAC CAA GCA GCT GAA GAG TTT GTT ATG TAC TTG
      Q   I   F   H   Q   A   A   E   E   F   V   M   Y   L

841 TAT ACA TCC TAC TCT AAC GAC GCC GAG AGA GAA GTT GCC CAA
      Y   T   S   Y   S   N   D   A   E   R   E   V   A   Q

883 GAC AGA CAC TAT CAT TTG GAG GCT GAC ATT GAA CAG ATC TAC
      D   R   H   Y   H   L   E   A   D   I   E   Q   I   Y

925 AAA ACA TGC GAG CCT ACC AAA GCT CTT GGT GGT CAT GCT GGT
      K   T   C   E   P   T   K   A   L   G   G   H   A   G

967 TGG GCT CCT TTC CCT GTT AGA CCT AGA AAG AGA CAC ACA TCC
      W   A   P   F   P   V   R   P   R   K   R   H   T   S

1009 AAG ACT TCT TAT ATG CAT GAC GAG ACT ATG GAC TAC CCT TTC
      K   T   S   Y   M   H   D   E   T   M   D   Y   P   F

1051 TAC GCT TTG ACT GAG ACT ATC AAC GGT TCC GGT CCT AAT CAG
      Y   A   L   T   E   T   I   N   G   S   G   P   N   Q

1093 AGA GGT AAG TAC AAG TCT GCT TAC ATG ATC AAG GAC TTT CCA
      R   G   K   Y   K   S   A   Y   M   I   K   D   F   P

1135 GAC TTC CAG ATT GAT GTT ATC TGG AAA TAC CTT ACT GAG GTT
      D   F   Q   I   D   V   I   W   K   Y   L   T   E   V

1177 CCT GAC GGT TTG ACT AGT GCC GAA ATG AAG GAT GCT CTT CTT
      P   D   G   L   T   S   A   E   M   K   D   A   L   L

1219 CAG GTT GAT ATG TTC GGT GGT GAG ATT CAC AAG GTT GTT TGG
      Q   V   D   M   F   G   G   E   I   H   K   V   V   W

1261 GAT GCT ACT GCA GTT GCT CAG AGA GAG TAC ATC ATC AAA CTG
      D   A   T   A   V   A   Q   R   E   Y   I   I   K   L

1303 CAG TAC CAG ACA TAC TGG CAG GAA GAA GAC AAG GAT GCA GTT
      Q   Y   Q   T   Y   W   Q   E   E   D   K   D   A   V

1345 AAC TTG AAG TGG ATT AGA GAC TTT TAC GAG GAG ATG TAT GAG
      N   L   K   W   I   R   D   F   Y   E   E   M   Y   E

1387 CCT TAT GGT GGT GTT CCA GAC CCT AAC ACT CAG GTT GAG AGT
      P   Y   G   G   V   P   D   P   N   T   Q   V   E   S

1429 GGT AAA GGT GTT TTT GAG GGA TGC TAC TTC AAC TAC CCT GAT
      G   K   G   V   F   E   G   C   Y   F   N   Y   P   D

1471 GTT GAC TTG AAC AAC TGG AAG AAC GGT AAG TAT GGT GCC TTG
      V   D   L   N   N   W   K   N   G   K   Y   G   A   L

1513 GAA CTT TAC TTT TTG GGT AAC CTG AAC AGA TTG ATC AAG GCC
      E   L   Y   F   L   G   N   L   N   R   L   I   K   A

1555 AAA TGG TTG TGG GAT CCT AAC GAG ATC TTC ACA AAC AAA CAG
      K   W   L   W   D   P   N   E   I   F   T   N   K   Q

1597 TCT ATC CCT ACT AAA CCT CTT AAG GAG CCT AAG CAG ACT AAA
      S   I   P   T   K   P   L   K   E   P   K   Q   T   K

1639 TAG TAG
```

The invention claimed is:

1. A method for extracting a soluble or membrane associated intracellular recombinant protein of interest (POI) from a bacterial, yeast or fungal cell, the POI being released from the bacterial, yeast or fungal cell, comprising the steps of:
   (a) providing a bacterial, yeast or fungal cell comprising a soluble or membrane associated intracellular recombinant POI;
   (b) releasing the recombinant POI from the cell by contacting the cell with a membrane extracting composition comprising a quaternary ammonium compound at a concentration of between 0.05% to 0.6% by weight, under conditions sufficient for the release of the recombinant POI in a soluble form; and,
   (c) recovering the recombinant POI from the membrane extracting composition;

wherein the quaternary ammonium compound is selected from the group consisting of Lauroyl Trimethyl Ammonium Bromide (LTAB), Myristyl Trimethyl Ammonium Chloride (MTAC), Cetyl Trimethyl Ammonium Chloride (CTAC), Cetrimide, Cetyl Trimethyl Ammonium Bromide (CTAB), Stearoyl Trimethyl Ammonium Chloride (STAC), Stearoyl Trimethyl Ammonium Bromide (STAB), Benzalkonium Chloride (alkyldimethylbenzylammonium chloride), N-Cetylpyridinium Bromide (N-Hexadecylpyridinium bromide), N-Cetylpyridinium Chloride (N-Hexadecylpyridinium chloride), Benzyl Dimethyl Tetradecyl Ammonium Chloride, Benzyl Dimethyl Hexadecyl Ammonium Chloride and a combination of any two or more thereof, and wherein the recombinant POI is a hexose oxidase (HOX) enzyme.

2. The method according to claim 1, wherein the membrane extracting composition comprises from about 0.1% to about 0.5% by weight of the quaternary ammonium compound.

3. The method according to claim 2, wherein the membrane extracting composition comprises from about 0.2% to about 0.45% by weight of the quaternary ammonium compound.

4. The method according to claim 3, wherein the membrane extracting composition comprises about 0.4% by weight of the quaternary ammonium compound.

5. The method according to claim 1, wherein the cell is contacted with the membrane extracting composition at temperatures from about 4° C. to 40° C.

6. The method according to claim 5, wherein the cell is contacted with the membrane extracting composition at temperatures from about 20° C. to about 30° C.

7. The method according to claim 6, wherein the cell is contacted with the membrane extracting composition at temperatures from about 25° C.

8. The method according to claim 1, wherein the cell is contacted with the membrane extracting composition at a pH of from about 2.0 to about 11.0.

9. The method according to claim 8, wherein the cell is contacted with the membrane extracting composition at a pH of from about 5.0 to about 7.0.

10. The method according to claim 9, wherein the cell is contacted with the membrane extracting composition at a pH of from about 6.3.

11. The method according to claim 1, wherein the hexose oxidase (HOX) enzyme comprises the amino acid sequence set out in SEQ ID No 23.

12. The method according to claim 1, wherein the hexose oxidase (HOX) enzyme is encoded by the nucleotide sequence set out in SEQ ID No 22.

13. The method according to claim 1, wherein the hexose oxidase (HOX) enzyme is encoded by sequence complementary to a nucleotide sequence capable of hybridizing to the nucleotide sequence set out in SEQ ID No 22.

* * * * *

UNITED STATES PATENT AND TRADEMARK OFFICE
CERTIFICATE OF CORRECTION

| | | |
|---|---|---|
| PATENT NO. | : 7,455,990 B2 | Page 1 of 1 |
| APPLICATION NO. | : 10/693234 | |
| DATED | : November 25, 2008 | |
| INVENTOR(S) | : Claus Lindvald Johansen et al. | |

It is certified that error appears in the above-identified patent and that said Letters Patent is hereby corrected as shown below:

ON THE TITLE PAGE,

Item (75) Inventors should read as follows:

Susan "Mampusta" --Mampusti-- Madrid, Vedbaek

Charlotte Horsmans Poulsen, "Braband" --Brabrand--

Signed and Sealed this

Sixteenth Day of June, 2009

JOHN DOLL
*Acting Director of the United States Patent and Trademark Office*

SEQUENCE LISTING

<160> NUMBER OF SEQ ID NOS: 36

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic N-terminal amino acid sequence

<400> SEQUENCE: 1

Ala Thr Leu Pro Gln Lys Asp Pro Gly Tyr
 1               5                  10

<210> SEQ ID NO 2
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
actccatggc tactttgcca caaaaggacc caggttacat tgttattgac gtcaacgctg    60
g                                                                    61

<210> SEQ ID NO 3
<211> LENGTH: 107
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cgaaatcgat gttggtacca atccatcttc tgttgaaacc ttgcttcatg gatggcaatc    60
ttgggtcagg cttgtctgga gtaccagcgt tgacgtcaat aacaatg                 107

<210> SEQ ID NO 4
<211> LENGTH: 106
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gattggtacc aacatcgatt tcgtttacgt cgtttacact ccacaaggtg cttgtactgc    60
tttggacaga gctatggaaa agtgttctcc aggtaccgtc agaatc                  106

<210> SEQ ID NO 5
<211> LENGTH: 106
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ttcaaccaaa ccagtaacgt tgataatagc cttgacacat tcgtcgaaaa cgaagtcttc    60
gtaacagtga ccaccagaaa cgattctgac ggtacctgga gaacac                  106

<210> SEQ ID NO 6
<211> LENGTH: 120
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
atcaacgtta ctggtttggt tgaatctggt tacgacgacg atagaggtta cttcgtctct    60

```
tccggtgaca ccaactgggg ttccttcaag accttgttca gagaccacgg tagagttttg    120
```

<210> SEQ ID NO 7
<211> LENGTH: 109
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

```
caaaccgtgc aatctggcca aaataccgtc acctccaccg acaatgtgac cacccaaacc    60
gacggagtaa caggaaccac ctggcaaaac tctaccgtgg tctctgaac               109
```

<210> SEQ ID NO 8
<211> LENGTH: 109
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
tttggccaga ttgcacggtt tgccagtcga ttggttatcc ggtgttgaag ttgtcgttaa    60
gccagtcttg accgaagact ctgttcttaa gtacgttcac aaggattcc                109
```

<210> SEQ ID NO 9
<211> LENGTH: 116
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

```
ggcaaatcct tgaagtagta tttggtgata ataccgaagt tacctccacc tccaccagtg    60
tgagcccaaa acaactcacc gtcgttacct tcggaatcct tgtgaacgta cttaag       116
```

<210> SEQ ID NO 10
<211> LENGTH: 118
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

```
caaatactac ttcaaggatt tgccaatgtc tccaagaggt gtcatcgctt ctaacttaca    60
cttctcttgg gacggtttca ctagagatgc cttgcaagat ttgttgacta agtacttc      118
```

<210> SEQ ID NO 11
<211> LENGTH: 118
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

```
ggaggtatac aagtacataa caaactcttc agctgcttgg tggaagattt ggaacttacc    60
aacagtattc ttccaatcac atctagccaa cttgaagtac ttagtcaaca aatcttgc      118
```

<210> SEQ ID NO 12
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
atcttccatc aggcagctga agagtttgtt atgtacttgt atacatccta ctctaacgac      60
gccgagagag aagttgccca agacagacac tatcat                                96

<210> SEQ ID NO 13
<211> LENGTH: 102
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gaaaggagcc caaccagcat gaccaccaag agctttggta ggctcgcatg ttttgtagat      60
ctgttcaatg tcagcctcca aatgatagtg tctgtcttgg gc                        102

<210> SEQ ID NO 14
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gctggttggg ctcctttccc tgttagacct agacctagac acacatccaa gacttcttat      60
atgcatgacg agactatgga ctacccttc                                        90

<210> SEQ ID NO 15
<211> LENGTH: 120
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aatctggaag tctggaaagt ccttgatcat gtaagcagac ttgtacttac ctctctgatt      60
aggaccggaa ccgttgatag tctcagtcaa agcgtagaaa gggtagtcca tagtctcgtc    120

<210> SEQ ID NO 16
<211> LENGTH: 108
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gactttccag acttccagat tgatgttatc tggaaatacc ttactgaggt tcctgacggt      60
ttgactagtg ccgaaatgaa ggatgctctt cttcaggttg atatgttc                 108

<210> SEQ ID NO 17
<211> LENGTH: 126
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 17
cttgtcttct tcctgccagt atgtctggta ctgcagtttg atgatgtact ctctctgagc    60
aactgcagta gcatcccaaa caaccttgtg aatctcacca ccgaacatat caacctgaag   120
aagagc                                                              126

<210> SEQ ID NO 18
<211> LENGTH: 108
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
acatactggc aggaagaaga caaggatgca gttaacttga agtggattag agacttttac    60
gaggagatgt atgagcctta tggtggtgtt ccagaccta acactcag                108

<210> SEQ ID NO 19
<211> LENGTH: 111
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ggcaccatac ttaccgttct tccagttgtt caagtcaaca tcagggtagt tgaagtagca    60
tccctcaaaa acacctttac cactctcaac ctgagtgtta gggtctggaa c            111

<210> SEQ ID NO 20
<211> LENGTH: 117
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aagaacggta agtatggtgc cttggaactt tacttttgg gtaacctgaa cagattgatc    60
aaggccaaat ggttgtggga tcctaacgag atcttcacaa acaaacagtc tatccct      117

<210> SEQ ID NO 21
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gaattccgcg gccgcctact atttagtctg cttaggctcc ttaagaggtt tagtagggat    60
agactgtttg tttgtgaa                                                  78

<210> SEQ ID NO 22
<211> LENGTH: 1644
<212> TYPE: DNA
<213> ORGANISM: Artificial Sequence
<220> FEATURE:
<223> OTHER INFORMATION: Description of Artificial Sequence: Nucleotide
``` sequence of synthetic Hox gene
<220> FEATURE:
<221> NAME/KEY: CDS
<222> LOCATION: (1)..(1644)

<400> SEQUENCE: 22

| | | | | | | | | | | | | | | | | |
|---|---|---|---|---|---|---|---|---|---|---|---|---|---|---|---|---|
| atg | gct | act | ttg | cca | caa | aag | gac | cca | ggt | tac | att | gtt | att | gac | gtc | 48 |
| Met | Ala | Thr | Leu | Pro | Gln | Lys | Asp | Pro | Gly | Tyr | Ile | Val | Ile | Asp | Val | |
| 1 | | | | 5 | | | | | 10 | | | | | 15 | | |
| aac | gct | ggt | act | cca | gac | aag | cct | gac | cca | aga | ttg | cca | tcc | atg | aag | 96 |
| Asn | Ala | Gly | Thr | Pro | Asp | Lys | Pro | Asp | Pro | Arg | Leu | Pro | Ser | Met | Lys | |
| | | | 20 | | | | | 25 | | | | | 30 | | | |
| caa | ggt | ttc | aac | aga | aga | tgg | att | ggt | acc | aac | atc | gat | ttc | gtt | tac | 144 |
| Gln | Gly | Phe | Asn | Arg | Arg | Trp | Ile | Gly | Thr | Asn | Ile | Asp | Phe | Val | Tyr | |
| | | 35 | | | | | 40 | | | | | 45 | | | | |
| gtc | gtt | tac | act | cca | caa | ggt | gct | tgt | act | gct | ttg | gac | aga | gct | atg | 192 |
| Val | Val | Tyr | Thr | Pro | Gln | Gly | Ala | Cys | Thr | Ala | Leu | Asp | Arg | Ala | Met | |
| | 50 | | | | | 55 | | | | | 60 | | | | | |
| gaa | aag | tgt | tct | cca | ggt | acc | gtc | aga | atc | gtt | tct | ggt | ggt | cac | tgt | 240 |
| Glu | Lys | Cys | Ser | Pro | Gly | Thr | Val | Arg | Ile | Val | Ser | Gly | Gly | His | Cys | |
| 65 | | | | | 70 | | | | | 75 | | | | | 80 | |
| tac | gaa | gac | ttc | gtt | ttc | gac | gaa | tgt | gtc | aag | gct | att | atc | aac | gtt | 288 |
| Tyr | Glu | Asp | Phe | Val | Phe | Asp | Glu | Cys | Val | Lys | Ala | Ile | Ile | Asn | Val | |
| | | | | 85 | | | | | 90 | | | | | 95 | | |
| act | ggt | ttg | gtt | gaa | tct | ggt | tac | gac | gac | gat | aga | ggt | tac | ttc | gtc | 336 |
| Thr | Gly | Leu | Val | Glu | Ser | Gly | Tyr | Asp | Asp | Asp | Arg | Gly | Tyr | Phe | Val | |
| | | | 100 | | | | | 105 | | | | | 110 | | | |
| tct | tcc | ggt | gac | acc | aac | tgg | ggt | tcc | ttc | aag | acc | ttg | ttc | aga | gac | 384 |
| Ser | Ser | Gly | Asp | Thr | Asn | Trp | Gly | Ser | Phe | Lys | Thr | Leu | Phe | Arg | Asp | |
| | | 115 | | | | | 120 | | | | | 125 | | | | |
| cac | ggt | aga | gtt | ttg | cca | ggt | ggt | tcc | tgt | tac | tcc | gtc | ggt | ttg | ggt | 432 |
| His | Gly | Arg | Val | Leu | Pro | Gly | Gly | Ser | Cys | Tyr | Ser | Val | Gly | Leu | Gly | |
| | 130 | | | | | 135 | | | | | 140 | | | | | |
| ggt | cac | att | gtc | ggt | gga | ggt | gac | ggt | att | ttg | gcc | aga | ttg | cac | ggt | 480 |
| Gly | His | Ile | Val | Gly | Gly | Gly | Asp | Gly | Ile | Leu | Ala | Arg | Leu | His | Gly | |
| 145 | | | | | 150 | | | | | 155 | | | | | 160 | |
| ttg | cca | gtc | gat | tgg | tta | tcc | ggt | gtt | gaa | gtt | gtc | gtt | aag | cca | gtc | 528 |
| Leu | Pro | Val | Asp | Trp | Leu | Ser | Gly | Val | Glu | Val | Val | Val | Lys | Pro | Val | |
| | | | | 165 | | | | | 170 | | | | | 175 | | |
| ttg | acc | gaa | gac | tct | gtt | ctt | aag | tac | gtt | cac | aag | gat | tcc | gaa | ggt | 576 |
| Leu | Thr | Glu | Asp | Ser | Val | Leu | Lys | Tyr | Val | His | Lys | Asp | Ser | Glu | Gly | |
| | | | 180 | | | | | 185 | | | | | 190 | | | |
| aac | gac | ggt | gag | ttg | ttt | tgg | gct | cac | act | ggt | gga | ggt | gga | ggt | aac | 624 |
| Asn | Asp | Gly | Glu | Leu | Phe | Trp | Ala | His | Thr | Gly | Gly | Gly | Gly | Gly | Asn | |
| | | 195 | | | | | 200 | | | | | 205 | | | | |
| ttc | ggt | att | atc | acc | aaa | tac | tac | ttc | aag | gat | ttg | cca | atg | tct | cca | 672 |
| Phe | Gly | Ile | Ile | Thr | Lys | Tyr | Tyr | Phe | Lys | Asp | Leu | Pro | Met | Ser | Pro | |
| | 210 | | | | | 215 | | | | | 220 | | | | | |
| aga | ggt | gtc | atc | gct | tct | aac | tta | cac | ttc | tct | tgg | gac | ggt | ttc | act | 720 |
| Arg | Gly | Val | Ile | Ala | Ser | Asn | Leu | His | Phe | Ser | Trp | Asp | Gly | Phe | Thr | |
| 225 | | | | | 230 | | | | | 235 | | | | | 240 | |
| aga | gat | gcc | ttg | caa | gat | ttg | ttg | act | aag | tac | ttc | aag | ttg | gct | aga | 768 |
| Arg | Asp | Ala | Leu | Gln | Asp | Leu | Leu | Thr | Lys | Tyr | Phe | Lys | Leu | Ala | Arg | |
| | | | | 245 | | | | | 250 | | | | | 255 | | |
| tgt | gat | tgg | aag | aat | act | gtt | ggt | aag | ttc | caa | atc | ttc | cac | caa | gca | 816 |
| Cys | Asp | Trp | Lys | Asn | Thr | Val | Gly | Lys | Phe | Gln | Ile | Phe | His | Gln | Ala | |
| | | | 260 | | | | | 265 | | | | | 270 | | | |
| gct | gaa | gag | ttt | gtt | atg | tac | ttg | tat | aca | tcc | tac | tct | aac | gac | gcc | 864 |
| Ala | Glu | Glu | Phe | Val | Met | Tyr | Leu | Tyr | Thr | Ser | Tyr | Ser | Asn | Asp | Ala | |
| | | 275 | | | | | 280 | | | | | 285 | | | | |

```
gag aga gaa gtt gcc caa gac aga cac tat cat ttg gag gct gac att      912
Glu Arg Glu Val Ala Gln Asp Arg His Tyr His Leu Glu Ala Asp Ile
    290                 295                 300 gaa cag atc tac aaa aca tgc gag cct acc aaa gct ctt ggt ggt cat      960
Glu Gln Ile Tyr Lys Thr Cys Glu Pro Thr Lys Ala Leu Gly Gly His
305                 310                 315                 320 gct ggt tgg gct cct ttc cct gtt aga cct aga aag aga cac aca tcc     1008
Ala Gly Trp Ala Pro Phe Pro Val Arg Pro Arg Lys Arg His Thr Ser
                325                 330                 335 aag act tct tat atg cat gac gag act atg gac tac cct ttc tac gct     1056
Lys Thr Ser Tyr Met His Asp Glu Thr Met Asp Tyr Pro Phe Tyr Ala
                340                 345                 350 ttg act gag act atc aac ggt tcc ggt cct aat cag aga ggt aag tac     1104
Leu Thr Glu Thr Ile Asn Gly Ser Gly Pro Asn Gln Arg Gly Lys Tyr
            355                 360                 365 aag tct gct tac atg atc aag gac ttt cca gac ttc cag att gat gtt     1152
Lys Ser Ala Tyr Met Ile Lys Asp Phe Pro Asp Phe Gln Ile Asp Val
370                 375                 380 atc tgg aaa tac ctt act gag gtt cct gac ggt ttg act agt gcc gaa     1200
Ile Trp Lys Tyr Leu Thr Glu Val Pro Asp Gly Leu Thr Ser Ala Glu
385                 390                 395                 400 atg aag gat gct ctt ctt cag gtt gat atg ttc ggt ggt gag att cac     1248
Met Lys Asp Ala Leu Leu Gln Val Asp Met Phe Gly Gly Glu Ile His
                405                 410                 415 aag gtt gtt tgg gat gct act gca gtt gct cag aga gag tac atc atc     1296
Lys Val Val Trp Asp Ala Thr Ala Val Ala Gln Arg Glu Tyr Ile Ile
                420                 425                 430 aaa ctg cag tac cag aca tac tgg cag gaa gaa gac aag gat gca gtt     1344
Lys Leu Gln Tyr Gln Thr Tyr Trp Gln Glu Glu Asp Lys Asp Ala Val
            435                 440                 445 aac ttg aag tgg att aga gac ttt tac gag gag atg tat gag cct tat     1392
Asn Leu Lys Trp Ile Arg Asp Phe Tyr Glu Glu Met Tyr Glu Pro Tyr
450                 455                 460 ggt ggt gtt cca gac cct aac act cag gtt gag agt ggt aaa ggt gtt     1440
Gly Gly Val Pro Asp Pro Asn Thr Gln Val Glu Ser Gly Lys Gly Val
465                 470                 475                 480 ttt gag gga tgc tac ttc aac tac cct gat gtt gac ttg aac aac tgg     1488
Phe Glu Gly Cys Tyr Phe Asn Tyr Pro Asp Val Asp Leu Asn Asn Trp
                485                 490                 495 aag aac ggt aag tat ggt gcc ttg gaa ctt tac ttt ttg ggt aac ctg     1536
Lys Asn Gly Lys Tyr Gly Ala Leu Glu Leu Tyr Phe Leu Gly Asn Leu
                500                 505                 510 aac aga ttg atc aag gcc aaa tgg ttg tgg gat cct aac gag atc ttc     1584
Asn Arg Leu Ile Lys Ala Lys Trp Leu Trp Asp Pro Asn Glu Ile Phe
            515                 520                 525 aca aac aaa cag tct atc cct act aaa cct ctt aag gag cct aag cag     1632
Thr Asn Lys Gln Ser Ile Pro Thr Lys Pro Leu Lys Glu Pro Lys Gln
530                 535                 540 act aaa tag tag                                                      1644
Thr Lys
545
```

<210> SEQ ID NO 23
<211> LENGTH: 546
<212> TYPE: PRT
<213> ORGANISM: Artificial Sequence
<220> FEATURE:
<223> OTHER INFORMATION: Description of Artificial Sequence: Amino acid
      sequence of synthetic Hox gene

<400> SEQUENCE: 23

-continued

```
Met Ala Thr Leu Pro Gln Lys Asp Pro Gly Tyr Ile Val Ile Asp Val
1               5                   10                  15

Asn Ala Gly Thr Pro Asp Lys Pro Asp Pro Arg Leu Pro Ser Met Lys
            20                  25                  30

Gln Gly Phe Asn Arg Arg Trp Ile Gly Thr Asn Ile Asp Phe Val Tyr
        35                  40                  45

Val Val Tyr Thr Pro Gln Gly Ala Cys Thr Ala Leu Asp Arg Ala Met
    50                  55                  60

Glu Lys Cys Ser Pro Gly Thr Val Arg Ile Val Ser Gly Gly His Cys
65                  70                  75                  80

Tyr Glu Asp Phe Val Phe Asp Glu Cys Val Lys Ala Ile Ile Asn Val
                85                  90                  95

Thr Gly Leu Val Glu Ser Gly Tyr Asp Asp Arg Gly Tyr Phe Val
            100                 105                 110

Ser Ser Gly Asp Thr Asn Trp Gly Ser Phe Lys Thr Leu Phe Arg Asp
        115                 120                 125

His Gly Arg Val Leu Pro Gly Gly Ser Cys Tyr Ser Val Gly Leu Gly
    130                 135                 140

Gly His Ile Val Gly Gly Asp Gly Ile Leu Ala Arg Leu His Gly
145                 150                 155                 160

Leu Pro Val Asp Trp Leu Ser Gly Val Glu Val Val Lys Pro Val
            165                 170                 175

Leu Thr Glu Asp Ser Val Leu Lys Tyr Val His Lys Asp Ser Glu Gly
        180                 185                 190

Asn Asp Gly Glu Leu Phe Trp Ala His Thr Gly Gly Gly Gly Asn
    195                 200                 205

Phe Gly Ile Ile Thr Lys Tyr Tyr Phe Lys Asp Leu Pro Met Ser Pro
210                 215                 220

Arg Gly Val Ile Ala Ser Asn Leu His Phe Ser Trp Asp Gly Phe Thr
225                 230                 235                 240

Arg Asp Ala Leu Gln Asp Leu Leu Thr Lys Tyr Phe Lys Leu Ala Arg
            245                 250                 255

Cys Asp Trp Lys Asn Thr Val Gly Lys Phe Gln Ile Phe His Gln Ala
        260                 265                 270

Ala Glu Glu Phe Val Met Tyr Leu Tyr Thr Ser Tyr Ser Asn Asp Ala
    275                 280                 285

Glu Arg Glu Val Ala Gln Asp Arg His Tyr His Leu Glu Ala Asp Ile
290                 295                 300

Glu Gln Ile Tyr Lys Thr Cys Glu Pro Thr Lys Ala Leu Gly Gly His
305                 310                 315                 320

Ala Gly Trp Ala Pro Phe Pro Val Arg Pro Arg Lys His Thr Ser
            325                 330                 335

Lys Thr Ser Tyr Met His Asp Glu Thr Met Asp Tyr Pro Phe Tyr Ala
        340                 345                 350

Leu Thr Glu Thr Ile Asn Gly Ser Gly Pro Asn Gln Arg Gly Lys Tyr
    355                 360                 365

Lys Ser Ala Tyr Met Ile Lys Asp Phe Pro Asp Phe Gln Ile Asp Val
370                 375                 380

Ile Trp Lys Tyr Leu Thr Glu Val Pro Asp Gly Leu Thr Ser Ala Glu
385                 390                 395                 400

Met Lys Asp Ala Leu Leu Gln Val Asp Met Phe Gly Gly Glu Ile His
            405                 410                 415

Lys Val Val Trp Asp Ala Thr Ala Val Ala Gln Arg Glu Tyr Ile Ile
```

```
                420             425             430
Lys Leu Gln Tyr Gln Thr Tyr Trp Gln Glu Asp Lys Asp Ala Val
        435                 440                 445
Asn Leu Lys Trp Ile Arg Asp Phe Tyr Glu Glu Met Tyr Glu Pro Tyr
        450                 455                 460
Gly Val Pro Asp Pro Asn Thr Gln Val Glu Ser Gly Lys Gly Val
465                 470                 475                 480
Phe Glu Gly Cys Tyr Phe Asn Tyr Pro Asp Val Asp Leu Asn Asn Trp
                485                 490                 495
Lys Asn Gly Lys Tyr Gly Ala Leu Glu Leu Tyr Phe Leu Gly Asn Leu
        500                 505                 510
Asn Arg Leu Ile Lys Ala Lys Trp Leu Trp Asp Pro Asn Glu Ile Phe
        515                 520                 525
Thr Asn Lys Gln Ser Ile Pro Thr Lys Pro Leu Lys Glu Pro Lys Gln
        530                 535                 540
Thr Lys
545

<210> SEQ ID NO 24
<211> LENGTH: 5
<212> TYPE: PRT
<213> ORGANISM: Schwanniomyces occidentalis

<400> SEQUENCE: 24

Ser Ala Ile Gln Ala
  1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      amino acid signal sequence

<400> SEQUENCE: 25

Met Ala Thr Leu Pro
  1               5

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      amino acid signal sequence

<400> SEQUENCE: 26

Ala Thr Leu Pro
  1

<210> SEQ ID NO 27
<211> LENGTH: 6
<212> TYPE: PRT
<213> ORGANISM: Saccharomyces cerevisiae

<400> SEQUENCE: 27

Lys Arg Glu Ala Glu Ala
  1               5

<210> SEQ ID NO 28
<211> LENGTH: 5
```

```
<212> TYPE: PRT
<213> ORGANISM: Aspergillus oryzae

<400> SEQUENCE: 28

Ala Pro Ala Leu Ala
 1               5

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gaattcatga ccgcattgtc cgacaaacaa acggct                              36

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
acccggggta gaagagccgg cagcaaacca gtt                                 33

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gggtgagctc tgccacttcc agggctgcgc tgttc                               35

<210> SEQ ID NO 32
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ggagatcttt attaatggtg atggtgatgg tgggtaattg tgatcacagc gtccgg        56

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggagatacta cctggaactc tggacaagag gac                                 33

<210> SEQ ID NO 34
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 34
gtttggatcc ccgccagtac ccac                                              24

<210> SEQ ID NO 35
<211> LENGTH: 20
<212> TYPE: PRT
<213> ORGANISM: Hansenula polymorpha

<400> SEQUENCE: 35

Gly Ser Thr Asp Asn Pro Asp Gly Ile Asp Tyr Lys Thr Tyr Asp Tyr
 1               5                  10                  15

Val Gly Val Trp
            20

<210> SEQ ID NO 36
<211> LENGTH: 31
<212> TYPE: PRT
<213> ORGANISM: Gracilariopsis lemaneiformis

<400> SEQUENCE: 36

Thr Ala Leu Ser Asp Lys Gln Thr Ala Thr Ala Gly Ser Thr Asp Asn
 1               5                  10                  15

Pro Asp Gly Ile Asp Tyr Lys Thr Tyr Asp Tyr Val Gly Val Trp
                20                  25                  30
```